US008268598B2

(12) United States Patent
Zhu et al.

(10) Patent No.: US 8,268,598 B2
(45) Date of Patent: Sep. 18, 2012

(54) MUTANT Δ5 DESATURASES MUTATED IN THE HEME-BINDING MOTIF (HPGG) AND THEIR USE IN MAKING POLYUNSATURATED FATTY ACIDS

(75) Inventors: Quinn Qun Zhu, West Chester, PA (US); Dana M. Walters Pollak, West Chester, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 286 days.

(21) Appl. No.: 12/562,161

(22) Filed: Sep. 18, 2009

(65) Prior Publication Data

US 2010/0075386 A1 Mar. 25, 2010

Related U.S. Application Data

(60) Provisional application No. 61/098,333, filed on Sep. 19, 2008.

(51) Int. Cl.
| | |
|---|---|
| C12P 7/64 | (2006.01) |
| C12N 1/20 | (2006.01) |
| C12N 1/00 | (2006.01) |
| C12N 1/12 | (2006.01) |
| C12N 15/00 | (2006.01) |
| C07H 21/04 | (2006.01) |

(52) U.S. Cl. ............... 435/134; 435/252.3; 435/254.11; 435/257.2; 435/320.1; 536/23.2; 536/23.7

(58) Field of Classification Search ............... None
See application file for complete search history.

(56) References Cited

U.S. PATENT DOCUMENTS

| | | | |
|---|---|---|---|
| 5,972,664 A | 10/1999 | Knutzon et al. | |
| 2007/0271632 A1 | 11/2007 | Damude et al. | |
| 2007/0277266 A1 * | 11/2007 | Damude et al. | ............... 800/281 |
| 2008/0155705 A1 | 6/2008 | Zank et al. | |

OTHER PUBLICATIONS

Saito et al., Eur. J. Biochem. 267:1813-1818, 2000.*
Patwardhan et al., J. Chromat. A 787:91-100, 1997.*
GenBank Accession No. ABK36322, Nov. 2006, 1 page.*
GenBank Accession No. CAE22346, Apr. 2005, 2 pages.*
Watts et al., Proc. Natl. Acad. Sci., USA 99:5854-5859, Apr. 2002.*
O. Sayanova et al., Histidine-41 of the Cytochrome B5 Domain of the Borage Delta-6 Fatty Acid Desaturase Is Essential for Enzyme Activity, Plant Physiology, 121 (1999), pp. 641-646.
A. Hongsthong et al., Revealing the Complementation of Ferredoxin by Cytochrome B5 in the Spirulina-Delta-6-Desaturation Reaction by N-Terminal Fusion and Co-Expression of the Fungal-Cytochrome B5 Domain and Spirulina-Delta-6-Acyl-Lipid Desaturase, Appl. Microbiol. Biotechnol., 72 (2006), pp. 1192-1201.
H. Guillou et al., Distinct Roles of Endoplasmic Reticulum Cytochrome B5 and Fused Cytochrome B5-Like Domain for Rat Delta-6-Desaturase Activity, J. Lipid Research, 45 (2004), pp. 32-40.
P. Sperling et al., The Evolution of Desaturases, Prostaglandins, Leukotrienes and Essential Fatty Acids, 68 (2003), pp. 73-95.
International Search Report, PCT International Application PCT/US2009/57393, Feb. 24, 2010.
Sayanova et al., The Alternative Pathway C20 D8-Desaturase From the Non-Photosynthetic Organism *Acanthamoeba castellanii* Is an Atypical Cytochrome B5-Fusion Desaturase, FEBS Letters 580 (2006), pp. 1946-1952.

* cited by examiner

*Primary Examiner* — David J Steadman

(57) ABSTRACT

The present invention relates to mutant Δ5 desaturases, which have the ability to convert dihomo-γ-linolenic acid [DGLA; 20:3 ω-6] to arachidonic acid [ARA; 20:4 ω-6] and/or eicosatetraenoic acid [ETA; 20:4 ω-3] to eicosapentaenoic acid [EPA; 20:5 ω-3] and which possess at least one mutation within the HPGG motif of the cytochrome $b_5$-like domain. Isolated nucleic acid fragments and recombinant constructs comprising such fragments encoding Δ5 desaturases, along with a method of making long chain polyunsaturated fatty acids ["PUFAs"] using these mutant Δ5 desaturases in oleaginous yeast, are disclosed.

10 Claims, 3 Drawing Sheets

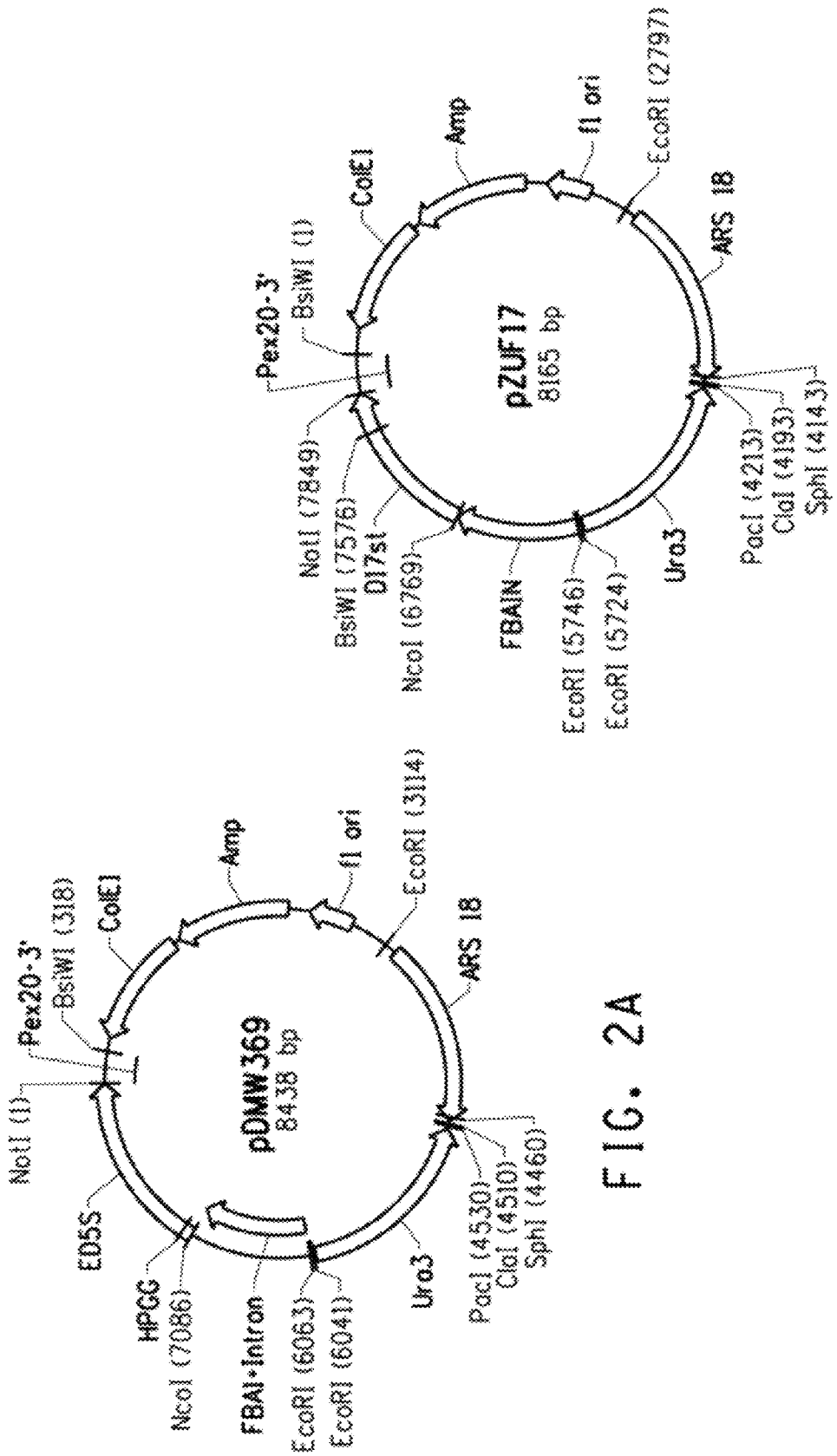

US 8,268,598 B2

Figure 1A:
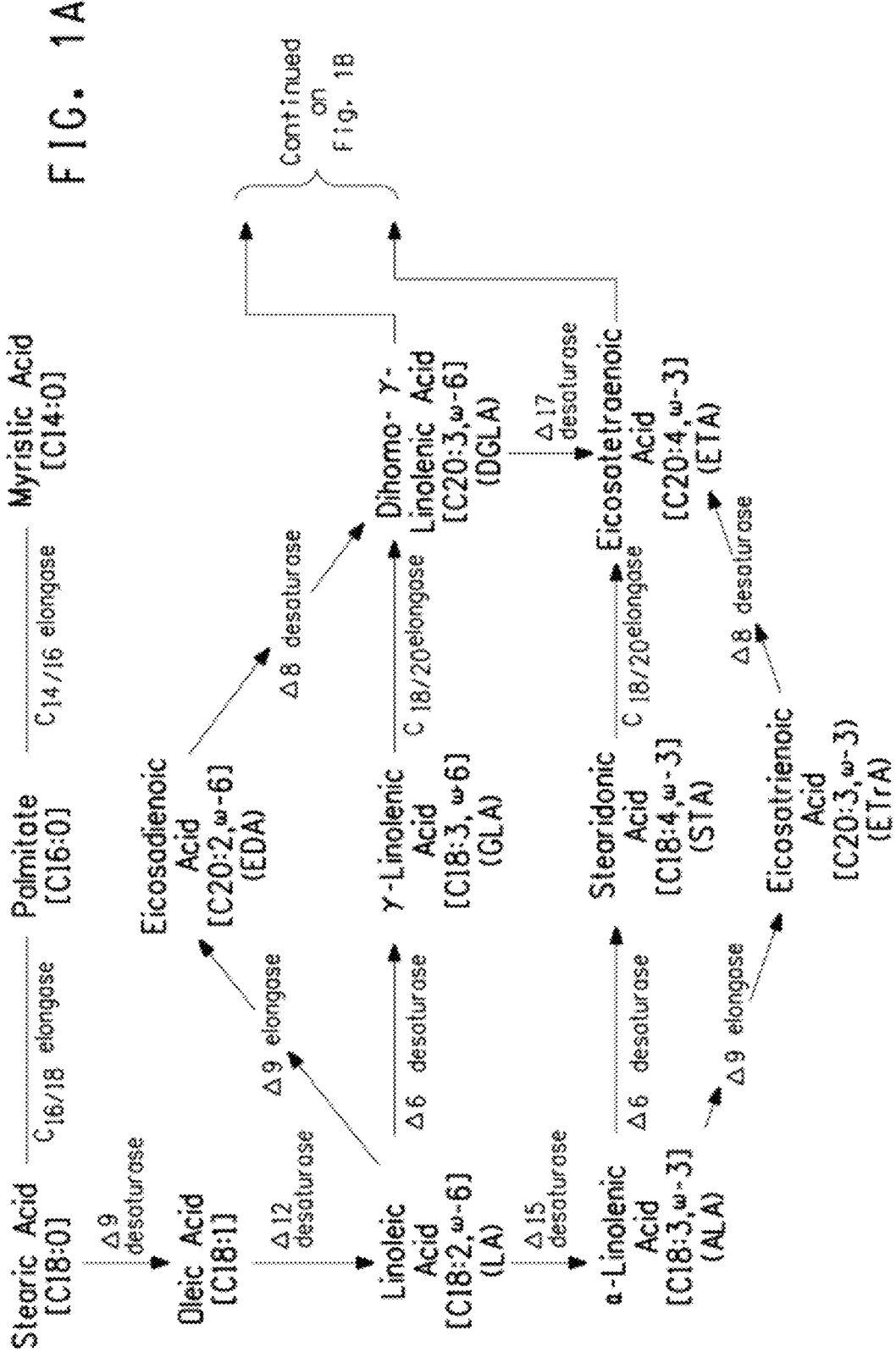

SEQUENCE LISTING

```
<160> NUMBER OF SEQ ID NOS: 195

<210> SEQ ID NO 1
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 1

His Xaa Xaa Xaa His
1               5

<210> SEQ ID NO 2
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(5)
<223> OTHER INFORMATION: Xaa can be any naturally occurring amino acid

<400> SEQUENCE: 2

His Xaa Xaa Xaa Xaa His
1               5

<210> SEQ ID NO 3
<211> LENGTH: 5
<212> TYPE: PRT
```

```
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 3

His Xaa Xaa His His
1               5

<210> SEQ ID NO 4
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: misc_feature
<222> LOCATION: (2)..(4)
<223> OTHER INFORMATION: Xaa can be any naturally occurring amino acid

<400> SEQUENCE: 4

His Xaa Xaa Xaa His His
1               5

<210> SEQ ID NO 5
<211> LENGTH: 5
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: Xaa = His [H] or Gln [Q]
<220> FEATURE:
<221> NAME/KEY: misc_feature
<222> LOCATION: (2)..(3)
<223> OTHER INFORMATION: Xaa can be any naturally occurring amino acid

<400> SEQUENCE: 5

Xaa Xaa Xaa His His
1               5

<210> SEQ ID NO 6
<211> LENGTH: 6
<212> TYPE: PRT
<213> ORGANISM: Artificial Sequence
<220> FEATURE:
<223> OTHER INFORMATION: His-rich motif
<220> FEATURE:
<221> NAME/KEY: MISC_FEATURE
<222> LOCATION: (1)..(1)
<223> OTHER INFORMATION: Xaa = His [H] or Gln [Q]
<220> FEATURE:
<221> NAME/KEY: misc_feature
<222> LOCATION: (2)..(4)
<223> OTHER INFORMATION: Xaa can be any naturally occurring amino acid

<400> SEQUENCE: 6

Xaa Xaa Xaa Xaa His His
1               5

<210> SEQ ID NO 7
<211> LENGTH: 1350
<212> TYPE: DNA
<213> ORGANISM: Euglena gracilis
<220> FEATURE:
<221> NAME/KEY: CDS
<222> LOCATION: (1)..(1350)
```

-continued

```
<223> OTHER INFORMATION: delta-5 desaturase
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: US-2007-0292924-A1
<311> PATENT FILING DATE: 2007-05-15
<312> PUBLICATION DATE: 2007-12-20
<313> RELEVANT RESIDUES IN SEQ ID NO: (1)..(1350)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: WO2007/136671
<311> PATENT FILING DATE: 2007-05-16
<312> PUBLICATION DATE: 2007-11-29
<313> RELEVANT RESIDUES IN SEQ ID NO: (1)..(1350)

<400> SEQUENCE: 7 atg gct ctc agt ctt acc aca gaa cag ctg tta gaa cgc cct gat ttg      48
Met Ala Leu Ser Leu Thr Thr Glu Gln Leu Leu Glu Arg Pro Asp Leu
1               5                   10                  15 gtt gcg att gat ggc atc ctc tac gac ctt gaa ggg ctt gcc aaa gtt      96
Val Ala Ile Asp Gly Ile Leu Tyr Asp Leu Glu Gly Leu Ala Lys Val
                20                  25                  30 cat cca gga gga gat ttg att ctc gct tct ggt gcc tct gat gcc tcc     144
His Pro Gly Gly Asp Leu Ile Leu Ala Ser Gly Ala Ser Asp Ala Ser
            35                  40                  45 cct ctc ttt tat tca atg cat cca tac gtc aaa ccg gag aat tcc aaa     192
Pro Leu Phe Tyr Ser Met His Pro Tyr Val Lys Pro Glu Asn Ser Lys
        50                  55                  60 ttg ctt caa cag ttc gtc cga ggg aag cat gac cgc acc tcg aag gac     240
Leu Leu Gln Gln Phe Val Arg Gly Lys His Asp Arg Thr Ser Lys Asp
65                  70                  75                  80 att gtc tac acg tat gat tct ccc ttc gca caa gac gtt aag cgg aca     288
Ile Val Tyr Thr Tyr Asp Ser Pro Phe Ala Gln Asp Val Lys Arg Thr
                85                  90                  95 atg cgc gag gtg atg aaa ggg agg aac tgg tac gca acc cct ggc ttc     336
Met Arg Glu Val Met Lys Gly Arg Asn Trp Tyr Ala Thr Pro Gly Phe
                100                 105                 110 tgg ctg cgc acc gtt ggg atc atc gcc gtg acg gcc ttt tgc gag tgg     384
Trp Leu Arg Thr Val Gly Ile Ile Ala Val Thr Ala Phe Cys Glu Trp
            115                 120                 125 cac tgg gct acc acg ggg atg gtg ctg tgg ggc ctg ttg act gga ttc     432
His Trp Ala Thr Thr Gly Met Val Leu Trp Gly Leu Leu Thr Gly Phe
        130                 135                 140 atg cac atg cag atc ggc tta tcc atc cag cat gat gcg tcc cac ggg     480
Met His Met Gln Ile Gly Leu Ser Ile Gln His Asp Ala Ser His Gly
145                 150                 155                 160 gcc atc agc aag aag cct tgg gtc aac gcc ctc ttc gcc tac ggc att     528
Ala Ile Ser Lys Lys Pro Trp Val Asn Ala Leu Phe Ala Tyr Gly Ile
                165                 170                 175 gac gtc atc gga tcg tcc cgg tgg att tgg ctg cag tcg cac atc atg     576
Asp Val Ile Gly Ser Ser Arg Trp Ile Trp Leu Gln Ser His Ile Met
                180                 185                 190 cgg cac cac acc tac acc aac cag cac ggc ctc gac ctg gat gcg gag     624
Arg His His Thr Tyr Thr Asn Gln His Gly Leu Asp Leu Asp Ala Glu
            195                 200                 205 tcg gca gag ccg ttc ctg gtg ttc cac aac tac ccc gcc gca aac acc     672
Ser Ala Glu Pro Phe Leu Val Phe His Asn Tyr Pro Ala Ala Asn Thr
        210                 215                 220 gcc cga aag tgg ttc cac cgc ttc caa gct tgg tac atg tac ctt gtg     720
Ala Arg Lys Trp Phe His Arg Phe Gln Ala Trp Tyr Met Tyr Leu Val
225                 230                 235                 240 ctg ggg gca tac ggg gta tcg ctg gtg tac aac ccg ctc tac att ttc     768
Leu Gly Ala Tyr Gly Val Ser Leu Val Tyr Asn Pro Leu Tyr Ile Phe
```

```
                      245                 250                 255
cgg atg cag cac aat gac acc atc cca gag tct gtc acg gcc atg cgg       816
Arg Met Gln His Asn Asp Thr Ile Pro Glu Ser Val Thr Ala Met Arg
        260                 265                 270 gag aat ggc ttt ctg cgg cgc tac cgc aca ctt gca ttc gtg atg cga       864
Glu Asn Gly Phe Leu Arg Arg Tyr Arg Thr Leu Ala Phe Val Met Arg
            275                 280                 285 gct ttc ttc atc ttc cgg acc gca ttc ttg ccc tgg tac ctc act ggg       912
Ala Phe Phe Ile Phe Arg Thr Ala Phe Leu Pro Trp Tyr Leu Thr Gly
290                 295                 300 acc tca ttg ctg atc acc att cct ctg gtg ccc act gca act ggt gcc       960
Thr Ser Leu Leu Ile Thr Ile Pro Leu Val Pro Thr Ala Thr Gly Ala
305                 310                 315                 320 ttc ttg acg ttc ttc ttc att ttg tcc cac aat ttt gat ggc tcc gaa      1008
Phe Leu Thr Phe Phe Phe Ile Leu Ser His Asn Phe Asp Gly Ser Glu
            325                 330                 335 cgg atc ccc gac aag aac tgc aag gtt aag agc tct gag aag gac gtt      1056
Arg Ile Pro Asp Lys Asn Cys Lys Val Lys Ser Ser Glu Lys Asp Val
        340                 345                 350 gag gct gac caa att gac tgg tat cgg gcg cag gtg gag acg tcc tcc      1104
Glu Ala Asp Gln Ile Asp Trp Tyr Arg Ala Gln Val Glu Thr Ser Ser
    355                 360                 365 aca tac ggt ggc ccc atc gcc atg ttc ttc act ggc ggt ctc aat ttc      1152
Thr Tyr Gly Gly Pro Ile Ala Met Phe Phe Thr Gly Gly Leu Asn Phe
370                 375                 380 cag atc gag cac cac ctc ttt ccc cgg atg tcg tct tgg cac tac ccc      1200
Gln Ile Glu His His Leu Phe Pro Arg Met Ser Ser Trp His Tyr Pro
385                 390                 395                 400 ttc gtc cag cag gcg gtc cgg gag tgt tgc gaa cgc cat gga gtg cga      1248
Phe Val Gln Gln Ala Val Arg Glu Cys Cys Glu Arg His Gly Val Arg
            405                 410                 415 tat gtt ttc tac cct acc atc gtc ggc aac atc atc tcc acc ctg aag      1296
Tyr Val Phe Tyr Pro Thr Ile Val Gly Asn Ile Ile Ser Thr Leu Lys
        420                 425                 430 tac atg cat aag gtg ggt gtc gtc cac tgc gtg aag gac gca cag gat      1344
Tyr Met His Lys Val Gly Val Val His Cys Val Lys Asp Ala Gln Asp
    435                 440                 445 tcc tga                                                              1350
Ser

<210> SEQ ID NO 8
<211> LENGTH: 449
<212> TYPE: PRT
<213> ORGANISM: Euglena gracilis

<400> SEQUENCE: 8

Met Ala Leu Ser Leu Thr Thr Glu Gln Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
            85                  90                  95

Met Arg Glu Val Met Lys Gly Arg Asn Trp Tyr Ala Thr Pro Gly Phe
```

```
                    100                 105                 110
Trp Leu Arg Thr Val Gly Ile Ile Ala Val Thr Ala Phe Cys Glu Trp
        115                 120                 125
His Trp Ala Thr Thr Gly Met Val Leu Trp Gly Leu Leu Thr Gly Phe
    130                 135                 140
Met His Met Gln Ile Gly Leu Ser Ile Gln His Asp Ala Ser His Gly
145                 150                 155                 160
Ala Ile Ser Lys Lys Pro Trp Val Asn Ala Leu Phe Ala Tyr Gly Ile
                165                 170                 175
Asp Val Ile Gly Ser Ser Arg Trp Ile Trp Leu Gln Ser His Ile Met
            180                 185                 190
Arg His His Thr Tyr Thr Asn Gln His Gly Leu Asp Leu Asp Ala Glu
        195                 200                 205
Ser Ala Glu Pro Phe Leu Val Phe His Asn Tyr Pro Ala Ala Asn Thr
    210                 215                 220
Ala Arg Lys Trp Phe His Arg Phe Gln Ala Trp Tyr Met Tyr Leu Val
225                 230                 235                 240
Leu Gly Ala Tyr Gly Val Ser Leu Val Tyr Asn Pro Leu Tyr Ile Phe
                245                 250                 255
Arg Met Gln His Asn Asp Thr Ile Pro Glu Ser Val Thr Ala Met Arg
            260                 265                 270
Glu Asn Gly Phe Leu Arg Arg Tyr Arg Thr Leu Ala Phe Val Met Arg
        275                 280                 285
Ala Phe Phe Ile Phe Arg Thr Ala Phe Leu Pro Trp Tyr Leu Thr Gly
    290                 295                 300
Thr Ser Leu Leu Ile Thr Ile Pro Leu Val Pro Thr Ala Thr Gly Ala
305                 310                 315                 320
Phe Leu Thr Phe Phe Ile Leu Ser His Asn Phe Asp Gly Ser Glu
                325                 330                 335
Arg Ile Pro Asp Lys Asn Cys Lys Val Lys Ser Ser Glu Lys Asp Val
            340                 345                 350
Glu Ala Asp Gln Ile Asp Trp Tyr Arg Ala Gln Val Glu Thr Ser Ser
        355                 360                 365
Thr Tyr Gly Gly Pro Ile Ala Met Phe Phe Thr Gly Gly Leu Asn Phe
    370                 375                 380
Gln Ile Glu His His Leu Phe Pro Arg Met Ser Ser Trp His Tyr Pro
385                 390                 395                 400
Phe Val Gln Gln Ala Val Arg Glu Cys Cys Glu Arg His Gly Val Arg
                405                 410                 415
Tyr Val Phe Tyr Pro Thr Ile Val Gly Asn Ile Ile Ser Thr Leu Lys
            420                 425                 430
Tyr Met His Lys Val Gly Val Val His Cys Val Lys Asp Ala Gln Asp
        435                 440                 445
Ser

<210> SEQ ID NO 9
<211> LENGTH: 1350
<212> TYPE: DNA
<213> ORGANISM: Euglena gracilis
<220> FEATURE:
<221> NAME/KEY: CDS
<222> LOCATION: (1)..(1350)
<223> OTHER INFORMATION: synthetic delta-5 desaturase (codon-optimized
      for Yarrowia lipolytica)
<300> PUBLICATION INFORMATION:
<302> TITLE: DELTA-5 DESATURASE AND ITS USE IN MAKING POLYUNSATURATED
      FATTY ACIDS
```

```
<310> PATENT DOCUMENT NUMBER: US-2007-0292924-A1
<311> PATENT FILING DATE: 2007-05-15
<312> PUBLICATION DATE: 2007-12-20
<313> RELEVANT RESIDUES IN SEQ ID NO: (1)..(1350)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: WO2007/136671
<311> PATENT FILING DATE: 2007-05-16
<312> PUBLICATION DATE: 2007-11-29
<313> RELEVANT RESIDUES IN SEQ ID NO: (1)..(1350)

<400> SEQUENCE: 9 atg gct ctc tcc ctt act acc gag cag ctg ctc gag cga ccc gac ctg      48
Met Ala Leu Ser Leu Thr Thr Glu Gln Leu Leu Glu Arg Pro Asp Leu
1               5                   10                  15 gtt gcc atc gac ggc att ctc tac gat ctg gaa ggt ctt gcc aag gtc      96
Val Ala Ile Asp Gly Ile Leu Tyr Asp Leu Glu Gly Leu Ala Lys Val
            20                  25                  30 cat ccc gga ggc gac ttg atc ctc gct tct ggt gcc tcc gat gct tct     144
His Pro Gly Gly Asp Leu Ile Leu Ala Ser Gly Ala Ser Asp Ala Ser
        35                  40                  45 cct ctg ttc tac tcc atg cac cct tac gtc aag ccc gag aac tcg aag     192
Pro Leu Phe Tyr Ser Met His Pro Tyr Val Lys Pro Glu Asn Ser Lys
    50                  55                  60 ctg ctt caa cag ttc gtg cga ggc aag cac gac cga acc tcc aag gac     240
Leu Leu Gln Gln Phe Val Arg Gly Lys His Asp Arg Thr Ser Lys Asp
65                  70                  75                  80 att gtc tac acc tac gac tct ccc ttt gca cag gac gtc aag cga act     288
Ile Val Tyr Thr Tyr Asp Ser Pro Phe Ala Gln Asp Val Lys Arg Thr
                85                  90                  95 atg cga gag gtc atg aaa ggt cgg aac tgg tat gcc aca cct gga ttc     336
Met Arg Glu Val Met Lys Gly Arg Asn Trp Tyr Ala Thr Pro Gly Phe
            100                 105                 110 tgg ctg cga acc gtt ggc atc att gct gtc acc gcc ttt tgc gag tgg     384
Trp Leu Arg Thr Val Gly Ile Ile Ala Val Thr Ala Phe Cys Glu Trp
        115                 120                 125 cac tgg gct act acc gga atg gtg ctg tgg ggt ctc ttg act gga ttc     432
His Trp Ala Thr Thr Gly Met Val Leu Trp Gly Leu Leu Thr Gly Phe
    130                 135                 140 atg cac atg cag atc ggc ctg tcc att cag cac gat gcc tct cat ggt     480
Met His Met Gln Ile Gly Leu Ser Ile Gln His Asp Ala Ser His Gly
145                 150                 155                 160 gcc atc agc aaa aag ccc tgg gtc aac gct ctc ttt gcc tac ggc atc     528
Ala Ile Ser Lys Lys Pro Trp Val Asn Ala Leu Phe Ala Tyr Gly Ile
                165                 170                 175 gac gtc att gga tcg tcc aga tgg atc tgg ctg cag tct cac atc atg     576
Asp Val Ile Gly Ser Ser Arg Trp Ile Trp Leu Gln Ser His Ile Met
            180                 185                 190 cga cat cac acc tac acc aat cag cat ggt ctc gac ctg gat gcc gag     624
Arg His His Thr Tyr Thr Asn Gln His Gly Leu Asp Leu Asp Ala Glu
        195                 200                 205 tcc gca gaa cca ttc ctt gtg ttc cac aac tac cct gct gcc aac act     672
Ser Ala Glu Pro Phe Leu Val Phe His Asn Tyr Pro Ala Ala Asn Thr
    210                 215                 220 gct cga aag tgg ttt cac cga ttc cag gcc tgg tac atg tac ctc gtg     720
Ala Arg Lys Trp Phe His Arg Phe Gln Ala Trp Tyr Met Tyr Leu Val
225                 230                 235                 240 ctt gga gcc tac ggc gtt tcg ctg gtg tac aac cct ctc tac atc ttc     768
Leu Gly Ala Tyr Gly Val Ser Leu Val Tyr Asn Pro Leu Tyr Ile Phe
                245                 250                 255 cga atg cag cac aac gac acc att ccc gag tct gtc aca gcc atg cga     816
Arg Met Gln His Asn Asp Thr Ile Pro Glu Ser Val Thr Ala Met Arg
```

```
                     260               265                270
gag aac ggc ttt ctg cga cgg tac cga acc ctt gca ttc gtt atg cga        864
Glu Asn Gly Phe Leu Arg Arg Tyr Arg Thr Leu Ala Phe Val Met Arg
        275                 280                 285 gct ttc ttc atc ttt cga acc gcc ttc ttg ccc tgg tat ctc act gga        912
Ala Phe Phe Ile Phe Arg Thr Ala Phe Leu Pro Trp Tyr Leu Thr Gly
290                 295                 300 acc tcc ctg ctc atc acc att cct ctg gtg ccc act gct acc ggt gcc        960
Thr Ser Leu Leu Ile Thr Ile Pro Leu Val Pro Thr Ala Thr Gly Ala
305                 310                 315                 320 ttc ctc acc ttc ttt ttc atc ttg tct cac aac ttc gat ggc tcg gag       1008
Phe Leu Thr Phe Phe Phe Ile Leu Ser His Asn Phe Asp Gly Ser Glu
                325                 330                 335 cga atc ccc gac aag aac tgc aag gtc aag agc tcc gag aag gac gtt       1056
Arg Ile Pro Asp Lys Asn Cys Lys Val Lys Ser Ser Glu Lys Asp Val
            340                 345                 350 gaa gcc gat cag atc gac tgg tac aga gct cag gtg gag acc tct tcc       1104
Glu Ala Asp Gln Ile Asp Trp Tyr Arg Ala Gln Val Glu Thr Ser Ser
        355                 360                 365 acc tac ggt gga ccc att gcc atg ttc ttt act ggc ggt ctc aac ttc       1152
Thr Tyr Gly Gly Pro Ile Ala Met Phe Phe Thr Gly Gly Leu Asn Phe
370                 375                 380 cag atc gag cat cac ctc ttt cct cga atg tcg tct tgg cac tat ccc       1200
Gln Ile Glu His His Leu Phe Pro Arg Met Ser Ser Trp His Tyr Pro
385                 390                 395                 400 ttc gtg cag caa gct gtc cga gag tgt tgc gaa cga cac gga gtt cgg       1248
Phe Val Gln Gln Ala Val Arg Glu Cys Cys Glu Arg His Gly Val Arg
                405                 410                 415 tac gtc ttc tac cct acc att gtg ggc aac atc att tcc acc ctc aag       1296
Tyr Val Phe Tyr Pro Thr Ile Val Gly Asn Ile Ile Ser Thr Leu Lys
            420                 425                 430 tac atg cac aaa gtc ggt gtg gtt cac tgt gtc aag gac gct cag gat       1344
Tyr Met His Lys Val Gly Val Val His Cys Val Lys Asp Ala Gln Asp
        435                 440                 445 tcc taa                                                                1350
Ser

<210> SEQ ID NO 10
<211> LENGTH: 449
<212> TYPE: PRT
<213> ORGANISM: Euglena gracilis

<400> SEQUENCE: 10

Met Ala Leu Ser Leu Thr Thr Glu Gln Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125
```

His Trp Ala Thr Thr Gly Met Val Leu Trp Gly Leu Leu Thr Gly Phe
            130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
290                 295                 300

Thr Ser Leu Leu Ile Thr Ile Pro Leu Val Pro Thr Ala Thr Gly Ala
305                 310                 315                 320

Phe Leu Thr Phe Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
        355                 360                 365

Thr Tyr Gly Gly Pro Ile Ala Met Phe Phe Thr Gly Gly Leu Asn Phe
370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415

Tyr Val Phe Tyr Pro Thr Ile Val Gly Asn Ile Ile Ser Thr Leu Lys
            420                 425                 430

Tyr Met His Lys Val Gly Val Val His Cys Val Lys Asp Ala Gln Asp
        435                 440                 445

Ser

```
<210> SEQ ID NO 11
<211> LENGTH: 1362
<212> TYPE: DNA
<213> ORGANISM: Euglena anabaena UTEX 373
<220> FEATURE:
<221> NAME/KEY: CDS
<222> LOCATION: (1)..(1362)
<223> OTHER INFORMATION: delta-5 desaturase
<300> PUBLICATION INFORMATION:
<302> TITLE: DELTA-5 DESATURASES AND THEIR USE IN MAKING POLYUNSATURATED
       FATTY ACIDS
<310> PATENT DOCUMENT NUMBER: WO 2008/137532
<311> PATENT FILING DATE: 2008-05-01
<312> PUBLICATION DATE: 2008-11-13
<313> RELEVANT RESIDUES IN SEQ ID NO: (1)..(1362)
<300> PUBLICATION INFORMATION:
```

<302> TITLE: DELTA-5 DESATURASES AND THEIR USE IN MAKING POLYUNSATURATED
FATTY ACIDS
<310> PATENT DOCUMENT NUMBER: US-2008-0274521-A1
<311> PATENT FILING DATE: 2008-04-29
<312> PUBLICATION DATE: 2008-11-16
<313> RELEVANT RESIDUES IN SEQ ID NO: (1)..(1362)

<400> SEQUENCE: 11

```
atg gcc acc atc tct ttg act act gag caa ctt tta gaa cac cca gaa      48
Met Ala Thr Ile Ser Leu Thr Thr Glu Gln Leu Leu Glu His Pro Glu
1               5                   10                  15 ctg gtt gca att gat ggg gtg ttg tac gat ctc ttc gga ctg gcg aaa      96
Leu Val Ala Ile Asp Gly Val Leu Tyr Asp Leu Phe Gly Leu Ala Lys
            20                  25                  30 gtg cat cca ggt ggc aac ctc att gaa gcc gcc ggt gcc tcc gac gga     144
Val His Pro Gly Gly Asn Leu Ile Glu Ala Ala Gly Ala Ser Asp Gly
        35                  40                  45 acc gcc ctg ttc tac tcc atg cac cct gga gtg aag cca gag aat tcg     192
Thr Ala Leu Phe Tyr Ser Met His Pro Gly Val Lys Pro Glu Asn Ser
    50                  55                  60 aag ctg ctg cag caa ttt gcc cga ggc aaa cac gaa cga agc tcg aag     240
Lys Leu Leu Gln Gln Phe Ala Arg Gly Lys His Glu Arg Ser Ser Lys
65                  70                  75                  80 gac cca gtg tac acc ttt gac agt ccc ttc gcc cag gat gtc aag cag     288
Asp Pro Val Tyr Thr Phe Asp Ser Pro Phe Ala Gln Asp Val Lys Gln
                85                  90                  95 agc gtt cgg gag gtc atg aag ggg cgc aac tgg tac gcc acg ccc ggc     336
Ser Val Arg Glu Val Met Lys Gly Arg Asn Trp Tyr Ala Thr Pro Gly
            100                 105                 110 ttt tgg ctg cgg acc gcg ctg atc atc gcg tgc act gcc ata ggc gaa     384
Phe Trp Leu Arg Thr Ala Leu Ile Ile Ala Cys Thr Ala Ile Gly Glu
        115                 120                 125 tgg tat tgg atc act acc ggg gca gtg atg tgg ggc atc ttc acc ggg     432
Trp Tyr Trp Ile Thr Thr Gly Ala Val Met Trp Gly Ile Phe Thr Gly
    130                 135                 140 tac ttc cac agc cag att ggg ttg gcg att caa cac gat gcc tct cac     480
Tyr Phe His Ser Gln Ile Gly Leu Ala Ile Gln His Asp Ala Ser His
145                 150                 155                 160 gga gcc atc agc aaa aag ccc tgg gtg aac gcc ttt ttc gcc tac ggc     528
Gly Ala Ile Ser Lys Lys Pro Trp Val Asn Ala Phe Phe Ala Tyr Gly
                165                 170                 175 atc gac gcc att gga tcc tcc cgc tgg atc tgg ctg cag tcc cac att     576
Ile Asp Ala Ile Gly Ser Ser Arg Trp Ile Trp Leu Gln Ser His Ile
            180                 185                 190 atg cgc cac cac acc tac acc aac cag cat ggc ctg gac ctg gac gct     624
Met Arg His His Thr Tyr Thr Asn Gln His Gly Leu Asp Leu Asp Ala
        195                 200                 205 gcc tcg gcg gag ccg ttc att ttg ttc cac tcc tac ccg gca aca aat     672
Ala Ser Ala Glu Pro Phe Ile Leu Phe His Ser Tyr Pro Ala Thr Asn
    210                 215                 220 gcg tca cga aag tgg tac cat cgg ttc cag gcg tgg tac atg tac atc     720
Ala Ser Arg Lys Trp Tyr His Arg Phe Gln Ala Trp Tyr Met Tyr Ile
225                 230                 235                 240 gtt ttg ggg atg tat ggt gtg tcg atg gtg tac aat ccg atg tac ttg     768
Val Leu Gly Met Tyr Gly Val Ser Met Val Tyr Asn Pro Met Tyr Leu
                245                 250                 255 ttc acg atg cag cac aac gac aca atc cca gag gcc acc tct ctt aga     816
Phe Thr Met Gln His Asn Asp Thr Ile Pro Glu Ala Thr Ser Leu Arg
            260                 265                 270 cca ggc agc ttt ttc aac cgg cag cgc gcc ttc gcc gtt tcc ctc cgc     864
Pro Gly Ser Phe Phe Asn Arg Gln Arg Ala Phe Ala Val Ser Leu Arg
        275                 280                 285
```

-continued

```
cta ctg ttc atc ttc cgc aac gcc ttc ctc ccc tgg tac atc gcg ggc        912
Leu Leu Phe Ile Phe Arg Asn Ala Phe Leu Pro Trp Tyr Ile Ala Gly
290                 295                 300 gcc tct ccg ctg ctc acc atc ctg ctg gtg cca acg gtc aca ggc atc        960
Ala Ser Pro Leu Leu Thr Ile Leu Leu Val Pro Thr Val Thr Gly Ile
305                 310                 315                 320 ttc ttg aca ttt gtt ttt gtg ctg tcc cat aac ttt gaa ggc gct gag       1008
Phe Leu Thr Phe Val Phe Val Leu Ser His Asn Phe Glu Gly Ala Glu
                325                 330                 335 cgg acc ccc gaa aag aac tgc aag gcc aaa agg gcc aag gag ggg aag       1056
Arg Thr Pro Glu Lys Asn Cys Lys Ala Lys Arg Ala Lys Glu Gly Lys
            340                 345                 350 gag gtc cgc gat gta gag gag gac cgg gtg gac tgg tac cgg gcg cag       1104
Glu Val Arg Asp Val Glu Glu Asp Arg Val Asp Trp Tyr Arg Ala Gln
        355                 360                 365 gcc gag acc gcg gcg acc tac ggg ggc agc gtc ggg atg atg ctg acc       1152
Ala Glu Thr Ala Ala Thr Tyr Gly Gly Ser Val Gly Met Met Leu Thr
370                 375                 380 ggc ggt ttg aac ctg cag atc gag cac cac ttg ttc ccc cgc atg tcc       1200
Gly Gly Leu Asn Leu Gln Ile Glu His His Leu Phe Pro Arg Met Ser
385                 390                 395                 400 tct tgg cac tac ccc ttc atc caa gat acg gtg cgg gaa tgt tgc aag       1248
Ser Trp His Tyr Pro Phe Ile Gln Asp Thr Val Arg Glu Cys Cys Lys
                405                 410                 415 cgc cat ggc gtg cgc tac aca tac tac ccg acc atc ctg gag aat ata       1296
Arg His Gly Val Arg Tyr Thr Tyr Tyr Pro Thr Ile Leu Glu Asn Ile
            420                 425                 430 atg tcc acg ctc cgc tac atg cag aag gtg ggc gtg gcc cac aca att       1344
Met Ser Thr Leu Arg Tyr Met Gln Lys Val Gly Val Ala His Thr Ile
        435                 440                 445 cag gat gcc cag gaa ttc                                                1362
Gln Asp Ala Gln Glu Phe
    450
```

<210> SEQ ID NO 12
<211> LENGTH: 454
<212> TYPE: PRT
<213> ORGANISM: Euglena anabaena UTEX 373

<400> SEQUENCE: 12

```
Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Pro Gly Gly Asn Leu Ile Glu Ala Gly Ala Ser Asp Gly
        35                  40                  45

Thr Ala Leu Phe Tyr Ser Met His Pro Gly Val Lys Pro Glu Asn Ser
    50                  55                  60

Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
    130                 135                 140
```

```
Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Phe Ala Tyr Gly
                165                 170                 175

Ile Asp Ala Ile Gly Ser Ser Arg Trp Ile Trp Leu Gln Ser His Ile
            180                 185                 190

Met Arg His His Thr Tyr Thr Asn Gln His Gly Leu Asp Leu Asp Ala
        195                 200                 205

Ala Ser Ala Glu Pro Phe Ile Leu Phe His Ser Tyr Pro Ala Thr Asn
    210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
            260                 265                 270

Pro Gly Ser Phe Phe Asn Arg Gln Arg Ala Phe Ala Val Ser Leu Arg
        275                 280                 285

Leu Leu Phe Ile Phe Arg Asn Ala Phe Leu Pro Trp Tyr Ile Ala Gly
    290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                325                 330                 335

Arg Thr Pro Glu Lys Asn Cys Lys Ala Lys Arg Ala Lys Glu Gly Lys
            340                 345                 350

Glu Val Arg Asp Val Glu Glu Asp Arg Val Asp Trp Tyr Arg Ala Gln
        355                 360                 365

Ala Glu Thr Ala Ala Thr Tyr Gly Gly Ser Val Gly Met Met Leu Thr
    370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                405                 410                 415

Arg His Gly Val Arg Tyr Thr Tyr Tyr Pro Thr Ile Leu Glu Asn Ile
            420                 425                 430

Met Ser Thr Leu Arg Tyr Met Gln Lys Val Gly Val Ala His Thr Ile
        435                 440                 445

Gln Asp Ala Gln Glu Phe
    450

<210> SEQ ID NO 13
<211> LENGTH: 1362
<212> TYPE: DNA
<213> ORGANISM: Euglena anabaena UTEX 373
<220> FEATURE:
<221> NAME/KEY: CDS
<222> LOCATION: (1)..(1362)
<223> OTHER INFORMATION: synthetic delta-5 desaturase (codon-optimized
      for Yarrowia lipolytica)
<300> PUBLICATION INFORMATION:
<302> TITLE: DELTA-5 DESATURASES AND THEIR USE IN MAKING POLYUNSATURATED
      FATTY ACIDS
<310> PATENT DOCUMENT NUMBER: WO 2008/137532
<311> PATENT FILING DATE: 2008-05-01
<312> PUBLICATION DATE: 2008-11-13
<313> RELEVANT RESIDUES IN SEQ ID NO: (1)..(1362)
<300> PUBLICATION INFORMATION:
<302> TITLE: DELTA-5 DESATURASES AND THEIR USE IN MAKING POLYUNSATURATED
      FATTY ACIDS
```

<310> PATENT DOCUMENT NUMBER: US-2008-0274521-A1
<311> PATENT FILING DATE: 2008-04-29
<312> PUBLICATION DATE: 2008-11-06
<313> RELEVANT RESIDUES IN SEQ ID NO: (1)..(1362)

<400> SEQUENCE: 13

| | | | | | | | | | | | | | | | | |
|---|---|---|---|---|---|---|---|---|---|---|---|---|---|---|---|---|
| atg | gcc | acc | atc | tcc | ctg | act | acc | gag | cag | ctc | ctg | gaa | cac | ccc | gag | 48 |
| Met | Ala | Thr | Ile | Ser | Leu | Thr | Thr | Glu | Gln | Leu | Leu | Glu | His | Pro | Glu | |
| 1 | | | | 5 | | | | | 10 | | | | | 15 | | |
| ctc | gtt | gcc | atc | gac | gga | gtc | ctg | tac | gat | ctc | ttc | ggt | ctg | gcc | aag | 96 |
| Leu | Val | Ala | Ile | Asp | Gly | Val | Leu | Tyr | Asp | Leu | Phe | Gly | Leu | Ala | Lys | |
| | | | 20 | | | | | 25 | | | | | 30 | | | |
| gtg | cat | cca | gga | ggc | aac | ctc | atc | gaa | gct | gcc | ggt | gca | tcc | gac | gga | 144 |
| Val | His | Pro | Gly | Gly | Asn | Leu | Ile | Glu | Ala | Ala | Gly | Ala | Ser | Asp | Gly | |
| | | 35 | | | | | 40 | | | | | 45 | | | | |
| acc | gct | ctg | ttc | tac | tcc | atg | cat | cct | gga | gtc | aag | cca | gag | aac | tcg | 192 |
| Thr | Ala | Leu | Phe | Tyr | Ser | Met | His | Pro | Gly | Val | Lys | Pro | Glu | Asn | Ser | |
| | 50 | | | | | 55 | | | | | 60 | | | | | |
| aag | ctt | ctg | cag | caa | ttt | gcc | cga | ggc | aag | cac | gaa | cga | agc | tcc | aag | 240 |
| Lys | Leu | Leu | Gln | Gln | Phe | Ala | Arg | Gly | Lys | His | Glu | Arg | Ser | Ser | Lys | |
| 65 | | | | | 70 | | | | | 75 | | | | | 80 | |
| gat | ccc | gtg | tac | acc | ttc | gac | tct | ccc | ttt | gct | cag | gac | gtc | aag | cag | 288 |
| Asp | Pro | Val | Tyr | Thr | Phe | Asp | Ser | Pro | Phe | Ala | Gln | Asp | Val | Lys | Gln | |
| | | | | 85 | | | | | 90 | | | | | 95 | | |
| tcc | gtt | cga | gag | gtc | atg | aag | ggt | cga | aac | tgg | tac | gcc | act | cct | ggc | 336 |
| Ser | Val | Arg | Glu | Val | Met | Lys | Gly | Arg | Asn | Trp | Tyr | Ala | Thr | Pro | Gly | |
| | | | 100 | | | | | 105 | | | | | 110 | | | |
| ttc | tgg | ctg | aga | acc | gca | ctc | atc | atc | gct | tgt | act | gcc | att | ggc | gag | 384 |
| Phe | Trp | Leu | Arg | Thr | Ala | Leu | Ile | Ile | Ala | Cys | Thr | Ala | Ile | Gly | Glu | |
| | | | 115 | | | | | 120 | | | | | 125 | | | |
| tgg | tac | tgg | atc | aca | acc | gga | gca | gtg | atg | tgg | ggt | atc | ttt | act | gga | 432 |
| Trp | Tyr | Trp | Ile | Thr | Thr | Gly | Ala | Val | Met | Trp | Gly | Ile | Phe | Thr | Gly | |
| | 130 | | | | | 135 | | | | | 140 | | | | | |
| tac | ttc | cac | tcg | cag | att | ggc | ttg | gcc | att | caa | cac | gat | gct | tct | cac | 480 |
| Tyr | Phe | His | Ser | Gln | Ile | Gly | Leu | Ala | Ile | Gln | His | Asp | Ala | Ser | His | |
| 145 | | | | | 150 | | | | | 155 | | | | | 160 | |
| gga | gcc | atc | agc | aaa | aag | ccc | tgg | gtc | aac | gcc | ttt | ttc | gct | tat | ggc | 528 |
| Gly | Ala | Ile | Ser | Lys | Lys | Pro | Trp | Val | Asn | Ala | Phe | Phe | Ala | Tyr | Gly | |
| | | | | 165 | | | | | 170 | | | | | 175 | | |
| atc | gac | gcc | att | ggt | tcc | tct | cgt | tgg | atc | tgg | ctg | cag | tcc | cac | att | 576 |
| Ile | Asp | Ala | Ile | Gly | Ser | Ser | Arg | Trp | Ile | Trp | Leu | Gln | Ser | His | Ile | |
| | | | 180 | | | | | 185 | | | | | 190 | | | |
| atg | cga | cat | cac | act | tac | acc | aac | cag | cat | ggc | ctc | gac | ctg | gat | gct | 624 |
| Met | Arg | His | His | Thr | Tyr | Thr | Asn | Gln | His | Gly | Leu | Asp | Leu | Asp | Ala | |
| | | | 195 | | | | | 200 | | | | | 205 | | | |
| gcc | tcg | gca | gag | ccg | ttc | atc | ttg | ttc | cac | tcc | tat | cct | gct | acc | aac | 672 |
| Ala | Ser | Ala | Glu | Pro | Phe | Ile | Leu | Phe | His | Ser | Tyr | Pro | Ala | Thr | Asn | |
| | 210 | | | | | 215 | | | | | 220 | | | | | |
| gcc | tct | cga | aag | tgg | tac | cac | cga | ttt | cag | gcg | tgg | tac | atg | tac | atc | 720 |
| Ala | Ser | Arg | Lys | Trp | Tyr | His | Arg | Phe | Gln | Ala | Trp | Tyr | Met | Tyr | Ile | |
| 225 | | | | | 230 | | | | | 235 | | | | | 240 | |
| gtt | ctg | gga | atg | tat | ggt | gtc | tcg | atg | gtg | tac | aat | ccc | atg | tac | ctc | 768 |
| Val | Leu | Gly | Met | Tyr | Gly | Val | Ser | Met | Val | Tyr | Asn | Pro | Met | Tyr | Leu | |
| | | | | 245 | | | | | 250 | | | | | 255 | | |
| ttc | aca | atg | cag | cac | aac | gac | acc | att | ccc | gag | gcc | act | tct | ctc | aga | 816 |
| Phe | Thr | Met | Gln | His | Asn | Asp | Thr | Ile | Pro | Glu | Ala | Thr | Ser | Leu | Arg | |
| | | | 260 | | | | | 265 | | | | | 270 | | | |
| cca | ggc | agc | ttt | ttc | aat | cgg | cag | cga | gct | ttc | gcc | gtt | tcc | ctt | cga | 864 |
| Pro | Gly | Ser | Phe | Phe | Asn | Arg | Gln | Arg | Ala | Phe | Ala | Val | Ser | Leu | Arg | |
| | | | 275 | | | | | 280 | | | | | 285 | | | |
| ctg | ctc | ttc | atc | ttc | cga | aac | gcc | ttt | ctt | ccc | tgg | tac | att | gct | ggt | 912 |

```
Leu Leu Phe Ile Phe Arg Asn Ala Phe Leu Pro Trp Tyr Ile Ala Gly
        290                 295                 300 gcc tct cct ctg ctc acc att ctt ctg gtg ccc acg gtc aca ggc atc      960
Ala Ser Pro Leu Leu Thr Ile Leu Leu Val Pro Thr Val Thr Gly Ile
305                 310                 315                 320 ttc ctc acc ttt gtg ttc gtt ctg tcc cat aac ttc gag gga gcc gaa     1008
Phe Leu Thr Phe Val Phe Val Leu Ser His Asn Phe Glu Gly Ala Glu
                325                 330                 335 cgg acc cca gag aag aac tgc aag gcc aaa cga gct aag gaa ggc aag     1056
Arg Thr Pro Glu Lys Asn Cys Lys Ala Lys Arg Ala Lys Glu Gly Lys
            340                 345                 350 gag gtc aga gac gtg gaa gag gat cga gtc gac tgg tac cga gca cag     1104
Glu Val Arg Asp Val Glu Glu Asp Arg Val Asp Trp Tyr Arg Ala Gln
        355                 360                 365 gcc gag act gct gcc acc tac ggt ggc agc gtg gga atg atg ctt aca     1152
Ala Glu Thr Ala Ala Thr Tyr Gly Gly Ser Val Gly Met Met Leu Thr
370                 375                 380 ggc ggt ctc aac ctg cag atc gag cat cac ttg ttt ccc cga atg tcc     1200
Gly Gly Leu Asn Leu Gln Ile Glu His His Leu Phe Pro Arg Met Ser
385                 390                 395                 400 tct tgg cac tat ccc ttc att caa gac acc gtt cgg gag tgt tgc aag     1248
Ser Trp His Tyr Pro Phe Ile Gln Asp Thr Val Arg Glu Cys Cys Lys
                405                 410                 415 cga cat ggc gtc cgt tac aca tac tat cct acc att ctc gag aac atc     1296
Arg His Gly Val Arg Tyr Thr Tyr Tyr Pro Thr Ile Leu Glu Asn Ile
            420                 425                 430 atg tcc act ctt cga tac atg cag aag gtg ggt gtt gct cac acc att     1344
Met Ser Thr Leu Arg Tyr Met Gln Lys Val Gly Val Ala His Thr Ile
        435                 440                 445 cag gat gcc cag gag ttc                                             1362
Gln Asp Ala Gln Glu Phe
    450

<210> SEQ ID NO 14
<211> LENGTH: 454
<212> TYPE: PRT
<213> ORGANISM: Euglena anabaena UTEX 373

<400> SEQUENCE: 14

Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
                20                  25                  30

Val His Pro Gly Gly Asn Leu Ile Glu Ala Ala Gly Ala Ser Asp Gly
            35                  40                  45

Thr Ala Leu Phe Tyr Ser Met His Pro Gly Val Lys Pro Glu Asn Ser
        50                  55                  60

Lys Leu Leu Gln Gln Phe Ala Arg Gly Lys His Glu Arg Ser Ser Lys
65                  70                  75                  80

Asp Pro Val Tyr Thr Phe Asp Ser Pro Phe Ala Gln Asp Val Lys Gln
                85                  90                  95

Ser Val Arg Glu Val Met Lys Gly Arg Asn Trp Tyr Ala Thr Pro Gly
            100                 105                 110

Phe Trp Leu Arg Thr Ala Leu Ile Ile Ala Cys Thr Ala Ile Gly Glu
        115                 120                 125

Trp Tyr Trp Ile Thr Thr Gly Ala Val Met Trp Gly Ile Phe Thr Gly
130                 135                 140

Tyr Phe His Ser Gln Ile Gly Leu Ala Ile Gln His Asp Ala Ser His
145                 150                 155                 160
```

```
Gly Ala Ile Ser Lys Lys Pro Trp Val Asn Ala Phe Ala Tyr Gly
                165                 170                 175

Ile Asp Ala Ile Gly Ser Ser Arg Trp Ile Trp Leu Gln Ser His Ile
                180                 185                 190

Met Arg His His Thr Tyr Thr Asn Gln His Gly Leu Asp Leu Asp Ala
                195                 200                 205

Ala Ser Ala Glu Pro Phe Ile Leu Phe His Ser Tyr Pro Ala Thr Asn
210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                245                 250                 255

Phe Thr Met Gln His Asn Asp Thr Ile Pro Glu Ala Thr Ser Leu Arg
                260                 265                 270

Pro Gly Ser Phe Phe Asn Arg Gln Arg Ala Phe Ala Val Ser Leu Arg
                275                 280                 285

Leu Leu Phe Ile Phe Arg Asn Ala Phe Leu Pro Trp Tyr Ile Ala Gly
                290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                325                 330                 335

Arg Thr Pro Glu Lys Asn Cys Lys Ala Lys Arg Ala Lys Glu Gly Lys
                340                 345                 350

Glu Val Arg Asp Val Glu Asp Arg Val Asp Trp Tyr Arg Ala Gln
                355                 360                 365

Ala Glu Thr Ala Ala Thr Tyr Gly Gly Ser Val Gly Met Met Leu Thr
                370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                405                 410                 415

Arg His Gly Val Arg Tyr Thr Tyr Tyr Pro Thr Ile Leu Glu Asn Ile
                420                 425                 430

Met Ser Thr Leu Arg Tyr Met Gln Lys Val Gly Val Ala His Thr Ile
                435                 440                 445

Gln Asp Ala Gln Glu Phe
    450

<210> SEQ ID NO 15
<211> LENGTH: 1392
<212> TYPE: DNA
<213> ORGANISM: Peridinium sp. CCMP626
<220> FEATURE:
<221> NAME/KEY: CDS
<222> LOCATION: (1)..(1392)
<223> OTHER INFORMATION: delta-5 desaturase
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: US-2007-0271632-A1
<311> PATENT FILING DATE: 2007-05-15
<312> PUBLICATION DATE: 2007-11-22
<313> RELEVANT RESIDUES IN SEQ ID NO: (1)..(1392)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: WO2007/136646
<311> PATENT FILING DATE: 2007-05-16
<312> PUBLICATION DATE: 2007-11-29
```

<313> RELEVANT RESIDUES IN SEQ ID NO: (1)..(1392)

<400> SEQUENCE: 15

```
atg gct cca gat gcg gac aag ttg aga cag cgc aag gcg caa tcg att     48
Met Ala Pro Asp Ala Asp Lys Leu Arg Gln Arg Lys Ala Gln Ser Ile
1               5                   10                  15 caa gac acg gct gat tcg caa gct acc gaa ctc aag att ggc acc ctg     96
Gln Asp Thr Ala Asp Ser Gln Ala Thr Glu Leu Lys Ile Gly Thr Leu
            20                  25                  30 aag ggc ttg cag ggg aca gaa atc gtc att gat gga gac att tac gat    144
Lys Gly Leu Gln Gly Thr Glu Ile Val Ile Asp Gly Asp Ile Tyr Asp
        35                  40                  45 ata aaa gac ttt gat cac ccc ggt ggt gaa tcc atc atg act ttt ggg    192
Ile Lys Asp Phe Asp His Pro Gly Gly Glu Ser Ile Met Thr Phe Gly
    50                  55                  60 gga aac gat gtc acc gcc acg tac aag atg atc cac ccc tac cac tct    240
Gly Asn Asp Val Thr Ala Thr Tyr Lys Met Ile His Pro Tyr His Ser
65                  70                  75                  80 aag cac cat ttg gag aag atg aag aaa gtg gga cga gtt ccg gac tac    288
Lys His His Leu Glu Lys Met Lys Lys Val Gly Arg Val Pro Asp Tyr
                85                  90                  95 acc tcg gaa tac aag ttt gat act ccc ttt gag cgt gaa atc aag caa    336
Thr Ser Glu Tyr Lys Phe Asp Thr Pro Phe Glu Arg Glu Ile Lys Gln
            100                 105                 110 gag gtc ttc aag att gtg cga cga ggc cgc gag ttt gga aca cct gga    384
Glu Val Phe Lys Ile Val Arg Arg Gly Arg Glu Phe Gly Thr Pro Gly
        115                 120                 125 tac ttc ttc cgg gct ttc tgc tac att gga ctt ttc ttt tac ttg cag    432
Tyr Phe Phe Arg Ala Phe Cys Tyr Ile Gly Leu Phe Phe Tyr Leu Gln
    130                 135                 140 tat ttg tgg gtc acg act ccc act acc ttt gcc ttg gcg atc ttc tat    480
Tyr Leu Trp Val Thr Thr Pro Thr Thr Phe Ala Leu Ala Ile Phe Tyr
145                 150                 155                 160 ggt gtt tcg caa gct ttc att ggt ttg aac gta caa cat gat gcc aac    528
Gly Val Ser Gln Ala Phe Ile Gly Leu Asn Val Gln His Asp Ala Asn
                165                 170                 175 cac gga gct gcc tcc aag aag cct tgg atc aat aac ttg cta gga ttg    576
His Gly Ala Ala Ser Lys Lys Pro Trp Ile Asn Asn Leu Leu Gly Leu
            180                 185                 190 ggg gct gac ttt atc gga ggt tcc aaa tgg ttg tgg atg aac cag cac    624
Gly Ala Asp Phe Ile Gly Gly Ser Lys Trp Leu Trp Met Asn Gln His
        195                 200                 205 tgg acg cac cac aca tac acc aac cac cat gag aag gat ccc gat gcc    672
Trp Thr His His Thr Tyr Thr Asn His His Glu Lys Asp Pro Asp Ala
    210                 215                 220 ttg ggc gct gaa cca atg ttg ttg ttc aat gat tat ccc ttg ggt cac    720
Leu Gly Ala Glu Pro Met Leu Leu Phe Asn Asp Tyr Pro Leu Gly His
225                 230                 235                 240 cca aag cgt act ttg att cac cac ttc cag gcc ttc tat tac ctt ttc    768
Pro Lys Arg Thr Leu Ile His His Phe Gln Ala Phe Tyr Tyr Leu Phe
                245                 250                 255 gtc ttg gcc gga tac tgg gtc tct tcg gtc ttc aac cct caa att ttg    816
Val Leu Ala Gly Tyr Trp Val Ser Ser Val Phe Asn Pro Gln Ile Leu
            260                 265                 270 gac ttg caa cac cgc ggt gct caa gcg gtt gga atg aaa atg gag aac    864
Asp Leu Gln His Arg Gly Ala Gln Ala Val Gly Met Lys Met Glu Asn
        275                 280                 285 gat tac att gcc aaa agc cga aag tat gcc atc ttc ttg cgt ctc ttg    912
Asp Tyr Ile Ala Lys Ser Arg Lys Tyr Ala Ile Phe Leu Arg Leu Leu
    290                 295                 300
```

```
tat att tac acc aac att gtc gct ccg atc caa aac caa ggc ttc tcg      960
Tyr Ile Tyr Thr Asn Ile Val Ala Pro Ile Gln Asn Gln Gly Phe Ser
305                 310                 315                 320 ttg acc gtg gtc gcc cac att ttg acc atg ggc gtc gct tcc agt ttg     1008
Leu Thr Val Val Ala His Ile Leu Thr Met Gly Val Ala Ser Ser Leu
                325                 330                 335 act ttg gcg act ctt ttt gcc ttg tcg cac aat ttt gaa aac gcg gat     1056
Thr Leu Ala Thr Leu Phe Ala Leu Ser His Asn Phe Glu Asn Ala Asp
            340                 345                 350 cgc gat ccc act tac gag gcc cgc aag gga gga gag cct gtt tgt tgg     1104
Arg Asp Pro Thr Tyr Glu Ala Arg Lys Gly Gly Glu Pro Val Cys Trp
        355                 360                 365 ttc aag tcg caa gtc gaa acc tcg tca act tac ggt ttc atc tcg         1152
Phe Lys Ser Gln Val Glu Thr Ser Ser Thr Tyr Gly Gly Phe Ile Ser
    370                 375                 380 ggt tgc ttg acg ggc gga ctc aac ttc caa gtg gaa cac cac ttg ttc     1200
Gly Cys Leu Thr Gly Gly Leu Asn Phe Gln Val Glu His His Leu Phe
385                 390                 395                 400 cct cgt atg agt tcg gcc tgg tac ccc tac att gcc cct act gtt cga     1248
Pro Arg Met Ser Ser Ala Trp Tyr Pro Tyr Ile Ala Pro Thr Val Arg
                405                 410                 415 gag gtt tgc aaa aag cac gga gtc aag tac gca tac tat ccc tgg gtc     1296
Glu Val Cys Lys Lys His Gly Val Lys Tyr Ala Tyr Tyr Pro Trp Val
            420                 425                 430 tgg caa aac ttg att tca act gtc aag tat ctg cat caa agc gga act     1344
Trp Gln Asn Leu Ile Ser Thr Val Lys Tyr Leu His Gln Ser Gly Thr
        435                 440                 445 gga tcc aac tgg aag aat ggc gcc aac ccc tac tcg gga aaa ttg taa     1392
Gly Ser Asn Trp Lys Asn Gly Ala Asn Pro Tyr Ser Gly Lys Leu
    450                 455                 460
```

<210> SEQ ID NO 16
<211> LENGTH: 463
<212> TYPE: PRT
<213> ORGANISM: Peridinium sp. CCMP626

<400> SEQUENCE: 16

```
Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175
```

```
His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
    210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
    290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp
        355                 360                 365

Phe Lys Ser Gln Val Glu Thr Ser Ser Thr Tyr Gly Phe Ile Ser
    370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
    450                 455                 460

<210> SEQ ID NO 17
<211> LENGTH: 1392
<212> TYPE: DNA
<213> ORGANISM: Peridinium sp. CCMP626
<220> FEATURE:
<221> NAME/KEY: CDS
<222> LOCATION: (1)..(1392)
<223> OTHER INFORMATION: synthetic delta-5 desaturase (codon-optimized
      for Yarrowia lipolytica)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: US-2007-0271632-A1
<311> PATENT FILING DATE: 2007-05-15
<312> PUBLICATION DATE: 2007-11-22
<313> RELEVANT RESIDUES IN SEQ ID NO: (1)..(1392)
<300> PUBLICATION INFORMATION:
<302> TITLE: DELTA-5 DESATURASE AND ITS USE IN MAKING POLYUNSATURATED
      FATTY ACIDS
<310> PATENT DOCUMENT NUMBER: WO2007/136646
<311> PATENT FILING DATE: 2007-05-16
<312> PUBLICATION DATE: 2007-11-29
<313> RELEVANT RESIDUES IN SEQ ID NO: (1)..(1392)
```

-continued

```
<400> SEQUENCE: 17 atg gct ccc gac gcc gac aag ctg cga cag cga aag gct cag tcc atc      48
Met Ala Pro Asp Ala Asp Lys Leu Arg Gln Arg Lys Ala Gln Ser Ile
1               5                   10                  15 cag gac act gcc gat tct cag gct acc gag ctc aag att ggc acc ctg      96
Gln Asp Thr Ala Asp Ser Gln Ala Thr Glu Leu Lys Ile Gly Thr Leu
            20                  25                  30 aag ggt ctc caa ggc acc gag atc gtc att gat ggc gac atc tac gac     144
Lys Gly Leu Gln Gly Thr Glu Ile Val Ile Asp Gly Asp Ile Tyr Asp
        35                  40                  45 atc aaa gac ttc gat cac cct gga ggc gaa tcc atc atg acc ttt ggt     192
Ile Lys Asp Phe Asp His Pro Gly Gly Glu Ser Ile Met Thr Phe Gly
    50                  55                  60 ggc aac gac gtt act gcc acc tac aag atg att cat ccc tac cac tcg     240
Gly Asn Asp Val Thr Ala Thr Tyr Lys Met Ile His Pro Tyr His Ser
65                  70                  75                  80 aag cat cac ctg gag aag atg aaa aag gtc ggt cga gtg ccc gac tac     288
Lys His His Leu Glu Lys Met Lys Lys Val Gly Arg Val Pro Asp Tyr
                85                  90                  95 acc tcc gag tac aag ttc gat act ccc ttc gaa cga gag atc aaa cag     336
Thr Ser Glu Tyr Lys Phe Asp Thr Pro Phe Glu Arg Glu Ile Lys Gln
            100                 105                 110 gag gtc ttc aag att gtg cga aga ggt cga gag ttt gga aca cct ggc     384
Glu Val Phe Lys Ile Val Arg Arg Gly Arg Glu Phe Gly Thr Pro Gly
        115                 120                 125 tac ttc ttt cga gcc ttc tgc tac atc ggt ctc ttt tac ctg cag         432
Tyr Phe Phe Arg Ala Phe Cys Tyr Ile Gly Leu Phe Phe Tyr Leu Gln
    130                 135                 140 tat ctc tgg gtt acc act cct acc act ttc gcc ctt gct atc ttc tac     480
Tyr Leu Trp Val Thr Thr Pro Thr Thr Phe Ala Leu Ala Ile Phe Tyr
145                 150                 155                 160 ggt gtg tct cag gcc ttc att ggc ctg aac gtc cag cac gac gcc aac     528
Gly Val Ser Gln Ala Phe Ile Gly Leu Asn Val Gln His Asp Ala Asn
                165                 170                 175 cac gga gct gcc tcc aaa aag ccc tgg atc aac aat ttg ctc ggc ctg     576
His Gly Ala Ala Ser Lys Lys Pro Trp Ile Asn Asn Leu Leu Gly Leu
            180                 185                 190 ggt gcc gac ttt atc gga ggc tcc aag tgg ctc tgg atg aac cag cac     624
Gly Ala Asp Phe Ile Gly Gly Ser Lys Trp Leu Trp Met Asn Gln His
        195                 200                 205 tgg acc cat cac act tac acc aac cat cac gag aag gat ccc gac gcc     672
Trp Thr His His Thr Tyr Thr Asn His His Glu Lys Asp Pro Asp Ala
    210                 215                 220 ctg ggt gca gag cct atg ctg ctc ttc aac gac tat ccc ttg ggt cac     720
Leu Gly Ala Glu Pro Met Leu Leu Phe Asn Asp Tyr Pro Leu Gly His
225                 230                 235                 240 ccc aag cga acc ctc att cat cac ttc caa gcc ttc tac tat ctg ttt     768
Pro Lys Arg Thr Leu Ile His His Phe Gln Ala Phe Tyr Tyr Leu Phe
                245                 250                 255 gtc ctt gct ggc tac tgg gtg tct tcg gtg ttc aac cct cag atc ctg     816
Val Leu Ala Gly Tyr Trp Val Ser Ser Val Phe Asn Pro Gln Ile Leu
            260                 265                 270 gac ctc cag cac cga ggt gcc cag gct gtc ggc atg aag atg gag aac     864
Asp Leu Gln His Arg Gly Ala Gln Ala Val Gly Met Lys Met Glu Asn
        275                 280                 285 gac tac att gcc aag tct cga aag tac gct atc ttc ctg cga ctc ctg     912
Asp Tyr Ile Ala Lys Ser Arg Lys Tyr Ala Ile Phe Leu Arg Leu Leu
    290                 295                 300 tac atc tac acc aac att gtg gct ccc atc cag aac caa ggc ttt tcg     960
Tyr Ile Tyr Thr Asn Ile Val Ala Pro Ile Gln Asn Gln Gly Phe Ser
```

|  |  |  |  |  |  |  |  |  |  |  |  | 305 |  |  |  |  | 310 |  |  |  |  | 315 |  |  |  |  | 320 |  |  |  |
ctc acc gtc gtt gct cac att ctt act atg ggt gtc gcc tcc agc ctg    1008
Leu Thr Val Val Ala His Ile Leu Thr Met Gly Val Ala Ser Ser Leu
            325                 330                 335 acc ctc gct act ctg ttc gcc ctc tcc cac aac ttc gag aac gca gat    1056
Thr Leu Ala Thr Leu Phe Ala Leu Ser His Asn Phe Glu Asn Ala Asp
        340                 345                 350 cgg gat ccc acc tac gag gct cga aag gga ggc gag cct gtc tgt tgg    1104
Arg Asp Pro Thr Tyr Glu Ala Arg Lys Gly Gly Glu Pro Val Cys Trp
    355                 360                 365 ttc aag tcg cag gtg gaa acc tcc tct act tac ggt ggc ttc att tcc    1152
Phe Lys Ser Gln Val Glu Thr Ser Ser Thr Tyr Gly Gly Phe Ile Ser
370                 375                 380 ggt tgc ctt aca ggc gga ctc aac ttt cag gtc gag cat cac ctg ttt    1200
Gly Cys Leu Thr Gly Gly Leu Asn Phe Gln Val Glu His His Leu Phe
385                 390                 395                 400 cct cga atg tcc tct gcc tgg tac ccc tac atc gct cct acc gtt cga    1248
Pro Arg Met Ser Ser Ala Trp Tyr Pro Tyr Ile Ala Pro Thr Val Arg
            405                 410                 415 gag gtc tgc aaa aag cac ggc gtc aag tac gcc tac tat ccc tgg gtg    1296
Glu Val Cys Lys Lys His Gly Val Lys Tyr Ala Tyr Tyr Pro Trp Val
        420                 425                 430 tgg cag aac ctc atc tcg acc gtc aag tac ctg cat cag tcc gga act    1344
Trp Gln Asn Leu Ile Ser Thr Val Lys Tyr Leu His Gln Ser Gly Thr
    435                 440                 445 ggc tcg aac tgg aag aac ggt gcc aat ccc tac tct ggc aag ctg taa    1392
Gly Ser Asn Trp Lys Asn Gly Ala Asn Pro Tyr Ser Gly Lys Leu
450                 455                 460

<210> SEQ ID NO 18
<211> LENGTH: 463
<212> TYPE: PRT
<213> ORGANISM: Peridinium sp. CCMP626

<400> SEQUENCE: 18

Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu

```
                 180             185             190
Gly Ala Asp Phe Ile Gly Gly Ser Lys Trp Leu Trp Met Asn Gln His
             195             200             205

Trp Thr His His Thr Tyr Thr Asn His His Glu Lys Asp Pro Asp Ala
210             215             220

Leu Gly Ala Glu Pro Met Leu Leu Phe Asn Asp Tyr Pro Leu Gly His
225             230             235             240

Pro Lys Arg Thr Leu Ile His His Phe Gln Ala Phe Tyr Tyr Leu Phe
                 245             250             255

Val Leu Ala Gly Tyr Trp Val Ser Ser Val Phe Asn Pro Gln Ile Leu
             260             265             270

Asp Leu Gln His Arg Gly Ala Gln Ala Val Gly Met Lys Met Glu Asn
         275             280             285

Asp Tyr Ile Ala Lys Ser Arg Lys Tyr Ala Ile Phe Leu Arg Leu Leu
     290             295             300

Tyr Ile Tyr Thr Asn Ile Val Ala Pro Ile Gln Asn Gln Gly Phe Ser
305             310             315             320

Leu Thr Val Val Ala His Ile Leu Thr Met Gly Val Ala Ser Ser Leu
                 325             330             335

Thr Leu Ala Thr Leu Phe Ala Leu Ser His Asn Phe Glu Asn Ala Asp
             340             345             350

Arg Asp Pro Thr Tyr Glu Ala Arg Lys Gly Gly Glu Pro Val Cys Trp
         355             360             365

Phe Lys Ser Gln Val Glu Thr Ser Ser Thr Tyr Gly Gly Phe Ile Ser
     370             375             380

Gly Cys Leu Thr Gly Gly Leu Asn Phe Gln Val Glu His His Leu Phe
385             390             395             400

Pro Arg Met Ser Ser Ala Trp Tyr Pro Tyr Ile Ala Pro Thr Val Arg
                 405             410             415

Glu Val Cys Lys Lys His Gly Val Lys Tyr Ala Tyr Tyr Pro Trp Val
             420             425             430

Trp Gln Asn Leu Ile Ser Thr Val Lys Tyr Leu His Gln Ser Gly Thr
         435             440             445

Gly Ser Asn Trp Lys Asn Gly Ala Asn Pro Tyr Ser Gly Lys Leu
     450             455             460

<210> SEQ ID NO 19
<211> LENGTH: 8438
<212> TYPE: DNA
<213> ORGANISM: Artificial Sequence
<220> FEATURE:
<223> OTHER INFORMATION: Plasmid pDMW369

<400> SEQUENCE: 19
ggccgcaagt gtggatgggg aagtgagtgc ccggttctgt gtgcacaatt ggcaatccaa      60
gatggatgga ttcaacacag ggatatagcg agctacgtgg tggtgcgagg atatagcaac     120
ggatatttat gtttgacact tgagaatgta cgatacaagc actgtccaag tacaatacta     180
aacatactgt acatactcat actcgtaccc gggcaacggt tcacttgag tgcagtggct      240 agtgctctta ctcgtacagt gtgcaatact gcgtatcata gtctttgatg tatatcgtat     300
tcattcatgt tagttgcgta cgagccgaa gcataaagtg taaagcctgg ggtgcctaat      360
gagtgagcta actcacatta ttgcgttgc gctcactgcc cgctttccag tcgggaaacc      420
tgtcgtgcca gctgcattaa tgaatcggcc aacgcgcggg gagaggcggt ttgcgtattg     480
ggcgctcttc cgcttcctcg ctcactgact cgctgcgctc ggtcgttcgg ctgcggcgag     540
```

```
cggtatcagc tcactcaaag gcggtaatac ggttatccac agaatcaggg gataacgcag    600
gaaagaacat gtgagcaaaa ggccagcaaa aggccaggaa ccgtaaaaag gccgcgttgc    660
tggcgttttt ccataggctc cgcccccctg acgagcatca caaaaatcga cgctcaagtc    720
agaggtggcg aaacccgaca ggactataaa gataccaggc gtttccccct ggaagctccc    780
tcgtgcgctc tcctgttccg accctgccgc ttaccggata cctgtccgcc tttctccctt    840
cgggaagcgt ggcgctttct catagctcac gctgtaggta tctcagttcg gtgtaggtcg    900
ttcgctccaa gctgggctgt gtgcacgaac cccccgttca gcccgaccgc tgcgccttat    960
ccggtaacta tcgtcttgag tccaacccgg taagacacga cttatcgcca ctggcagcag   1020
ccactggtaa caggattagc agagcgaggt atgtaggcgg tgctacagag ttcttgaagt   1080
ggtggcctaa ctacggctac actagaagga cagtatttgg tatctgcgct ctgctgaagc   1140
cagttacctt cggaaaaaga gttggtagct cttgatccgg caaacaaacc accgctggta   1200
gcggtggttt ttttgtttgc aagcagcaga ttacgcgcag aaaaaaagga tctcaagaag   1260
atcctttgat cttttctacg gggtctgacg ctcagtggaa cgaaaactca cgttaaggga   1320
ttttggtcat gagattatca aaaaggatct tcacctagat ccttttaaat taaaaatgaa   1380
gttttaaatc aatctaaagt atatatgagt aaacttggtc tgacagttac caatgcttaa   1440
tcagtgaggc acctatctca gcgatctgtc tatttcgttc atccatagtt gcctgactcc   1500
ccgtcgtgta gataactacg atacgggagg gcttaccatc tggccccagt gctgcaatga   1560
taccgcgaga cccacgctca ccggctccag atttatcagc aataaaccag ccagccggaa   1620
gggccgagcg cagaagtggt cctgcaactt tatccgcctc catccagtct attaattgtt   1680
gccgggaagc tagagtaagt agttcgccag ttaatagttt cgcaacgtt gttgccattg    1740 ctacaggcat cgtggtgtca cgctcgtcgt ttggtatggc ttcattcagc tccggttccc   1800
aacgatcaag gcgagttaca tgatccccca tgttgtgcaa aaaagcggtt agctccttcg   1860
gtcctccgat cgttgtcaga agtaagttgg ccgcagtgtt atcactcatg gttatggcag   1920
cactgcataa ttctcttact gtcatgccat ccgtaagatg cttttctgtg actggtgagt   1980
actcaaccaa gtcattctga gaatagtgta tgcggcgacc gagttgctct tgcccggcgt   2040
caatacggga taataccgcg ccacatagca gaactttaaa agtgctcatc attggaaaac   2100
gttcttcggg gcgaaaactc tcaaggatct taccgctgtt gagatccagt tcgatgtaac   2160
ccactcgtgc acccaactga tcttcagcat cttttacttt caccagcgtt tctgggtgag   2220
caaaaacagg aaggcaaaat gccgcaaaaa agggaataag ggcgacacgg aaatgttgaa   2280
tactcatact cttcctttt caatattatt gaagcattta tcagggttat tgtctcatga   2340
gcggatacat atttgaatgt atttagaaaa ataaacaaat aggggttccg cgcacatttc   2400
cccgaaaagt gccacctgac gcgcctgta gcggcgcatt aagcgcggcg ggtgtggtgg   2460
ttacgcgcag cgtgaccgct acacttgcca gcgccctagc gcccgctcct ttcgctttct   2520
tcccttcctt tctcgccacg ttcgccggct ttccccgtca gctctaaat cggggggctcc   2580 ctttagggtt ccgatttagt gctttacggc acctcgaccc caaaaaactt gattagggtg   2640
atggttcacg tagtgggcca tcgccctgat agacggtttt tcgccctttg acgttggagt   2700
ccacgttctt taatagtgga ctcttgttcc aaactggaac aacactcaac cctatctcgg   2760
tctattcttt tgatttataa gggattttgc cgatttcggc ctattggtta aaaaatgagc   2820
tgatttaaca aaaatttaac gcgaatttta acaaaatatt aacgcttaca atttccattc   2880
gccattcagg ctgcgcaact gttgggaagg gcgatcggtg cgggcctctt cgctattacg   2940
```

```
ccagctggcg aaaggggat gtgctgcaag gcgattaagt tgggtaacgc cagggttttc   3000
ccagtcacga cgttgtaaaa cgacggccag tgaattgtaa tacgactcac tatagggcga   3060
attgggtacc gggcccccc tcgaggtcga tggtgtcgat aagcttgata tcgaattcat   3120
gtcacacaaa ccgatcttcg cctcaaggaa acctaattct acatccgaga gactgccgag   3180
atccagtcta cactgattaa ttttcgggcc aataatttaa aaaatcgtg ttatataata   3240 ttatatgtat tatatatata catcatgatg atactgacag tcatgtccca ttgctaaata   3300
gacagactcc atctgccgcc tccaactgat gttctcaata tttaaggggt catctcgcat   3360
tgtttaataa taaacagact ccatctaccg cctccaaatg atgttctcaa aatatattgt   3420
atgaacttat ttttattact tagtattatt agacaactta cttgctttat gaaaaacact   3480
tcctatttag gaaacaattt ataatggcag ttcgttcatt taacaattta tgtagaataa   3540
atgttataaa tgcgtatggg aaatcttaaa tatggatagc ataaatgata tctgcattgc   3600
ctaattcgaa atcaacagca acgaaaaaaa tcccttgtac aacataaata gtcatcgaga   3660
aatatcaact atcaaagaac agctattcac acgttactat tgagattatt attggacgag   3720
aatcacacac tcaactgtct ttctctcttc tagaaataca ggtacaagta tgtactattc   3780
tcattgttca tacttctagt catttcatcc cacatattcc ttggatttct ctccaatgaa   3840
tgacattcta tcttgcaaat tcaacaatta taataagata taccaaagta gcggtatagt   3900
ggcaatcaaa aagcttctct ggtgtgcttc tcgtatttat ttttattcta atgatccatt   3960
aaaggtatat atttatttct tgttatataa tccttttgtt tattacatgg gctggataca   4020
taaaggtatt ttgatttaat tttttgctta aattcaatcc ccctcgttc agtgtcaact   4080 gtaatggtag gaaattacca tacttttgaa gaagcaaaaa aaatgaaaga aaaaaaaat   4140 cgtatttcca ggttagacgt tccgcagaat ctagaatgcg gtatgcggta cattgttctt   4200
cgaacgtaaa agttgcgctc cctgagatat tgtacatttt tgcttttaca agtacaagta   4260
catcgtacaa ctatgtacta ctgttgatgc atccacaaca gtttgttttg ttttttttg   4320 tttttttttt ttctaatgat tcattaccgc tatgtatacc tacttgtact tgtagtaagc   4380
cgggttattg gcgttcaatt aatcatagac ttatgaatct gcacggtgtg cgctgcgagt   4440
tacttttagc ttatgcatgc tacttgggtg taatattggg atctgttcgg aaatcaacgg   4500
atgctcaatc gatttcgaca gtaattaatt aagtcataca caagtcagct ttcttcgagc   4560
ctcatataag tataagtagt tcaacgtatt agcactgtac ccagcatctc cgtatcgaga   4620
aacacaacaa catgccccat tggacagatc atgcggatac acaggttgtg cagtatcata   4680
catactcgat cagacaggtc gtctgaccat catacaagct gaacaagcgc tccatacttg   4740
cacgctctct atatacacag ttaaattaca tatccatagt ctaacctcta acagttaatc   4800
ttctggtaag cctcccagcc agccttctgg tatcgcttgg cctcctcaat aggatctcgg   4860
ttctggccgt acagacctcg gccgacaatt atgatatccg ttccggtaga catgacatcc   4920
tcaacagttc ggtactgctg tccgagagcg tctcccttgt cgtcaagacc caccccgggg   4980
gtcagaataa gccagtcctc agagtcgccc ttaggtcggt tctgggcaat gaagccaacc   5040
acaaactcgg ggtcggatcg ggcaagctca atggtctgct tggagtactc gccagtggcc   5100
agagagccct tgcaagacag ctcggccagc atgagcagac ctctggccag cttctcgttg   5160
ggagagggga ctaggaactc cttgtactgg gagttctcgt agtcagagac gtcctccttc   5220
ttctgttcag agacagtttc ctcggcacca gctcgcaggc cagcaatgat tccggttccg   5280
ggtacaccgt gggcgttggt gatatcggac cactcggcga ttcggtgaca ccggtactgg   5340
```

```
tgcttgacag tgttgccaat atctgcgaac tttctgtcct cgaacaggaa gaaaccgtgc    5400
ttaagagcaa gttccttgag ggggagcaca gtgccggcgt aggtgaagtc gtcaatgatg    5460
tcgatatggg ttttgatcat gcacacataa ggtccgacct tatcggcaag ctcaatgagc    5520
tccttggtgg tggtaacatc cagagaagca cacaggttgg ttttcttggc tgccacgagc    5580
ttgagcactc gagcggcaaa ggcggacttg tggacgttag ctcgagcttc gtaggagggc    5640
attttggtgg tgaagaggag actgaaataa atttagtctg cagaactttt tatcggaacc    5700
ttatctgggg cagtgaagta tatgttatgg taatagttac gagttagttg aacttataga    5760
tagactggac tatacggcta tcggtccaaa ttagaaagaa cgtcaatggc tctctgggcg    5820 tcgccttttgc cgacaaaaat gtgatcatga tgaaagccag caatgacgtt gcagctgata    5880
ttgttgtcgg ccaaccgcgc cgaaaacgca gctgtcagac ccacagcctc caacgaagaa    5940
tgtatcgtca aagtgatcca agcacactca tagttggagt cgtactccaa aggcggcaat    6000
gacgagtcag acagatactc gtcgactcag gcgacgacga aattcctgca gcccatctgc    6060
agaattcagg agagaccggg ttggcggcgt atttgtgtcc caaaaaacag ccccaattgc    6120
cccgagaaag acgccaggc cgcctagatg acaaattcaa caactcacag ctgactttct    6180
gccattgcca ctagggggg gccttttat atggccaagc caagctctcc acgtcggttg    6240
ggctgcaccc aacaataaat gggtagggtt gcaccaacaa agggatggga tgggggtag    6300 aagatacgag gataacgggg ctcaatggca caaataagaa cgaatactgc cattaagact    6360
cgtgatccga cgactgacac cattgcatca tctaagggcc tcaaaactac ctcggaactg    6420
ctgcgctgat ctggacacca cagaggttcc gagcacttta ggttgcacca aatgtcccac    6480
caggtgcagg cagaaaacgc tggaacagcg tgtacagttt gtcttaacaa aaagtgaggg    6540
cgctgaggtc gagcagggtg gtgtgacttg ttatagcctt tagagctgcg aaagcgcgta    6600
tggatttggc tcatcaggcc agattgaggg tctgtggaca catgtcatgt tagtgtactt    6660
caatcgcccc ctggatatag ccccgacaat aggccgtggc ctcattttt tgccttccgc    6720 acatttccat tgctcggtac ccacacccttg cttctcctgc acttgccaac cttaatactg    6780
gtttacattg accaacatct tacaagcggg gggcttgtct agggtatata taaacagtgg    6840
ctctcccaat cggttgccag tctctttttt cctttctttc cccacagatt cgaaatctaa    6900
actacacatc acacaatgcc tgttactgac gtccttaagc gaaagtccgg tgtcatcgtc    6960
ggcgacgatg tccgagccgt gagtatccac gacaagatca gtgtcgagac gacgcgtttt    7020
gtgtaatgac acaatccgaa agtcgctagc aacacacact ctctacacaa actaacccag    7080
ctctccatgg ctctctcccct tactaccgag cagctgctcg agcgacccga cctggttgcc    7140
atcgacggca ttctctacga tctggaaggt cttgccaagg tccatcccgg aggcgacttg    7200
atcctcgctt ctggtgcctc cgatgcttct cctctgttct actccatgca cccttacgtc    7260
aagcccgaga actcgaagct gcttcaacag ttcgtgcgag gcaagcacga ccgaacctcc    7320
aaggacattg tctacacccta cgactctccc tttgcacagg acgtcaagcg aactatgcga    7380
gaggtcatga aaggtcggaa ctggtatgcc acacctggat tctggctgcg aaccgttggc    7440
atcattgctg tcaccgcctt ttgcgagtgg cactgggcta ctaccggaat ggtgctgtgg    7500
ggtctcttga ctggattcat gcacatgcag atcggcctgt ccattcagca cgatgcctct    7560
catggtgcca tcagcaaaaa gccctgggtc aacgctctct ttgcctacgg catcgacgtc    7620
attggatcgt ccagatggat ctggctgcag tctcacatca tgcgacatca cacctacacc    7680
aatcagcatg gtctcgacct ggatgccgag tccgcagaac cattccttgt gttccacaac    7740
```

```
taccctgctg ccaacactgc tcgaaagtgg tttcaccgat tccaggcctg gtacatgtac     7800
ctcgtgcttg agcctacgg cgtttcgctg gtgtacaacc ctctctacat cttccgaatg      7860
cagcacaacg acaccattcc cgagtctgtc acagccatgc gagagaacgg ctttctgcga     7920
cggtaccgaa cccttgcatt cgttatgcga gctttcttca tctttcgaac cgccttcttg    7980
ccctggtatc tcactggaac ctccctgctc atcaccattc ctctggtgcc cactgctacc    8040
ggtgccttcc tcaccttctt tttcatcttg tctcacaact tcgatggctc ggagcgaatc    8100
cccgacaaga actgcaaggt caagagctcc gagaaggacg ttgaagccga tcagatcgac    8160
tggtacagag ctcaggtgga gacctcttcc acctacggtg gacccattgc catgttcttt    8220
actggcggtc tcaacttcca gatcgagcat cacctctttc ctcgaatgtc gtcttggcac    8280
tatcccttcg tgcagcaagc tgtccgagag tgttgcgaac gacacggagt tcggtacgtc    8340
ttctacccta ccattgtggg caacatcatt tccacccctca agtacatgca caaagtcggt   8400
gtggttcact gtgtcaagga cgctcaggat tcctaagc                            8438
```

<210> SEQ ID NO 20
<211> LENGTH: 37
<212> TYPE: DNA
<213> ORGANISM: Artificial Sequence
<220> FEATURE:
<223> OTHER INFORMATION: Primer Eg5P1A.HaGG

<400> SEQUENCE: 20
gtcttgccaa ggtccatgcc ggaggcgact tgatcct     37

<210> SEQ ID NO 21
<211> LENGTH: 37
<212> TYPE: DNA
<213> ORGANISM: Artificial Sequence
<220> FEATURE:
<223> OTHER INFORMATION: Primer Eg5P1B.HaGG

<400> SEQUENCE: 21
aggatcaagt cgcctccggc atggaccttg gcaagac     37

<210> SEQ ID NO 22
<211> LENGTH: 37
<212> TYPE: DNA
<213> ORGANISM: Artificial Sequence
<220> FEATURE:
<223> OTHER INFORMATION: Primer Eg5P2A.HrGG

<400> SEQUENCE: 22
gtcttgccaa ggtccatcga ggaggcgact tgatcct     37

<210> SEQ ID NO 23
<211> LENGTH: 37
<212> TYPE: DNA
<213> ORGANISM: Artificial Sequence
<220> FEATURE:
<223> OTHER INFORMATION: Primer Eg5P2B.HrGG

<400> SEQUENCE: 23
aggatcaagt cgcctcctcg atggaccttg gcaagac     37

<210> SEQ ID NO 24
<211> LENGTH: 37
<212> TYPE: DNA
<213> ORGANISM: Artificial Sequence
<220> FEATURE:
<223> OTHER INFORMATION: Primer Eg5P3A.HnGG

```
<400> SEQUENCE: 24
gtcttgccaa ggtccataac ggaggcgact tgatcct                                37

<210> SEQ ID NO 25
<211> LENGTH: 37
<212> TYPE: DNA
<213> ORGANISM: Artificial Sequence
<220> FEATURE:
<223> OTHER INFORMATION: Primer Eg5P3B.HnGG

<400> SEQUENCE: 25
aggatcaagt cgcctccgtt atggaccttg gcaagac                                37

<210> SEQ ID NO 26
<211> LENGTH: 37
<212> TYPE: DNA
<213> ORGANISM: Artificial Sequence
<220> FEATURE:
<223> OTHER INFORMATION: Primer Eg5P4A.HdGG

<400> SEQUENCE: 26
gtcttgccaa ggtccatgac ggaggcgact tgatcct                                37

<210> SEQ ID NO 27
<211> LENGTH: 37
<212> TYPE: DNA
<213> ORGANISM: Artificial Sequence
<220> FEATURE:
<223> OTHER INFORMATION: Primer Eg5P4B.HdGG

<400> SEQUENCE: 27
aggatcaagt cgcctccgtc atggaccttg gcaagac                                37

<210> SEQ ID NO 28
<211> LENGTH: 37
<212> TYPE: DNA
<213> ORGANISM: Artificial Sequence
<220> FEATURE:
<223> OTHER INFORMATION: Primer Eg5P5A.HcGG

<400> SEQUENCE: 28
gtcttgccaa ggtccattgc ggaggcgact tgatcct                                37

<210> SEQ ID NO 29
<211> LENGTH: 37
<212> TYPE: DNA
<213> ORGANISM: Artificial Sequence
<220> FEATURE:
<223> OTHER INFORMATION: Primer Eg5P5B.HcGG

<400> SEQUENCE: 29
aggatcaagt cgcctccgca atggaccttg gcaagac                                37

<210> SEQ ID NO 30
<211> LENGTH: 37
<212> TYPE: DNA
<213> ORGANISM: Artificial Sequence
<220> FEATURE:
<223> OTHER INFORMATION: Primer Eg5P6A.HqGG

<400> SEQUENCE: 30
gtcttgccaa ggtccatcag ggaggcgact tgatcct                                37

<210> SEQ ID NO 31
<211> LENGTH: 37
```

```
<212> TYPE: DNA
<213> ORGANISM: Artificial Sequence
<220> FEATURE:
<223> OTHER INFORMATION: Primer Eg5P6B.HqGG

<400> SEQUENCE: 31
aggatcaagt cgcctccctg atggaccttg gcaagac                              37

<210> SEQ ID NO 32
<211> LENGTH: 37
<212> TYPE: DNA
<213> ORGANISM: Artificial Sequence
<220> FEATURE:
<223> OTHER INFORMATION: Primer Eg5P7A.HeGG

<400> SEQUENCE: 32
gtcttgccaa ggtccatgag ggaggcgact tgatcct                              37

<210> SEQ ID NO 33
<211> LENGTH: 37
<212> TYPE: DNA
<213> ORGANISM: Artificial Sequence
<220> FEATURE:
<223> OTHER INFORMATION: Primer Eg5P7B.HeGG

<400> SEQUENCE: 33
aggatcaagt cgcctccctc atggaccttg gcaagac                              37

<210> SEQ ID NO 34
<211> LENGTH: 37
<212> TYPE: DNA
<213> ORGANISM: Artificial Sequence
<220> FEATURE:
<223> OTHER INFORMATION: Primer Eg5P8A.HgGG

<400> SEQUENCE: 34
gtcttgccaa ggtccatggt ggaggcgact tgatcct                              37

<210> SEQ ID NO 35
<211> LENGTH: 37
<212> TYPE: DNA
<213> ORGANISM: Artificial Sequence
<220> FEATURE:
<223> OTHER INFORMATION: Primer Eg5P8B.HgGG

<400> SEQUENCE: 35
aggatcaagt cgcctccacc atggaccttg gcaagac                              37

<210> SEQ ID NO 36
<211> LENGTH: 37
<212> TYPE: DNA
<213> ORGANISM: Artificial Sequence
<220> FEATURE:
<223> OTHER INFORMATION: Primer Eg5P9A.HhGG

<400> SEQUENCE: 36
gtcttgccaa ggtccatcac ggaggcgact tgatcct                              37

<210> SEQ ID NO 37
<211> LENGTH: 37
<212> TYPE: DNA
<213> ORGANISM: Artificial Sequence
<220> FEATURE:
<223> OTHER INFORMATION: Primer Eg5P9B.HhGG

<400> SEQUENCE: 37
aggatcaagt cgcctccgtg atggaccttg gcaagac                              37
```

```
<210> SEQ ID NO 38
<211> LENGTH: 37
<212> TYPE: DNA
<213> ORGANISM: Artificial Sequence
<220> FEATURE:
<223> OTHER INFORMATION: Primer Eg5P10A.HiGG

<400> SEQUENCE: 38
gtcttgccaa ggtccatatc ggaggcgact tgatcct                               37

<210> SEQ ID NO 39
<211> LENGTH: 37
<212> TYPE: DNA
<213> ORGANISM: Artificial Sequence
<220> FEATURE:
<223> OTHER INFORMATION: Primer Eg5P10B.HiGG

<400> SEQUENCE: 39
aggatcaagt cgcctccgat atggaccttg gcaagac                               37

<210> SEQ ID NO 40
<211> LENGTH: 37
<212> TYPE: DNA
<213> ORGANISM: Artificial Sequence
<220> FEATURE:
<223> OTHER INFORMATION: Primer Eg5P11A.HlGG

<400> SEQUENCE: 40
gtcttgccaa ggtccatctg ggaggcgact tgatcct                               37

<210> SEQ ID NO 41
<211> LENGTH: 37
<212> TYPE: DNA
<213> ORGANISM: Artificial Sequence
<220> FEATURE:
<223> OTHER INFORMATION: Primer Eg5P11B.HlGG

<400> SEQUENCE: 41
aggatcaagt cgcctcccag atggaccttg gcaagac                               37

<210> SEQ ID NO 42
<211> LENGTH: 37
<212> TYPE: DNA
<213> ORGANISM: Artificial Sequence
<220> FEATURE:
<223> OTHER INFORMATION: Primer Eg5P12A.HkGG

<400> SEQUENCE: 42
gtcttgccaa ggtccataag ggaggcgact tgatcct                               37

<210> SEQ ID NO 43
<211> LENGTH: 37
<212> TYPE: DNA
<213> ORGANISM: Artificial Sequence
<220> FEATURE:
<223> OTHER INFORMATION: Primer Eg5P12B.HkGG

<400> SEQUENCE: 43
aggatcaagt cgcctccctt atggaccttg gcaagac                               37

<210> SEQ ID NO 44
<211> LENGTH: 37
<212> TYPE: DNA
<213> ORGANISM: Artificial Sequence
<220> FEATURE:
<223> OTHER INFORMATION: Primer Eg5P13A.HmGG
```

```
<400> SEQUENCE: 44
gtcttgccaa ggtccatatg ggaggcgact tgatcct                              37

<210> SEQ ID NO 45
<211> LENGTH: 37
<212> TYPE: DNA
<213> ORGANISM: Artificial Sequence
<220> FEATURE:
<223> OTHER INFORMATION: Primer Eg5P13B.HmGG

<400> SEQUENCE: 45
aggatcaagt cgcctcccat atggaccttg gcaagac                              37

<210> SEQ ID NO 46
<211> LENGTH: 37
<212> TYPE: DNA
<213> ORGANISM: Artificial Sequence
<220> FEATURE:
<223> OTHER INFORMATION: Primer Eg5P14A.HfGG

<400> SEQUENCE: 46
gtcttgccaa ggtccatttc ggaggcgact tgatcct                              37

<210> SEQ ID NO 47
<211> LENGTH: 37
<212> TYPE: DNA
<213> ORGANISM: Artificial Sequence
<220> FEATURE:
<223> OTHER INFORMATION: Primer Eg5P14B.HfGG

<400> SEQUENCE: 47
aggatcaagt cgcctccgaa atggaccttg gcaagac                              37

<210> SEQ ID NO 48
<211> LENGTH: 37
<212> TYPE: DNA
<213> ORGANISM: Artificial Sequence
<220> FEATURE:
<223> OTHER INFORMATION: Primer Eg5P15A.HsGG

<400> SEQUENCE: 48
gtcttgccaa ggtccattcc ggaggcgact tgatcct                              37

<210> SEQ ID NO 49
<211> LENGTH: 37
<212> TYPE: DNA
<213> ORGANISM: Artificial Sequence
<220> FEATURE:
<223> OTHER INFORMATION: Primer Eg5P15B.HsGG

<400> SEQUENCE: 49
aggatcaagt cgcctccgga atggaccttg gcaagac                              37

<210> SEQ ID NO 50
<211> LENGTH: 37
<212> TYPE: DNA
<213> ORGANISM: Artificial Sequence
<220> FEATURE:
<223> OTHER INFORMATION: Primer Eg5P16A.HtGG

<400> SEQUENCE: 50
gtcttgccaa ggtccatacc ggaggcgact tgatcct                              37

<210> SEQ ID NO 51
<211> LENGTH: 37
```

```
<212> TYPE: DNA
<213> ORGANISM: Artificial Sequence
<220> FEATURE:
<223> OTHER INFORMATION: Primer Eg5P16B.HtGG

<400> SEQUENCE: 51
aggatcaagt cgcctccggt atggaccttg gcaagac                              37

<210> SEQ ID NO 52
<211> LENGTH: 37
<212> TYPE: DNA
<213> ORGANISM: Artificial Sequence
<220> FEATURE:
<223> OTHER INFORMATION: Primer Eg5P17A.HwGG

<400> SEQUENCE: 52
gtcttgccaa ggtccattgg ggaggcgact tgatcct                              37

<210> SEQ ID NO 53
<211> LENGTH: 37
<212> TYPE: DNA
<213> ORGANISM: Artificial Sequence
<220> FEATURE:
<223> OTHER INFORMATION: Primer Eg5P17B.HwGG

<400> SEQUENCE: 53
aggatcaagt cgcctcccca atggaccttg gcaagac                              37

<210> SEQ ID NO 54
<211> LENGTH: 37
<212> TYPE: DNA
<213> ORGANISM: Artificial Sequence
<220> FEATURE:
<223> OTHER INFORMATION: Primer Eg5P18A.HyGG

<400> SEQUENCE: 54
gtcttgccaa ggtccattac ggaggcgact tgatcct                              37

<210> SEQ ID NO 55
<211> LENGTH: 37
<212> TYPE: DNA
<213> ORGANISM: Artificial Sequence
<220> FEATURE:
<223> OTHER INFORMATION: Primer Eg5P18B.HyGG

<400> SEQUENCE: 55
aggatcaagt cgcctccgta atggaccttg gcaagac                              37

<210> SEQ ID NO 56
<211> LENGTH: 37
<212> TYPE: DNA
<213> ORGANISM: Artificial Sequence
<220> FEATURE:
<223> OTHER INFORMATION: Primer Eg5P19A.HvGG

<400> SEQUENCE: 56
gtcttgccaa ggtccatgtc ggaggcgact tgatcct                              37

<210> SEQ ID NO 57
<211> LENGTH: 37
<212> TYPE: DNA
<213> ORGANISM: Artificial Sequence
<220> FEATURE:
<223> OTHER INFORMATION: Primer Eg5P19B.HvGG

<400> SEQUENCE: 57
aggatcaagt cgcctccgac atggaccttg gcaagac                              37
```

<210> SEQ ID NO 58
<211> LENGTH: 449
<212> TYPE: PRT
<213> ORGANISM: Euglena gracilis
<220> FEATURE:
<221> NAME/KEY: MISC_FEATURE
<222> LOCATION: (34)..(34)
<223> OTHER INFORMATION: Xaa = Gly (G) or His (H)

<400> SEQUENCE: 58

```
Met Ala Leu Ser Leu Thr Thr Glu Gln Leu Leu Glu Arg Pro Asp Leu
1               5                   10                  15

Val Ala Ile Asp Gly Ile Leu Tyr Asp Leu Glu Gly Leu Ala Lys Val
            20                  25                  30

His Xaa Gly Gly Asp Leu Ile Leu Ala Ser Gly Ala Ser Asp Ala Ser
        35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
        115                 120                 125

His Trp Ala Thr Thr Gly Met Val Leu Trp Gly Leu Leu Thr Gly Phe
    130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
        195                 200                 205

Ser Ala Glu Pro Phe Leu Val Phe His Asn Tyr Pro Ala Ala Asn Thr
    210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
        275                 280                 285

Ala Phe Phe Ile Phe Arg Thr Ala Phe Leu Pro Trp Tyr Leu Thr Gly
    290                 295                 300

Thr Ser Leu Leu Ile Thr Ile Pro Leu Val Pro Ala Thr Gly Ala
305                 310                 315                 320

Phe Leu Thr Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
```

```
                355               360              365
Thr Tyr Gly Gly Pro Ile Ala Met Phe Phe Thr Gly Gly Leu Asn Phe
    370             375             380

Gln Ile Glu His His Leu Phe Pro Arg Met Ser Ser Trp His Tyr Pro
385             390             395             400

Phe Val Gln Gln Ala Val Arg Glu Cys Cys Glu Arg His Gly Val Arg
            405             410             415

Tyr Val Phe Tyr Pro Thr Ile Val Gly Asn Ile Ile Ser Thr Leu Lys
        420             425             430

Tyr Met His Lys Val Gly Val Val His Cys Val Lys Asp Ala Gln Asp
        435             440             445

Ser

<210> SEQ ID NO 59
<211> LENGTH: 33
<212> TYPE: DNA
<213> ORGANISM: Artificial Sequence
<220> FEATURE:
<223> OTHER INFORMATION: Primer Eg5-18A.HPGA

<400> SEQUENCE: 59
aaggtccatc ccggagccga cttgatcctc gct                              33

<210> SEQ ID NO 60
<211> LENGTH: 33
<212> TYPE: DNA
<213> ORGANISM: Artificial Sequence
<220> FEATURE:
<223> OTHER INFORMATION: Primer Eg5-18B.HPGA

<400> SEQUENCE: 60
agcgaggatc aagtcggctc cgggatggac ctt                              33

<210> SEQ ID NO 61
<211> LENGTH: 33
<212> TYPE: DNA
<213> ORGANISM: Artificial Sequence
<220> FEATURE:
<223> OTHER INFORMATION: Primer Eg5-1A.HPGR

<400> SEQUENCE: 61
aaggtccatc ccggacgaga cttgatcctc gct                              33

<210> SEQ ID NO 62
<211> LENGTH: 33
<212> TYPE: DNA
<213> ORGANISM: Artificial Sequence
<220> FEATURE:
<223> OTHER INFORMATION: Primer Eg5-1B.HPGR

<400> SEQUENCE: 62
agcgaggatc aagtctcgtc cgggatggac ctt                              33

<210> SEQ ID NO 63
<211> LENGTH: 33
<212> TYPE: DNA
<213> ORGANISM: Artificial Sequence
<220> FEATURE:
<223> OTHER INFORMATION: Primer Eg5-2A.HPGN

<400> SEQUENCE: 63
aaggtccatc ccggaaacga cttgatcctc gct                              33
```

<210> SEQ ID NO 64
<211> LENGTH: 33
<212> TYPE: DNA
<213> ORGANISM: Artificial Sequence
<220> FEATURE:
<223> OTHER INFORMATION: Primer Eg5-2B.HPGN

<400> SEQUENCE: 64
agcgaggatc aagtcgtttc cgggatggac ctt                                33

<210> SEQ ID NO 65
<211> LENGTH: 33
<212> TYPE: DNA
<213> ORGANISM: Artificial Sequence
<220> FEATURE:
<223> OTHER INFORMATION: Primer Eg5-3A.HPGD

<400> SEQUENCE: 65
aaggtccatc ccggagacga cttgatcctc gct                                33

<210> SEQ ID NO 66
<211> LENGTH: 33
<212> TYPE: DNA
<213> ORGANISM: Artificial Sequence
<220> FEATURE:
<223> OTHER INFORMATION: Primer Eg5-3B.HPGD

<400> SEQUENCE: 66
agcgaggatc aagtcgtctc cgggatggac ctt                                33

<210> SEQ ID NO 67
<211> LENGTH: 33
<212> TYPE: DNA
<213> ORGANISM: Artificial Sequence
<220> FEATURE:
<223> OTHER INFORMATION: Primer Eg5-4A.HPGC

<400> SEQUENCE: 67
aaggtccatc ccggatgcga cttgatcctc gct                                33

<210> SEQ ID NO 68
<211> LENGTH: 33
<212> TYPE: DNA
<213> ORGANISM: Artificial Sequence
<220> FEATURE:
<223> OTHER INFORMATION: Primer Eg5-4B.HPGC

<400> SEQUENCE: 68
agcgaggatc aagtcgcatc cgggatggac ctt                                33

<210> SEQ ID NO 69
<211> LENGTH: 33
<212> TYPE: DNA
<213> ORGANISM: Artificial Sequence
<220> FEATURE:
<223> OTHER INFORMATION: Primer Eg5-5A.HPGQ

<400> SEQUENCE: 69
aaggtccatc ccggacagga cttgatcctc gct                                33

<210> SEQ ID NO 70
<211> LENGTH: 33
<212> TYPE: DNA
<213> ORGANISM: Artificial Sequence
<220> FEATURE:
<223> OTHER INFORMATION: Primer Eg5-5B.HPGQ

<400> SEQUENCE: 70
agcgaggatc aagtcctgtc cgggatggac ctt                                    33

<210> SEQ ID NO 71
<211> LENGTH: 33
<212> TYPE: DNA
<213> ORGANISM: Artificial Sequence
<220> FEATURE:
<223> OTHER INFORMATION: Primer Eg5-19A.HPGE

<400> SEQUENCE: 71
aaggtccatc ccggagagga cttgatcctc gct                                    33

<210> SEQ ID NO 72
<211> LENGTH: 33
<212> TYPE: DNA
<213> ORGANISM: Artificial Sequence
<220> FEATURE:
<223> OTHER INFORMATION: Primer Eg5-19B.HPGE

<400> SEQUENCE: 72
agcgaggatc aagtcctctc cgggatggac ctt                                    33

<210> SEQ ID NO 73
<211> LENGTH: 33
<212> TYPE: DNA
<213> ORGANISM: Artificial Sequence
<220> FEATURE:
<223> OTHER INFORMATION: Primer Eg5-6A.HPGH

<400> SEQUENCE: 73
aaggtccatc ccggacacga cttgatcctc gct                                    33

<210> SEQ ID NO 74
<211> LENGTH: 33
<212> TYPE: DNA
<213> ORGANISM: Artificial Sequence
<220> FEATURE:
<223> OTHER INFORMATION: Primer Eg5-6B.HPGH

<400> SEQUENCE: 74
agcgaggatc aagtcgtgtc cgggatggac ctt                                    33

<210> SEQ ID NO 75
<211> LENGTH: 33
<212> TYPE: DNA
<213> ORGANISM: Artificial Sequence
<220> FEATURE:
<223> OTHER INFORMATION: Primer Eg5-7A.HPGI

<400> SEQUENCE: 75
aaggtccatc ccggaatcga cttgatcctc gct                                    33

<210> SEQ ID NO 76
<211> LENGTH: 33
<212> TYPE: DNA
<213> ORGANISM: Artificial Sequence
<220> FEATURE:
<223> OTHER INFORMATION: Primer Eg5-7B.HPGI

<400> SEQUENCE: 76
agcgaggatc aagtcgattc cgggatggac ctt                                    33

<210> SEQ ID NO 77
<211> LENGTH: 33
<212> TYPE: DNA
<213> ORGANISM: Artificial Sequence

```
<220> FEATURE:
<223> OTHER INFORMATION: Primer Eg5-8A.HPGL

<400> SEQUENCE: 77
aaggtccatc ccggactgga cttgatcctc gct                                33

<210> SEQ ID NO 78
<211> LENGTH: 33
<212> TYPE: DNA
<213> ORGANISM: Artificial Sequence
<220> FEATURE:
<223> OTHER INFORMATION: Primer Eg5-8B.HPGL

<400> SEQUENCE: 78
agcgaggatc aagtccagtc cgggatggac ctt                                33

<210> SEQ ID NO 79
<211> LENGTH: 33
<212> TYPE: DNA
<213> ORGANISM: Artificial Sequence
<220> FEATURE:
<223> OTHER INFORMATION: Primer Eg5-9A.HPGK

<400> SEQUENCE: 79
aaggtccatc ccggaaaaga cttgatcctc gct                                33

<210> SEQ ID NO 80
<211> LENGTH: 33
<212> TYPE: DNA
<213> ORGANISM: Artificial Sequence
<220> FEATURE:
<223> OTHER INFORMATION: Primer Eg5-9B.HPGK

<400> SEQUENCE: 80
agcgaggatc aagtcttttc cgggatggac ctt                                33

<210> SEQ ID NO 81
<211> LENGTH: 33
<212> TYPE: DNA
<213> ORGANISM: Artificial Sequence
<220> FEATURE:
<223> OTHER INFORMATION: Primer Eg5-10A.HPGM

<400> SEQUENCE: 81
aaggtccatc ccggaatgga cttgatcctc gct                                33

<210> SEQ ID NO 82
<211> LENGTH: 33
<212> TYPE: DNA
<213> ORGANISM: Artificial Sequence
<220> FEATURE:
<223> OTHER INFORMATION: Primer Eg5-10B.HPGM

<400> SEQUENCE: 82
agcgaggatc aagtccattc cgggatggac ctt                                33

<210> SEQ ID NO 83
<211> LENGTH: 33
<212> TYPE: DNA
<213> ORGANISM: Artificial Sequence
<220> FEATURE:
<223> OTHER INFORMATION: Primer Eg5-11A.HPGF

<400> SEQUENCE: 83
aaggtccatc ccggattcga cttgatcctc gct                                33
```

```
<210> SEQ ID NO 84
<211> LENGTH: 33
<212> TYPE: DNA
<213> ORGANISM: Artificial Sequence
<220> FEATURE:
<223> OTHER INFORMATION: Primer Eg5-11B.HPGF

<400> SEQUENCE: 84
agcgaggatc aagtcgaatc cgggatggac ctt                              33

<210> SEQ ID NO 85
<211> LENGTH: 33
<212> TYPE: DNA
<213> ORGANISM: Artificial Sequence
<220> FEATURE:
<223> OTHER INFORMATION: Primer Eg5-12A.HPGP

<400> SEQUENCE: 85
aaggtccatc ccggacccga cttgatcctc gct                              33

<210> SEQ ID NO 86
<211> LENGTH: 33
<212> TYPE: DNA
<213> ORGANISM: Artificial Sequence
<220> FEATURE:
<223> OTHER INFORMATION: Primer Eg5-12B.HPGP

<400> SEQUENCE: 86
agcgaggatc aagtcgggtc cgggatggac ctt                              33

<210> SEQ ID NO 87
<211> LENGTH: 33
<212> TYPE: DNA
<213> ORGANISM: Artificial Sequence
<220> FEATURE:
<223> OTHER INFORMATION: Primer Eg5-13A.HPGS

<400> SEQUENCE: 87
aaggtccatc ccggatccga cttgatcctc gct                              33

<210> SEQ ID NO 88
<211> LENGTH: 33
<212> TYPE: DNA
<213> ORGANISM: Artificial Sequence
<220> FEATURE:
<223> OTHER INFORMATION: Primer Eg5-13B.HPGS

<400> SEQUENCE: 88
agcgaggatc aagtcggatc cgggatggac ctt                              33

<210> SEQ ID NO 89
<211> LENGTH: 33
<212> TYPE: DNA
<213> ORGANISM: Artificial Sequence
<220> FEATURE:
<223> OTHER INFORMATION: Primer Eg5-14A.HPGT

<400> SEQUENCE: 89
aaggtccatc ccggaaccga cttgatcctc gct                              33

<210> SEQ ID NO 90
<211> LENGTH: 33
<212> TYPE: DNA
<213> ORGANISM: Artificial Sequence
<220> FEATURE:
<223> OTHER INFORMATION: Primer Eg5-14B.HPGT

<400> SEQUENCE: 90
```
agcgaggatc aagtcggttc cgggatggac ctt                                          33

<210> SEQ ID NO 91
<211> LENGTH: 33
<212> TYPE: DNA
<213> ORGANISM: Artificial Sequence
<220> FEATURE:
<223> OTHER INFORMATION: Primer Eg5-15A.HPGW

<400> SEQUENCE: 91
aaggtccatc ccggatggga cttgatcctc gct                                          33

<210> SEQ ID NO 92
<211> LENGTH: 33
<212> TYPE: DNA
<213> ORGANISM: Artificial Sequence
<220> FEATURE:
<223> OTHER INFORMATION: Primer Eg5-15B.HPGW

<400> SEQUENCE: 92
agcgaggatc aagtcccatc cgggatggac ctt                                          33

<210> SEQ ID NO 93
<211> LENGTH: 33
<212> TYPE: DNA
<213> ORGANISM: Artificial Sequence
<220> FEATURE:
<223> OTHER INFORMATION: Primer Eg5-16A.HPGY

<400> SEQUENCE: 93
aaggtccatc ccggatacga cttgatcctc gct                                          33

<210> SEQ ID NO 94
<211> LENGTH: 33
<212> TYPE: DNA
<213> ORGANISM: Artificial Sequence
<220> FEATURE:
<223> OTHER INFORMATION: Primer Eg5-16B.HPGY

<400> SEQUENCE: 94
agcgaggatc aagtcgtatc cgggatggac ctt                                          33

<210> SEQ ID NO 95
<211> LENGTH: 33
<212> TYPE: DNA
<213> ORGANISM: Artificial Sequence
<220> FEATURE:
<223> OTHER INFORMATION: Primer Eg5-17A.HPGV

<400> SEQUENCE: 95
aaggtccatc ccggagtcga cttgatcctc gct                                          33

<210> SEQ ID NO 96
<211> LENGTH: 33
<212> TYPE: DNA
<213> ORGANISM: Artificial Sequence
<220> FEATURE:
<223> OTHER INFORMATION: Primer Eg5-17B.HPGV

<400> SEQUENCE: 96
agcgaggatc aagtcgactc cgggatggac ctt                                          33

<210> SEQ ID NO 97
<211> LENGTH: 449
<212> TYPE: PRT
<213> ORGANISM: Euglena gracilis

<400> SEQUENCE: 97

```
Met Ala Leu Ser Leu Thr Thr Glu Gln Leu Glu Arg Pro Asp Leu
1               5                   10                  15

Val Ala Ile Asp Gly Ile Leu Tyr Asp Leu Glu Gly Leu Ala Lys Val
            20                  25                  30

His Pro Gly Ser Asp Leu Ile Leu Ala Ser Gly Ala Ser Asp Ala Ser
                35                  40                  45

Pro Leu Phe Tyr Ser Met His Pro Tyr Val Lys Pro Glu Asn Ser Lys
    50                  55                  60

Leu Leu Gln Gln Phe Val Arg Gly Lys His Asp Arg Thr Ser Lys Asp
65                  70                  75                  80

Ile Val Tyr Thr Tyr Asp Ser Pro Phe Ala Gln Asp Val Lys Arg Thr
                85                  90                  95

Met Arg Glu Val Met Lys Gly Arg Asn Trp Tyr Ala Thr Pro Gly Phe
            100                 105                 110

Trp Leu Arg Thr Val Gly Ile Ile Ala Val Thr Ala Phe Cys Glu Trp
            115                 120                 125

His Trp Ala Thr Thr Gly Met Val Leu Trp Gly Leu Leu Thr Gly Phe
            130                 135                 140

Met His Met Gln Ile Gly Leu Ser Ile Gln His Asp Ala Ser His Gly
145                 150                 155                 160

Ala Ile Ser Lys Lys Pro Trp Val Asn Ala Leu Phe Ala Tyr Gly Ile
                165                 170                 175

Asp Val Ile Gly Ser Ser Arg Trp Ile Trp Leu Gln Ser His Ile Met
            180                 185                 190

Arg His His Thr Tyr Thr Asn Gln His Gly Leu Asp Leu Asp Ala Glu
            195                 200                 205

Ser Ala Glu Pro Phe Leu Val Phe His Asn Tyr Pro Ala Ala Asn Thr
210                 215                 220

Ala Arg Lys Trp Phe His Arg Phe Gln Ala Trp Tyr Met Tyr Leu Val
225                 230                 235                 240

Leu Gly Ala Tyr Gly Val Ser Leu Val Tyr Asn Pro Leu Tyr Ile Phe
                245                 250                 255

Arg Met Gln His Asn Asp Thr Ile Pro Glu Ser Val Thr Ala Met Arg
            260                 265                 270

Glu Asn Gly Phe Leu Arg Arg Tyr Arg Thr Leu Ala Phe Val Met Arg
            275                 280                 285

Ala Phe Phe Ile Phe Arg Thr Ala Phe Leu Pro Trp Tyr Leu Thr Gly
            290                 295                 300

Thr Ser Leu Leu Ile Thr Ile Pro Leu Val Pro Thr Ala Thr Gly Ala
305                 310                 315                 320

Phe Leu Thr Phe Phe Ile Leu Ser His Asn Phe Asp Gly Ser Glu
                325                 330                 335

Arg Ile Pro Asp Lys Asn Cys Lys Val Lys Ser Ser Glu Lys Asp Val
            340                 345                 350

Glu Ala Asp Gln Ile Asp Trp Tyr Arg Ala Gln Val Glu Thr Ser Ser
            355                 360                 365

Thr Tyr Gly Gly Pro Ile Ala Met Phe Phe Thr Gly Gly Leu Asn Phe
    370                 375                 380

Gln Ile Glu His His Leu Phe Pro Arg Met Ser Ser Trp His Tyr Pro
385                 390                 395                 400

Phe Val Gln Gln Ala Val Arg Glu Cys Cys Glu Arg His Gly Val Arg
                405                 410                 415
```

Tyr Val Phe Tyr Pro Thr Ile Val Gly Asn Ile Ile Ser Thr Leu Lys
        420                 425                 430

Tyr Met His Lys Val Gly Val Val His Cys Val Lys Asp Ala Gln Asp
        435                 440                 445

Ser

<210> SEQ ID NO 98
<211> LENGTH: 8357
<212> TYPE: DNA
<213> ORGANISM: Artificial Sequence
<220> FEATURE:
<223> OTHER INFORMATION: Plasmid pZUFmEaD5S

<400> SEQUENCE: 98

| | |
|---|---|
| catggccacc atctccctga ctaccgagca gctcctggaa caccccgagc tcgttgccat | 60 |
| cgacggagtc ctgtacgatc tcttcggtct ggccaaggtg catccaggag gcaacctcat | 120 |
| cgaagctgcc ggtgcatccg acggaaccgc tctgttctac tccatgcatc ctggagtcaa | 180 |
| gccagagaac tcgaagcttc tgcagcaatt tgcccgaggc aagcacgaac gaagctccaa | 240 |
| ggatcccgtg tacaccttcg actctccctt tgctcaggac gtcaagcagt ccgttcgaga | 300 |
| ggtcatgaag ggtcgaaact ggtacgccac tcctggcttc tggctgagaa ccgcactcat | 360 |
| catcgcttgt actgccattg gcgagtggta ctggatcaca accggagcag tgatgtgggg | 420 |
| tatctttact ggatacttcc actcgcagat tggcttggcc attcaacacg atgcttctca | 480 |
| cggagccatc agcaaaaagc cctgggtcaa cgccttttc gcttatggca tcgacgccat | 540 |
| tggttcctct cgttggatct ggctgcagtc ccacattatg cgacatcaca cttacaccaa | 600 |
| ccagcatggc ctcgacctgg atgctgcctc ggcagagccg ttcatcttgt tccactccta | 660 |
| tcctgctacc aacgcctctc gaaagtggta ccaccgattt caggcgtggt acatgtacat | 720 |
| cgttctggga atgtatggtg tctcgatggt gtacaatccc atgtacctct tcacaatgca | 780 |
| gcacaacgac accattcccg aggccacttc tctcagacca ggcagctttt tcaatcggca | 840 |
| gcgagctttc gccgtttccc ttcgactgct cttcatcttc cgaaacgcct tcttccctg | 900 |
| gtacattgct ggtgcctctc ctctgctcac cattcttctg gtgcccacgg tcacaggcat | 960 |
| cttcctcacc tttgtgttcg ttctgtccca taacttcgag ggagccgaac ggaccccaga | 1020 |
| gaagaactgc aaggccaaac gagctaagga aggcaaggag gtcagagacg tggaagagga | 1080 |
| tcgagtcgac tggtaccgag cacaggccga gactgctgcc acctacgtg gcagcgtggg | 1140 |
| aatgatgctt acaggcggtc tcaacctgca gatcgagcat cacttgtttc cccgaatgtc | 1200 |
| ctcttggcac tatcccttca ttcaagacac cgttcgggag tgttgcaagc gacatggcgt | 1260 |
| ccgttacaca tactatccta ccattctcga gaacatcatg tccactcttc gatacatgca | 1320 |
| gaaggtgggt gttgctcaca ccattcagga tgcccaggag ttctaagcgg ccgcaagtgt | 1380 |
| ggatggggaa gtgagtgccc ggttctgtgt gcacaattgg caatccaaga tggatggatt | 1440 |
| caacacaggg atatagcgag ctacgtggtg gtgcgaggat atagcaacgg atatttatgt | 1500 |
| ttgacacttg agaatgtacg atacaagcac tgtccaagta caatactaaa catactgtac | 1560 |
| atactcatac tcgtacccgg caacggtttt cacttgagtg cagtggctag tgctcttact | 1620 |
| cgtacagtgt gcaatactgc gtatcatagt ctttgatgta tatcgtattc attcatgtta | 1680 |
| gttgcgtacg agccggaagc ataaagtgta aagcctgggg tgcctaatga gtgagctaac | 1740 |
| tcacattaat tgcgttgcgc tcactgcccg ctttccagtc gggaaacctg tcgtgccagc | 1800 |
| tgcattaatg aatcggccaa cgcgcgggga gaggcggttt gcgtattggg cgctcttccg | 1860 |

```
cttcctcgct cactgactcg ctgcgctcgg tcgttcggct gcggcgagcg gtatcagctc    1920
actcaaaggc ggtaatacgg ttatccacag aatcagggga taacgcagga agaacatgt    1980 gagcaaaagg ccagcaaaag gccaggaacc gtaaaaaggc cgcgttgctg gcgttttttcc   2040 ataggctccg ccccccctgac gagcatcaca aaaatcgacg ctcaagtcag aggtggcgaa   2100
acccgacagg actataaaga taccaggcgt ttccccctgg aagctccctc gtgcgctctc    2160
ctgttccgac cctgccgctt accggatacc tgtccgcctt tctcccttcg ggaagcgtgg    2220
cgctttctca tagctcacgc tgtaggtatc tcagttcggt gtaggtcgtt cgctccaagc    2280
tgggctgtgt gcacgaaccc cccgttcagc ccgaccgctg cgccttatcc ggtaactatc    2340
gtcttgagtc caacccggta agacacgact tatcgccact ggcagcagcc actggtaaca    2400
ggattagcag agcgaggtat gtaggcggtg ctacagagtt cttgaagtgg tggcctaact    2460
acggctacac tagaaggaca gtatttggta tctgcgctct gctgaagcca gttaccttcg    2520
gaaaaagagt tggtagctct tgatccggca acaaaccac cgctggtagc ggtggttttt    2580
ttgtttgcaa gcagcagatt acgcgcagaa aaaaggatc tcaagaagat cctttgatct    2640
tttctacggg gtctgacgct cagtggaacg aaaactcacg ttaagggatt ttggtcatga    2700
gattatcaaa aaggatcttc acctagatcc ttttaaatta aaaatgaagt tttaaatcaa    2760
tctaaagtat atatgagtaa acttggtctg acagttacca atgcttaatc agtgaggcac    2820
ctatctcagc gatctgtcta tttcgttcat ccatagttgc ctgactcccc gtcgtgtaga    2880
taactacgat acgggagggc ttaccatctg gccccagtgc tgcaatgata ccgcgagacc    2940
cacgctcacc ggctccagat ttatcagcaa taaaccagcc agccggaagg gccgagcgca    3000
gaagtggtcc tgcaacttta tccgcctcca tccagtctat taattgttgc cgggaagcta    3060
gagtaagtag ttcgccagtt aatagtttgc gcaacgttgt tgccattgct acaggcatcg    3120
tggtgtcacg ctcgtcgttt ggtatggctt cattcagctc cggttcccaa cgatcaaggc    3180
gagttacatg atccccatg ttgtgcaaaa aagcggttag ctccttcggt cctccgatcg    3240
ttgtcagaag taagttggcc gcagtgttat cactcatggt tatggcagca ctgcataatt    3300
ctcttactgt catgccatcc gtaagatgct tttctgtgac tggtgagtac tcaaccaagt    3360
cattctgaga atagtgtatg cggcgaccga gttgctcttg cccggcgtca atacgggata    3420
ataccgcgcc acatagcaga actttaaaag tgctcatcat tggaaaacgt tcttcggggc    3480
gaaaactctc aaggatctta ccgctgttga gatccagttc gatgtaaccc actcgtgcac    3540
ccaactgatc ttcagcatct tttactttca ccagcgtttc tgggtgagca aaaacaggaa    3600
ggcaaaatgc cgcaaaaaag ggaataaggg cgacacggaa atgttgaata ctcatactct    3660
tcctttttca atattattga agcatttatc agggttattg tctcatgagc ggatacatat    3720
ttgaatgtat ttagaaaaat aaacaaatag gggttccgcg cacatttccc cgaaaagtgc    3780
cacctgacgc gccctgtagc ggcgcattaa gcgcggcggg tgtggtggtt acgcgcagcg    3840
tgaccgctac acttgccagc gccctagcgc ccgctccttt cgctttcttc ccttcctttc    3900
tcgccacgtt cgccggcttt ccccgtcaag ctctaaatcg gggggctccct ttagggttcc    3960 gatttagtgc tttacggcac ctcgacccca aaaaacttga ttagggtgat ggttcacgta    4020
gtgggccatc gccctgatag acggtttttc gccctttgac gttggagtcc acgttcttta    4080
atagtggact cttgttccaa actggaacaa cactcaaccc tatctcggtc tattcttttg    4140
atttataagg gattttgccg atttcggcct attggttaaa aaatgagctg atttaacaaa    4200
aatttaacgc gaattttaac aaaatattaa cgcttacaat ttccattcgc cattcaggct    4260
```

```
gcgcaactgt tgggaagggc gatcggtgcg ggcctcttcg ctattacgcc agctggcgaa   4320
agggggatgt gctgcaaggc gattaagttg ggtaacgcca gggttttccc agtcacgacg   4380
ttgtaaaacg acggccagtg aattgtaata cgactcacta tagggcgaat tgggtaccgg   4440
gccccccctc gaggtcgatg gtgtcgataa gcttgatatc gaattcatgt cacacaaacc   4500
gatcttcgcc tcaaggaaac ctaattctac atccgagaga ctgccagat ccagtctaca   4560 ctgattaatt ttcgggccaa taatttaaaa aaatcgtgtt atataatatt atatgtatta   4620
tatatataca tcatgatgat actgacagtc atgtcccatt gctaaataga cagactccat   4680
ctgccgcctc caactgatgt tctcaatatt taagggtca tctcgcattg tttaataata   4740
aacagactcc atctaccgcc tccaaatgat gttctcaaaa tatattgtat gaacttattt   4800
ttattactta gtattattag acaacttact tgctttatga aaacacttc ctatttagga   4860 aacaatttat aatggcagtt cgttcattta acaatttatg tagaataaat gttataaatg   4920
cgtatgggaa atcttaaata tggatagcat aaatgatatc tgcattgcct aattcgaaat   4980
caacagcaac gaaaaaaatc ccttgtacaa cataaatagt catcgagaaa tatcaactat   5040
caaagaacag ctattcacac gttactattg agattattat tggacgagaa tcacacactc   5100 aactgtctt ctctcttcta gaaatacagg tacaagtatg tactattctc attgttcata   5160
cttctagtca tttcatccca catattcctt ggatttctct ccaatgaatg acattctatc   5220
ttgcaaattc aacaattata ataagatata ccaaagtagc ggtatagtgg caatcaaaaa   5280
gcttctctgg tgtgcttctc gtatttatt ttattctaat gatccattaa aggtatatat   5340
ttatttcttg ttatataatc cttttgttta ttacatgggc tggatacata aaggtatttt   5400
gatttaattt tttgcttaaa ttcaatcccc cctcgttcag tgtcaactgt aatggtagga   5460
aattaccata cttttgaaga agcaaaaaaa atgaaagaaa aaaaaaatcg tatttccagg   5520
ttagacgttc cgcagaatct agaatgcggt atgcggtaca ttgttcttcg aacgtaaaag   5580
ttgcgctccc tgagatattg tacatttttg cttttacaag tacaagtaca tcgtacaact   5640
atgtactact gttgatgcat ccacaacagt ttgttttgtt tttttttgtt ttttttttt   5700 ctaatgattc attaccgcta tgtataccta cttgtacttg tagtaagccg ggttattggc   5760
gttcaattaa tcatagactt atgaatctgc acggtgtgcg ctgcgagtta cttttagctt   5820
atgcatgcta cttgggtgta atattgggat ctgttcggaa atcaacggat gctcaatcga   5880
tttcgacagt aattaattaa gtcatacaca agtcagcttt cttcgagcct catataagta   5940
taagtagttc aacgtattag cactgtaccc agcatctccg tatcgagaaa cacaacaaca   6000
tgccccattg gacagatcat gcggatacac aggttgtgca gtatcataca tactcgatca   6060
gacaggtcgt ctgaccatca tacaagctga acaagcgctc catacttgca cgctctctat   6120
atacacagtt aaattacata tccatagtct aacctctaac agttaatctt ctggtaagcc   6180
tcccagccag ccttctggta tcgcttggcc tcctcaatag gatctcggtt ctggccgtac   6240
agacctcggc cgacaattat gatatccgtt ccggtagaca tgacatcctc aacagttcgg   6300
tactgctgtc cgagagcgtc tcccttgtcg tcaagaccca ccccgggggt cagaataagc   6360
cagtcctcag agtcgccctt aggtcggttc tgggcaatga agccaaccac aaactcgggg   6420
tcggatcggc caagctcaat ggtctgcttg gagtactcgc cagtggccag agagcccttg   6480
caagacagct cggccagcat gagcagacct ctggccagct tctcgttggg agaggggact   6540
aggaactcct tgtactggga gttctcgtag tcagagacgt cctccttctt ctgttcagag   6600
acagtttcct cggcaccagc tcgcaggcca gcaatgattc cggttccggg tacaccgtgg   6660
```

```
gcgttggtga tatcggacca ctcggcgatt cggtgacacc ggtactggtg cttgacagtg    6720
ttgccaatat ctgcgaactt tctgtcctcg aacaggaaga aaccgtgctt aagagcaagt    6780
tccttgaggg ggagcacagt gccggcgtag gtgaagtcgt caatgatgtc gatatgggtt    6840
ttgatcatgc acacataagg tccgaccttta tcggcaagct caatgagctc cttggtggtg    6900
gtaacatcca gagaagcaca caggttggtt ttcttggctg ccacgagctt gagcactcga    6960
gcggcaaagg cggacttgtg gacgttagct cgagcttcgt aggagggcat tttggtggtg    7020
aagaggagac tgaaataaat ttagtctgca gaacttttta tcggaacctt atctggggca    7080
gtgaagtata tgttatggta atagttacga gttagttgaa cttatagata gactggacta    7140
tacggctatc ggtccaaatt agaaagaacg tcaatggctc tctgggcgtc gcctttgccg    7200
acaaaaatgt gatcatgatg aaagccagca atgacgttgc agctgatatt gttgtcggcc    7260
aaccgcgccg aaaacgcagc tgtcagaccc acagcctcca acgaagaatg tatcgtcaaa    7320
gtgatccaag cacactcata gttggagtcg tactccaaag gcggcaatga cgagtcagac    7380
agatactcgt cgacgtttaa acagtgtacg cagatctact atagaggaac atttaaattg    7440
ccccggagaa gacggccagg ccgcctagat gacaaattca acaactcaca gctgactttc    7500
tgccattgcc actagggggg ggccttttta tatggccaag ccaagctctc cacgtcggtt    7560
gggctgcacc caacaataaa tgggtagggt tgcaccaaca aagggatggg atgggggta    7620 gaagatacga ggataacggg gctcaatggc acaaataaga acgaatactg ccattaagac    7680
tcgtgatcca gcgactgaca ccattgcatc atctaagggc ctcaaaacta cctcggaact    7740
gctgcgctga tctggacacc acagaggttc cgagcacttt aggttgcacc aaatgtccca    7800
ccaggtgcag gcagaaaacg ctggaacagc gtgtacagtt tgtcttaaca aaagtgagg    7860 gcgctgaggt cgagcagggt ggtgtgactt gttatagcct ttagagctgc gaaagcgcgt    7920
atggatttgg ctcatcaggc cagattgagg gtctgtggac acatgtcatg ttagtgtact    7980
tcaatcgccc cctggatata gccccgacaa taggccgtgg cctcattttt ttgccttccg    8040
cacatttcca ttgctcgata cccacaccttt gcttctcctg cacttgccaa ccttaatact    8100
ggtttacatt gaccaacatc ttacaagcgg ggggcttgtc tagggtatat ataaacagtg    8160
gctctcccaa tcggttgcca gtctcttttt tcctttcttt ccccacagat tcgaaatcta    8220
aactacacat cacagaattc cgagccgtga gtatccacga caagatcagt gtcgagacga    8280
cgcgttttgt gtaatgacac aatccgaaag tcgctagcaa cacacactct ctacacaaac    8340
taacccagct ctggtac                                                   8357
```

<210> SEQ ID NO 99
<211> LENGTH: 8165
<212> TYPE: DNA
<213> ORGANISM: Artificial Sequence
<220> FEATURE:
<223> OTHER INFORMATION: Plasmid pZUF17

<400> SEQUENCE: 99

```
gtacgagccg gaagcataaa gtgtaaagcc tggggtgcct aatgagtgag ctaactcaca      60
ttaattgcgt tgcgctcact gcccgctttc cagtcgggaa acctgtcgtg ccagctgcat     120
taatgaatcg gccaacgcgc ggggagaggc ggtttgcgta ttgggcgctc ttccgcttcc     180
tcgctcactg actcgctgcg ctcggtcgtt cggctgcggc gagcggtatc agctcactca     240
aaggcggtaa tacggttatc cacagaatca ggggataacg caggaaagaa catgtgagca     300
aaaggccagc aaaaggccag gaaccgtaaa aaggccgcgt tgctggcgtt tttccatagg     360
```

```
ctccgccccc ctgacgagca tcacaaaaat cgacgctcaa gtcagaggtg gcgaaacccg      420
acaggactat aaagatacca ggcgtttccc cctggaagct ccctcgtgcg ctctcctgtt      480
ccgaccctgc cgcttaccgg atacctgtcc gcctttctcc cttcgggaag cgtggcgctt      540
tctcatagct cacgctgtag gtatctcagt tcggtgtagg tcgttcgctc caagctgggc      600
tgtgtgcacg aacccccccgt tcagcccgac cgctgcgcct tatccggtaa ctatcgtctt      660
gagtccaacc cggtaagaca cgacttatcg ccactggcag cagccactgg taacaggatt      720
agcagagcga ggtatgtagg cggtgctaca gagttcttga agtggtggcc taactacggc      780
tacactagaa ggacagtatt tggtatctgc gctctgctga agccagttac cttcggaaaa      840
agagttggta gctcttgatc cggcaaacaa accaccgctg gtagcggtgg ttttttttgtt      900 tgcaagcagc agattacgcg cagaaaaaaa ggatctcaag aagatccttt gatcttttct      960
acggggtctg acgctcagtg gaacgaaaac tcacgttaag ggattttggt catgagatta     1020
tcaaaaagga tcttcaccta gatccttttta aattaaaaat gaagttttaa atcaatctaa     1080
agtatatatg agtaaacttg gtctgacagt taccaatgct taatcagtga ggcacctatc     1140
tcagcgatct gtctatttcg ttcatccata gttgcctgac tccccgtcgt gtagataact     1200
acgatacggg agggcttacc atctggcccc agtgctgcaa tgataccgcg agacccacgc     1260
tcaccggctc cagatttatc agcaataaac cagccagccg gaagggccga gcgcagaagt     1320
ggtcctgcaa cttatccgc ctccatccag tctattaatt gttgccggga agctagagta     1380
agtagttcgc cagttaatag tttgcgcaac gttgttgcca ttgctacagg catcgtggtg     1440
tcacgctcgt cgtttggtat ggcttcattc agctccggtt cccaacgatc aaggcgagtt     1500
acatgatccc ccatgttgtg caaaaaagcg gttagctcct tcggtcctcc gatcgttgtc     1560
agaagtaagt tggccgcagt gttatcactc atggttatgg cagcactgca taattctctt     1620
actgtcatgc catccgtaag atgcttttct gtgactggtg agtactcaac caagtcattc     1680
tgagaatagt gtatgcggcg accgagttgc tcttgcccgg cgtcaatacg ggataatacc     1740
gcgccacata gcagaacttt aaaagtgctc atcattggaa aacgttcttc ggggcgaaaa     1800
ctctcaagga tcttaccgct gttgagatcc agttcgatgt aacccactcg tgcacccaac     1860
tgatcttcag catcttttac tttcaccagc gtttctgggt gagcaaaaac aggaaggcaa     1920
aatgccgcaa aaaagggaat aagggcgaca cggaaatgtt gaatactcat actcttcctt     1980
tttcaatatt attgaagcat ttatcagggt tattgtctca tgagcggata catatttgaa     2040
tgtatttaga aaaataaaca ataggggtt ccgcgcacat ttccccgaaa agtgccacct     2100
gacgcgccct gtagcggcgc attaagcgcg gcgggtgtgg tggttacgcg cagcgtgacc     2160
gctacacttg ccagcgccct agcgcccgct cctttcgctt tcttcccttc ctttctcgcc     2220
acgttcgccg gctttccccg tcaagctcta aatcggggc tccctttagg gttccgattt     2280
agtgctttac ggcacctcga ccccaaaaaa cttgattagg gtgatggttc acgtagtggg     2340
ccatcgccct gatagacggt ttttcgccct ttgacgttgg agtccacgtt ctttaatagt     2400
ggactcttgt tccaaactgg aacaacactc aaccctatct cggtctattc ttttgattta     2460
taagggattt tgccgatttc ggcctattgg ttaaaaaatg agctgattta acaaaaattt     2520
aacgcgaatt ttaacaaaat attaacgctt acaatttcca ttcgccattc aggctgcgca     2580
actgttggga agggcgatcg gtgcgggcct cttcgctatt acgccagctg gcgaaagggg     2640
gatgtgctgc aaggcgatta agttgggtaa cgccagggtt ttcccagtca cgacgttgta     2700
aaacgacggc cagtgaattg taatacgact cactataggg cgaattgggt accgggcccc     2760
```

```
ccctcgaggt cgatggtgtc gataagcttg atatcgaatt catgtcacac aaaccgatct   2820
tcgcctcaag gaaacctaat tctacatccg agagactgcc gagatccagt ctacactgat   2880
taattttcgg gccaataatt taaaaaaatc gtgttatata atattatatg tattatatat   2940
atacatcatg atgatactga cagtcatgtc ccattgctaa atagacagac tccatctgcc   3000
gcctccaact gatgttctca atatttaagg ggtcatctcg cattgtttaa taataaacag   3060
actccatcta ccgcctccaa atgatgttct caaaatatat tgtatgaact tatttttatt   3120
acttagtatt attagacaac ttacttgctt tatgaaaaac acttcctatt taggaaacaa   3180
tttataatgg cagttcgttc atttaacaat ttatgtagaa taaatgttat aaatgcgtat   3240
gggaaatctt aaatatggat agcataaatg atatctgcat tgcctaattc gaaatcaaca   3300
gcaacgaaaa aaatcccttg tacaacataa atagtcatcg agaaatatca actatcaaag   3360
aacagctatt cacacgttac tattgagatt attattggac gagaatcaca cactcaactg   3420
tctttctctc ttctagaaat acaggtacaa gtatgtacta ttctcattgt tcatacttct   3480
agtcatttca tcccacatat tccttggatt tctctccaat gaatgacatt ctatcttgca   3540
aattcaacaa ttataataag atataccaaa gtagcggtat agtggcaatc aaaaagcttc   3600
tctggtgtgc ttctcgtatt tattttatt ctaatgatcc attaaaggta tatatttatt   3660
tcttgttata taatccttt gtttattaca tgggctggat acataaaggt attttgattt   3720
aattttttgc ttaaattcaa tcccccctcg ttcagtgtca actgtaatgg taggaaatta   3780
ccatactttt gaagaagcaa aaaaaatgaa agaaaaaaaa aatcgtattt ccaggttaga   3840
cgttccgcag aatctagaat gcggtatgcg gtacattgtt cttcgaacgt aaaagttgcg   3900
ctccctgaga tattgtacat ttttgctttt acaagtacaa gtacatcgta caactatgta   3960
ctactgttga tgcatccaca acagtttgtt ttgttttttt ttgtttttt tttttctaat   4020 gattcattac cgctatgtat acctacttgt acttgtagta agccgggtta ttggcgttca   4080
attaatcata gacttatgaa tctgcacggt gtgcgctgcg agttactttt agcttatgca   4140
tgctacttgg gtgtaatatt gggatctgtt cggaaatcaa cggatgctca atcgatttcg   4200
acagtaatta attaagtcat acacaagtca gctttcttcg agcctcatat aagtataagt   4260
agttcaacgt attagcactg tacccagcat ctccgtatcg agaaacacaa caacatgccc   4320
cattggacag atcatgcgga tacacaggtt gtgcagtatc atacatactc gatcagacag   4380
gtcgtctgac catcatacaa gctgaacaag cgctccatac ttgcacgctc tctatataca   4440
cagttaaatt acatatccat agtctaacct ctaacagtta atcttctggt aagcctccca   4500
gccagccttc tggtatcgct tggcctcctc aataggatct cggttctggc cgtacagacc   4560
tcggccgaca attatgatat ccgttccggt agacatgaca tcctcaacag ttcggtactg   4620
ctgtccgaga gcgtctccct tgtcgtcaag acccaccccg ggggtcagaa taagccagtc   4680
ctcagagtcg cccttaggtc ggttctgggc aatgaagcca accacaaact cggggtcgga   4740
tcgggcaagc tcaatggtct gcttggagta ctcgccagtg gccagagagc ccttgcaaga   4800
cagctcggcc agcatgagca gacctctggc cagcttctcg ttgggagagg ggactaggaa   4860
ctccttgtac tgggagttct cgtagtcaga gacgtcctcc ttcttctgtt cagagacagt   4920
ttcctcggca ccagctcgca ggccagcaat gattccggtt ccgggtacac cgtgggcgtt   4980
ggtgatatcg gaccactcgg cgattcggtg acaccggtac tggtgcttga cagtgttgcc   5040
aatatctgcg aactttctgt cctcgaacag gaagaaaccg tgcttaagag caagttcctt   5100
gagggggagc acagtgccgg cgtaggtgaa gtcgtcaatg atgtcgatat gggttttgat   5160
```

```
catgcacaca taaggtccga ccttatcggc aagctcaatg agctccttgg tggtggtaac   5220
atccagagaa gcacacaggt tggttttctt ggctgccacg agcttgagca ctcgagcggc   5280
aaaggcggac ttgtggacgt tagctcgagc ttcgtaggag ggcattttgg tggtgaagag   5340
gagactgaaa taaatttagt ctgcagaact ttttatcgga accttatctg gggcagtgaa   5400
gtatatgtta tggtaatagt tacgagttag ttgaacttat agatagactg gactatacgg   5460
ctatcggtcc aaattagaaa gaacgtcaat ggctctctgg gcgtcgcctt tgccgacaaa   5520
aatgtgatca tgatgaaagc cagcaatgac gttgcagctg atattgttgt cggccaaccg   5580
cgccgaaaac gcagctgtca gacccacagc ctccaacgaa gaatgtatcg tcaaagtgat   5640
ccaagcacac tcatagttgg agtcgtactc caaaggcggc aatgacgagt cagacagata   5700
ctcgtcgact caggcgacga cggaattcct gcagcccatc tgcagaattc aggagagacc   5760
gggttggcgg cgtatttgtg tcccaaaaaa cagccccaat tgccccggag aagacggcca   5820
ggccgcctag atgacaaatt caacaactca cagctgactt tctgccattg ccactagggg   5880
ggggcctttt tatatggcca agccaagctc tccacgtcgg ttgggctgca cccaacaata   5940
aatgggtagg gttgcaccaa caaagggatg ggatggggggg tagaagatac gaggataacg   6000
gggctcaatg gcacaaataa gaacgaatac tgccattaag actcgtgatc cagcgactga   6060
caccattgca tcatctaagg gcctcaaaac tacctcggaa ctgctgcgct gatctggaca   6120
ccacagaggt tccgagcact ttaggttgca ccaaatgtcc caccaggtgc aggcagaaaa   6180
cgctggaaca gcgtgtacag tttgtcttaa caaaaagtga gggcgctgag gtcgagcagg   6240
gtggtgtgac ttgttatagc ctttagagct gcgaaagcgc gtatggattt ggctcatcag   6300
gccagattga gggtctgtgg acacatgtca tgttagtgta cttcaatcgc cccctggata   6360
tagccccgac aataggccgt ggcctcattt ttttgccttc cgcacatttc cattgctcgg   6420
tacccacacc ttgcttctcc tgcacttgcc aaccttaata ctggtttaca ttgaccaaca   6480
tcttacaagc gggggggcttg tctagggtat atataaacag tggctctccc aatcggttgc   6540
cagtctcttt tttcctttct ttccccacag attcgaaatc taaactacac atcacacaat   6600
gcctgttact gacgtcctta agcgaaagtc cggtgtcatc gtcggcgacg atgtccgagc   6660
cgtgagtatc cacgacaaga tcagtgtcga gacgacgcgt tttgtgtaat gacacaatcc   6720
gaaagtcgct agcaacacac actctctaca caaactaacc cagctctcca tggctgagga   6780
taagaccaag gtcgagttcc ctaccctgac tgagctgaag cactctatcc ctaacgcttg   6840
ctttgagtcc aacctcggac tctcgctcta ctacactgcc cgagcgatct tcaacgcatc   6900
tgcctctgct gctctgctct acgctgcccg atctactccc ttcattgccg ataacgttct   6960
gctccacgct ctggtttgcg ccacctacat ctacgtgcag ggtgtcatct tctggggttt   7020
ctttaccgtc ggtcacgact gtggtcactc tgccttctcc cgataccact ccgtcaactt   7080
catcattggc tgcatcatgc actctgccat tctgactccc ttcgagtcct ggcgagtgac   7140
ccaccgacac catcacaaga acactggcaa cattgataag gacgagatct tctaccctca   7200
tcggtccgtc aaggacctcc aggacgtgcg acaatgggtc tacaccctcg gaggtgcttg   7260
gtttgtctac ctgaaggtcg gatatgctcc tcgaaccatg tcccactttg acccctggga   7320
ccctctcctg cttcgacgag cctccgctgt catcgtgtcc ctcggagtct gggctgcctt   7380
cttcgctgcc tacgcctacc tcacatactc gctcggcttt gccgtcatgg gcctctacta   7440
ctatgctcct ctctttgtct ttgcttcgtt cctcgtcatt actaccttct tgcatcacaa   7500
cgacgaagct actccctggt acggtgactc ggagtggacc tacgtcaagg gcaacctgag   7560
```

-continued

| | |
|---|---|
| ctccgtcgac cgatcgtacg gagctttcgt ggacaacctg tctcaccaca ttggcaccca | 7620 |
| ccaggtccat cacttgttcc ctatcattcc ccactacaag ctcaacgaag ccaccaagca | 7680 |
| ctttgctgcc gcttaccctc acctcgtgag acgtaacgac gagcccatca ttactgcctt | 7740 |
| cttcaagacc gctcacctct ttgtcaacta cggagctgtg cccgagactg ctcagatttt | 7800 |
| caccctcaaa gagtctgccg ctgcagccaa ggccaagagc gactaagcgg ccgcaagtgt | 7860 |
| ggatggggaa gtgagtgccc ggttctgtgt gcacaattgg caatccaaga tggatggatt | 7920 |
| caacacaggg atatagcgag ctacgtggtg gtgcgaggat atagcaacgg atatttatgt | 7980 |
| ttgacacttg agaatgtacg atacaagcac tgtccaagta caatactaaa catactgtac | 8040 |
| atactcatac tcgtacccgg gcaacggttt cacttgagtg cagtggctag tgctcttact | 8100 |
| cgtacagtgt gcaatactgc gtatcatagt ctttgatgta tatcgtattc attcatgtta | 8160 |
| gttgc | 8165 |

<210> SEQ ID NO 100
<211> LENGTH: 3983
<212> TYPE: DNA
<213> ORGANISM: Artificial Sequence
<220> FEATURE:
<223> OTHER INFORMATION: Plasmid pEaD5S

<400> SEQUENCE: 100

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcaggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cgagctcggt acctcgcgaa | 420 |
| tgcatctaga tccatggtca agcgaccgc tctgcctctc accgtggacg gtgtcaccta | 480 |
| cgacgtttct gcctggctca accaccatcc cggaggtgcc gacattatcg agaactaccg | 540 |
| aggtcgggat gctaccgacg tcttcatggt tatgcactcc gagaacgccg tgtccaaact | 600 |
| cagacgaatg cccatcatgg aaccttcctc tcccctgact ccaacacctc ccaagccaaa | 660 |
| ctccgacgaa cctcaggagg atttccgaaa gctgcgagac gagctcattg ctgcaggcat | 720 |
| gttcgatgcc tctcccatgt ggtacgctta caagaccctg tcgactctcg gactgggtgt | 780 |
| ccttgccgtg ctgttgatga cccagtggca ctggtacctg gttggtgcta tcgtcctcgg | 840 |
| cattcacttt caacagatgg gatggctctc gcacgacatt gccatcacc agctgttcaa | 900 |
| ggaccgatcc atcaacaatg ccattggcct gctcttcgga acgtgcttc agggcttttc | 960 |
| tgtcacttgg tggaaggacc gacacaacgc tcatcactcc gccaccaacg tgcagggtca | 1020 |
| cgatcccgac atcgacaacc tgcctctcct ggcgtggtcc aaggaggacg tcgagcgagc | 1080 |
| tggcccgttt ctcgacggga tgatcaagta ccaacagtat tacttctttt tcatctgtgc | 1140 |
| ccttctgcga ttcatctggt gctttcagtc cattcatact gccacgggtc tcaaggatcg | 1200 |
| aagcaatcag tactatcgaa gacagtacga gaaggagtcc gtcggtctgg cactccactg | 1260 |
| gggtctcaag gccttgttct actatttcta catgccctcg tttctcaccg gactcatggt | 1320 |
| gttctttgtc tccgagctgc ttggtggctt cggaattgcc atcgttgtct tcatgaacca | 1380 |
| ctaccctctg gagaagattc aggactccgt gtgggatggt catggcttct gtgctggaca | 1440 |

```
gattcacgag accatgaacg ttcagcgagg cctcgtcaca gactggtttt tcggtggcct    1500
caactaccag atcgaacatc acctgtggcc tactcttccc agacacaacc tcaccgctgc    1560
ctccatcaaa gtggagcagc tgtgcaagaa gcacaacctg ccctaccgat ctcctcccat    1620
gctcgaaggt gtcggcattc ttatctccta cctgggcacc ttcgctcgaa tggttgccaa    1680
ggcagacaag gcctaagcgg ccgcatcgga tcccgggccc gtcgactgca gaggcctgca    1740
tgcaagcttg gcgtaatcat ggtcatagct gtttcctgtg tgaaattgtt atccgctcac    1800
aattccacac aacatacgag ccggaagcat aaagtgtaaa gcctggggtg cctaatgagt    1860
gagctaactc acattaattg cgttgcgctc actgcccgct ttccagtcgg gaaacctgtc    1920
gtgccagctg cattaatgaa tcggccaacg cgcggggaga ggcggtttgc gtattgggcg    1980
ctcttccgct tcctcgctca ctgactcgct gcgctcggtc gttcggctgc ggcgagcggt    2040
atcagctcac tcaaaggcgg taatacggtt atccacagaa tcaggggata acgcaggaaa    2100
gaacatgtga gcaaaaggcc agcaaaaggc caggaaccgt aaaaaggccg cgttgctggc    2160
gtttttccat aggctccgcc cccctgacga gcatcacaaa aatcgacgct caagtcagag    2220
gtggcgaaac ccgacaggac tataaagata ccaggcgttt ccccctggaa gctccctcgt    2280
gcgctctcct gttccgaccc tgccgcttac cggatacctg tccgcctttc tcccttcggg    2340
aagcgtggcg ctttctcata gctcacgctg taggtatctc agttcggtgt aggtcgttcg    2400
ctccaagctg ggctgtgtgc acgaaccccc cgttcagccc gaccgctgcg ccttatccgg    2460
taactatcgt cttgagtcca acccggtaag acacgactta tcgccactgg cagcagccac    2520
tggtaacagg attagcagag cgaggtatgt aggcggtgct acagagttct tgaagtggtg    2580
gcctaactac ggctacacta agaacagt atttggtatc tgcgctctgc tgaagccagt    2640
taccttcgga aaagagttg gtagctcttg atccggcaaa caaaccaccg ctggtagcgg    2700 tggtttttttt gtttgcaagc agcagattac gcgcagaaaa aaggatctc aagaagatcc    2760 tttgatcttt tctacggggt ctgacgctca gtggaacgaa aactcacgtt aagggatttt    2820
ggtcatgaga ttatcaaaaa ggatcttcac ctagatcctt ttaaattaaa aatgaagttt    2880
taaatcaatc taaagtatat atgagtaaac ttggtctgac agttaccaat gcttaatcag    2940
tgaggcacct atctcagcga tctgtctatt tcgttcatcc atagttgcct gactccccgt    3000
cgtgtagata actacgatac gggagggctt accatctggc cccagtgctg caatgatacc    3060
gcgagaccca cgctcaccgg ctccagattt atcagcaata aaccagccag ccggaagggc    3120
cgagcgcaga agtggtcctg caactttatc cgcctccatc cagtctatta attgttgccg    3180
ggaagctaga gtaagtagtt cgccagttaa tagtttgcgc aacgttgttg ccattgctac    3240
aggcatcgtg gtgtcacgct cgtcgtttgg tatggcttca ttcagctccg gttcccaacg    3300
atcaaggcga gttacatgat cccccatgtt gtgcaaaaaa gcggttagct ccttcggtcc    3360
tccgatcgtt gtcagaagta agttggccgc agtgttatca ctcatggtta tggcagcact    3420
gcataattct cttactgtca tgccatccgt aagatgcttt tctgtgactg gtgagtactc    3480
aaccaagtca ttctgagaat agtgtatgcg gcgaccgagt tgctcttgcc cggcgtcaat    3540 acggataat accgcgccac atagcagaac tttaaaagtg ctcatcattg gaaaacgttc    3600
ttcggggcga aaactctcaa ggatcttacc gctgttgaga tccagttcga tgtaacccac    3660
tcgtgcaccc aactgatctt cagcatcttt tactttcacc agcgtttctg gtgagcaaa    3720 aacaggaagg caaaatgccg caaaaaaggg aataagggcg acacggaaat gttgaatact    3780
catactcttc ctttttcaat attattgaag catttatcag ggttattgtc tcatgagcgg    3840
```

```
atacatattt gaatgtattt agaaaaataa acaaataggg gttccgcgca catttccccg    3900
aaaagtgcca cctgacgtct aagaaaccat tattatcatg acattaacct ataaaaatag    3960
gcgtatcacg aggccctttc gtc                                            3983
```

<210> SEQ ID NO 101
<211> LENGTH: 37
<212> TYPE: DNA
<213> ORGANISM: Artificial Sequence
<220> FEATURE:
<223> OTHER INFORMATION: Primer A10A.HaGG

<400> SEQUENCE: 101
gtctggccaa ggtgcatgcc ggaggcaacc tcatcga        37

<210> SEQ ID NO 102
<211> LENGTH: 37
<212> TYPE: DNA
<213> ORGANISM: Artificial Sequence
<220> FEATURE:
<223> OTHER INFORMATION: Primer A10B.HaGG

<400> SEQUENCE: 102
tcgatgaggt tgcctccggc atgcaccttg gccagac        37

<210> SEQ ID NO 103
<211> LENGTH: 37
<212> TYPE: DNA
<213> ORGANISM: Artificial Sequence
<220> FEATURE:
<223> OTHER INFORMATION: Primer A11A.HrGG

<400> SEQUENCE: 103
gtctggccaa ggtgcatcga ggaggcaacc tcatcga        37

<210> SEQ ID NO 104
<211> LENGTH: 37
<212> TYPE: DNA
<213> ORGANISM: Artificial Sequence
<220> FEATURE:
<223> OTHER INFORMATION: Primer A11B.HrGG

<400> SEQUENCE: 104
tcgatgaggt tgcctccacg atgcaccttg gccagac        37

<210> SEQ ID NO 105
<211> LENGTH: 37
<212> TYPE: DNA
<213> ORGANISM: Artificial Sequence
<220> FEATURE:
<223> OTHER INFORMATION: Primer A12A.HnGG

<400> SEQUENCE: 105
gtctggccaa ggtgcataac ggaggcaacc tcatcga        37

<210> SEQ ID NO 106
<211> LENGTH: 37
<212> TYPE: DNA
<213> ORGANISM: Artificial Sequence
<220> FEATURE:
<223> OTHER INFORMATION: Primer A12B.HnGG

<400> SEQUENCE: 106
tcgatgaggt tgcctccgtt atgcaccttg gccagac        37

```
<210> SEQ ID NO 107
<211> LENGTH: 37
<212> TYPE: DNA
<213> ORGANISM: Artificial Sequence
<220> FEATURE:
<223> OTHER INFORMATION: Primer A33A.HdGG

<400> SEQUENCE: 107
gtctggccaa ggtgcatgac ggaggcaacc tcatcga                            37

<210> SEQ ID NO 108
<211> LENGTH: 37
<212> TYPE: DNA
<213> ORGANISM: Artificial Sequence
<220> FEATURE:
<223> OTHER INFORMATION: Primer A33B.HdGG

<400> SEQUENCE: 108
tcgatgaggt tgcctccgtc atgcaccttg gccagac                            37

<210> SEQ ID NO 109
<211> LENGTH: 37
<212> TYPE: DNA
<213> ORGANISM: Artificial Sequence
<220> FEATURE:
<223> OTHER INFORMATION: Primer A34A.HcGG

<400> SEQUENCE: 109
gtctggccaa ggtgcattgc ggaggcaacc tcatcga                            37

<210> SEQ ID NO 110
<211> LENGTH: 37
<212> TYPE: DNA
<213> ORGANISM: Artificial Sequence
<220> FEATURE:
<223> OTHER INFORMATION: Primer A34B.HcGG

<400> SEQUENCE: 110
tcgatgaggt tgcctccgca atgcaccttg gccagac                            37

<210> SEQ ID NO 111
<211> LENGTH: 37
<212> TYPE: DNA
<213> ORGANISM: Artificial Sequence
<220> FEATURE:
<223> OTHER INFORMATION: Primer A35A.HqGG

<400> SEQUENCE: 111
gtctggccaa ggtgcatcag ggaggcaacc tcatcga                            37

<210> SEQ ID NO 112
<211> LENGTH: 37
<212> TYPE: DNA
<213> ORGANISM: Artificial Sequence
<220> FEATURE:
<223> OTHER INFORMATION: Primer A35B.HqGG

<400> SEQUENCE: 112
tcgatgaggt tgcctccctg atgcaccttg gccagac                            37

<210> SEQ ID NO 113
<211> LENGTH: 37
<212> TYPE: DNA
<213> ORGANISM: Artificial Sequence
<220> FEATURE:
<223> OTHER INFORMATION: Primer A36A.HeGG

<400> SEQUENCE: 113
```

-continued gtctggccaa ggtgcatgag ggaggcaacc tcatcga    37

<210> SEQ ID NO 114
<211> LENGTH: 37
<212> TYPE: DNA
<213> ORGANISM: Artificial Sequence
<220> FEATURE:
<223> OTHER INFORMATION: Primer A36B.HeGG

<400> SEQUENCE: 114
tcgatgaggt tgcctccctc atgcaccttg gccagac    37

<210> SEQ ID NO 115
<211> LENGTH: 37
<212> TYPE: DNA
<213> ORGANISM: Artificial Sequence
<220> FEATURE:
<223> OTHER INFORMATION: Primer A13A.HgGG

<400> SEQUENCE: 115
gtctggccaa ggtgcatggt ggaggcaacc tcatcga    37

<210> SEQ ID NO 116
<211> LENGTH: 37
<212> TYPE: DNA
<213> ORGANISM: Artificial Sequence
<220> FEATURE:
<223> OTHER INFORMATION: Primer A13B.HgGG

<400> SEQUENCE: 116
tcgatgaggt tgcctccacc atgcaccttg gccagac    37

<210> SEQ ID NO 117
<211> LENGTH: 37
<212> TYPE: DNA
<213> ORGANISM: Artificial Sequence
<220> FEATURE:
<223> OTHER INFORMATION: Primer A14A.HhGG

<400> SEQUENCE: 117
gtctggccaa ggtgcatcac ggaggcaacc tcatcga    37

<210> SEQ ID NO 118
<211> LENGTH: 37
<212> TYPE: DNA
<213> ORGANISM: Artificial Sequence
<220> FEATURE:
<223> OTHER INFORMATION: Primer A14B.HhGG

<400> SEQUENCE: 118
tcgatgaggt tgcctccgtg atgcaccttg gccagac    37

<210> SEQ ID NO 119
<211> LENGTH: 37
<212> TYPE: DNA
<213> ORGANISM: Artificial Sequence
<220> FEATURE:
<223> OTHER INFORMATION: Primer A15A.HiGG

<400> SEQUENCE: 119
gtctggccaa ggtgcatatc ggaggcaacc tcatcga    37

<210> SEQ ID NO 120
<211> LENGTH: 37
<212> TYPE: DNA
<213> ORGANISM: Artificial Sequence
<220> FEATURE:
<223> OTHER INFORMATION: Primer A15B.HiGG

<400> SEQUENCE: 120
tcgatgaggt tgcctccgat atgcaccttg gccagac        37

<210> SEQ ID NO 121
<211> LENGTH: 37
<212> TYPE: DNA
<213> ORGANISM: Artificial Sequence
<220> FEATURE:
<223> OTHER INFORMATION: Primer A16A.HlGG

<400> SEQUENCE: 121
gtctggccaa ggtgcatctg ggaggcaacc tcatcga        37

<210> SEQ ID NO 122
<211> LENGTH: 37
<212> TYPE: DNA
<213> ORGANISM: Artificial Sequence
<220> FEATURE:
<223> OTHER INFORMATION: Primer A16B.HlGG

<400> SEQUENCE: 122
tcgatgaggt tgcctcccag atgcaccttg gccagac        37

<210> SEQ ID NO 123
<211> LENGTH: 37
<212> TYPE: DNA
<213> ORGANISM: Artificial Sequence
<220> FEATURE:
<223> OTHER INFORMATION: Primer A17A.HkGG

<400> SEQUENCE: 123
gtctggccaa ggtgcataag ggaggcaacc tcatcga        37

<210> SEQ ID NO 124
<211> LENGTH: 37
<212> TYPE: DNA
<213> ORGANISM: Artificial Sequence
<220> FEATURE:
<223> OTHER INFORMATION: Primer A17B.HkGG

<400> SEQUENCE: 124
tcgatgaggt tgcctccctt atgcaccttg gccagac        37

<210> SEQ ID NO 125
<211> LENGTH: 37
<212> TYPE: DNA
<213> ORGANISM: Artificial Sequence
<220> FEATURE:
<223> OTHER INFORMATION: Primer A18A.HmGG

<400> SEQUENCE: 125
gtctggccaa ggtgcatatg ggaggcaacc tcatcga        37

<210> SEQ ID NO 126
<211> LENGTH: 37
<212> TYPE: DNA
<213> ORGANISM: Artificial Sequence
<220> FEATURE:
<223> OTHER INFORMATION: Primer A18B.HmGG

<400> SEQUENCE: 126
tcgatgaggt tgcctcccat atgcaccttg gccagac        37

<210> SEQ ID NO 127
<211> LENGTH: 37
<212> TYPE: DNA
<213> ORGANISM: Artificial Sequence
<220> FEATURE:
<223> OTHER INFORMATION: Primer A19A.HfGG

<400> SEQUENCE: 127
gtctggccaa ggtgcatttc ggaggcaacc tcatcga        37

<210> SEQ ID NO 128
<211> LENGTH: 37
<212> TYPE: DNA
<213> ORGANISM: Artificial Sequence
<220> FEATURE:
<223> OTHER INFORMATION: Primer A19B.HfGG

<400> SEQUENCE: 128
tcgatgaggt tgcctccgaa atgcaccttg gccagac        37

<210> SEQ ID NO 129
<211> LENGTH: 37
<212> TYPE: DNA
<213> ORGANISM: Artificial Sequence
<220> FEATURE:
<223> OTHER INFORMATION: Primer A20A.HsGG

<400> SEQUENCE: 129
gtctggccaa ggtgcattcc ggaggcaacc tcatcga        37

<210> SEQ ID NO 130
<211> LENGTH: 37
<212> TYPE: DNA
<213> ORGANISM: Artificial Sequence
<220> FEATURE:
<223> OTHER INFORMATION: Primer A20B.HsGG

<400> SEQUENCE: 130
tcgatgaggt tgcctccgga atgcaccttg gccagac        37

<210> SEQ ID NO 131
<211> LENGTH: 37
<212> TYPE: DNA
<213> ORGANISM: Artificial Sequence
<220> FEATURE:
<223> OTHER INFORMATION: Primer A37A.HtGG

<400> SEQUENCE: 131
gtctggccaa ggtgcatacc ggaggcaacc tcatcga        37

<210> SEQ ID NO 132
<211> LENGTH: 37
<212> TYPE: DNA
<213> ORGANISM: Artificial Sequence
<220> FEATURE:
<223> OTHER INFORMATION: Primer A37B.HtGG

<400> SEQUENCE: 132
tcgatgaggt tgcctccggt atgcaccttg gccagac        37

<210> SEQ ID NO 133
<211> LENGTH: 37
<212> TYPE: DNA
<213> ORGANISM: Artificial Sequence
<220> FEATURE:
<223> OTHER INFORMATION: Primer A38A.HwGG

<400> SEQUENCE: 133

```
gtctggccaa ggtgcattgg ggaggcaacc tcatcga                              37
```

<210> SEQ ID NO 134
<211> LENGTH: 37
<212> TYPE: DNA
<213> ORGANISM: Artificial Sequence
<220> FEATURE:
<223> OTHER INFORMATION: Primer A38B.HwGG

<400> SEQUENCE: 134

```
tcgatgaggt tgcctcccca atgcaccttg gccagac                              37
```

<210> SEQ ID NO 135
<211> LENGTH: 37
<212> TYPE: DNA
<213> ORGANISM: Artificial Sequence
<220> FEATURE:
<223> OTHER INFORMATION: Primer A21A.HyGG

<400> SEQUENCE: 135

```
gtctggccaa ggtgcattac ggaggcaacc tcatcga                              37
```

<210> SEQ ID NO 136
<211> LENGTH: 37
<212> TYPE: DNA
<213> ORGANISM: Artificial Sequence
<220> FEATURE:
<223> OTHER INFORMATION: Primer A21B.HyGG

<400> SEQUENCE: 136

```
tcgatgaggt tgcctccgta atgcaccttg gccagac                              37
```

<210> SEQ ID NO 137
<211> LENGTH: 37
<212> TYPE: DNA
<213> ORGANISM: Artificial Sequence
<220> FEATURE:
<223> OTHER INFORMATION: Primer A22A.HvGG

<400> SEQUENCE: 137

```
gtctggccaa ggtgcatgtc ggaggcaacc tcatcga                              37
```

<210> SEQ ID NO 138
<211> LENGTH: 37
<212> TYPE: DNA
<213> ORGANISM: Artificial Sequence
<220> FEATURE:
<223> OTHER INFORMATION: Primer A22B.HvGG

<400> SEQUENCE: 138

```
tcgatgaggt tgcctccgac atgcaccttg gccagac                              37
```

<210> SEQ ID NO 139
<211> LENGTH: 454
<212> TYPE: PRT
<213> ORGANISM: Euglena anabaena UTEX 373

<400> SEQUENCE: 139

```
Met Ala Thr Ile Ser Leu Thr Thr Glu Gln Leu Leu Glu His Pro Glu
1               5                   10                  15

Leu Val Ala Ile Asp Gly Val Leu Tyr Asp Leu Phe Gly Leu Ala Lys
            20                  25                  30

Val His Cys Gly Gly Asn Leu Ile Glu Ala Ala Gly Ala Ser Asp Gly
        35                  40                  45
```

-continued

Thr Ala Leu Phe Tyr Ser Met His Pro Gly Val Lys Pro Glu Asn Ser
 50                  55                  60

Lys Leu Leu Gln Gln Phe Ala Arg Gly Lys His Glu Arg Ser Ser Lys
 65                  70                  75                  80

Asp Pro Val Tyr Thr Phe Asp Ser Pro Phe Ala Gln Asp Val Lys Gln
                     85                  90                  95

Ser Val Arg Glu Val Met Lys Gly Arg Asn Trp Tyr Ala Thr Pro Gly
                 100                 105                 110

Phe Trp Leu Arg Thr Ala Leu Ile Ile Ala Cys Thr Ala Ile Gly Glu
             115                 120                 125

Trp Tyr Trp Ile Thr Thr Gly Ala Val Met Trp Gly Ile Phe Thr Gly
         130                 135                 140

Tyr Phe His Ser Gln Ile Gly Leu Ala Ile Gln His Asp Ala Ser His
145                 150                 155                 160

Gly Ala Ile Ser Lys Lys Pro Trp Val Asn Ala Phe Phe Ala Tyr Gly
                 165                 170                 175

Ile Asp Ala Ile Gly Ser Ser Arg Trp Ile Trp Leu Gln Ser His Ile
             180                 185                 190

Met Arg His His Thr Tyr Thr Asn Gln His Gly Leu Asp Leu Asp Ala
         195                 200                 205

Ala Ser Ala Glu Pro Phe Ile Leu Phe His Ser Tyr Pro Ala Thr Asn
210                 215                 220

Ala Ser Arg Lys Trp Tyr His Arg Phe Gln Ala Trp Tyr Met Tyr Ile
225                 230                 235                 240

Val Leu Gly Met Tyr Gly Val Ser Met Val Tyr Asn Pro Met Tyr Leu
                 245                 250                 255

Phe Thr Met Gln His Asn Asp Thr Ile Pro Glu Ala Thr Ser Leu Arg
             260                 265                 270

Pro Gly Ser Phe Phe Asn Arg Gln Arg Ala Phe Ala Val Ser Leu Arg
         275                 280                 285

Leu Leu Phe Ile Phe Arg Asn Ala Phe Leu Pro Trp Tyr Ile Ala Gly
     290                 295                 300

Ala Ser Pro Leu Leu Thr Ile Leu Leu Val Pro Thr Val Thr Gly Ile
305                 310                 315                 320

Phe Leu Thr Phe Val Phe Val Leu Ser His Asn Phe Glu Gly Ala Glu
                 325                 330                 335

Arg Thr Pro Glu Lys Asn Cys Lys Ala Lys Arg Ala Lys Glu Gly Lys
             340                 345                 350

Glu Val Arg Asp Val Glu Asp Arg Val Asp Trp Tyr Arg Ala Gln
         355                 360                 365

Ala Glu Thr Ala Ala Thr Tyr Gly Gly Ser Val Gly Met Met Leu Thr
370                 375                 380

Gly Gly Leu Asn Leu Gln Ile Glu His His Leu Phe Pro Arg Met Ser
385                 390                 395                 400

Ser Trp His Tyr Pro Phe Ile Gln Asp Thr Val Arg Glu Cys Cys Lys
                 405                 410                 415

Arg His Gly Val Arg Tyr Thr Tyr Tyr Pro Thr Ile Leu Glu Asn Ile
             420                 425                 430

Met Ser Thr Leu Arg Tyr Met Gln Lys Val Gly Val Ala His Thr Ile
         435                 440                 445

Gln Asp Ala Gln Glu Phe
450

<210> SEQ ID NO 140

<211> LENGTH: 8480
<212> TYPE: DNA
<213> ORGANISM: Artificial Sequence
<220> FEATURE:
<223> OTHER INFORMATION: Plasmid pZURD5S

<400> SEQUENCE: 140

```
catggctccc gacgccgaca agctgcgaca gcgaaaggct cagtccatcc aggacactgc        60
cgattctcag gctaccgagc tcaagattgg caccctgaag ggtctccaag gcaccgagat       120
cgtcattgat ggcgacatct acgacatcaa agacttcgat caccctggag gcgaatccat       180
catgaccttt ggtggcaacg acgttactgc cacctacaag atgattcatc cctaccactc       240
gaagcatcac ctggagaaga tgaaaaaggt cggtcgagtg cccgactaca cctccgagta       300
caagttcgat actcccttcg aacgagagat caaacaggag gtcttcaaga ttgtgcgaag       360
aggtcgagag tttggaacac ctggctactt ctttcgagcc ttctgctaca tcggtctctt       420
cttttacctg cagtatctct gggttaccac tcctaccact ttcgcccttg ctatcttcta       480
cggtgtgtct caggccttca ttggcctgaa cgtccagcac gacgccaacc acggagctgc       540
ctccaaaaag ccctggatca acaatttgct cggcctgggt gccgacttta tcggaggctc       600
caagtggctc tggatgaacc agcactggac ccatcacact tacaccaacc atcacgagaa       660
ggatcccgac gccctgggtg cagagcctat gctgctcttc aacgactatc ccttgggtca       720
ccccaagcga accctcattc atcacttcca agccttctac tatctgtttg tccttgctgg       780
ctactgggtg tcttcggtgt tcaaccctca gatcctggac ctccagcacc gaggtgccca       840
ggctgtcggc atgaagatgg agaacgacta cattgccaag tctcgaaagt acgctatctt       900
cctgcgactc ctgtacatct acaccaacat tgtggctccc atccgagaacc aaggcttttc       960
gctcaccgtc gttgctcaca ttcttactat gggtgtcgcc tccagcctga ccctcgctac      1020
tctgttcgcc ctctcccaca acttcgaaaa cgcagatcgg gatccacctt acgaggctcg      1080
aaagggaggc gagcctgtct gttggttcaa gtcgcaggtg gaaacctcct ctacttacgg      1140
tggcttcatt tccggttgcc ttacaggcgg actcaacttt caggtcgagc atcacctgtt      1200
tcctcgaatg tcctctgcct ggtacccta catcgctcct accgttcgag aggtctgcaa      1260
aaagcacggc gtcaagtacg cctactatcc ctgggtgtgg cagaacctca tctcgaccgt      1320
caagtacctg catcagtccg gaactggctc gaactggaag aacggtgcca atccctactc      1380
tggcaagctg taagcggccg caagtgtgga tggggaagtg agtgcccggt tctgtgtgca      1440
caattggcaa tccaagatgg atggattcaa cacaggata tagcgagcta cgtggtggtg      1500
cgaggatata gcaacggata tttatgttg acacttgaga atgtacgata caagcactgt      1560
ccaagtacaa tactaaacat actgtacata ctcatactcg tacccgggca acggtttcac      1620
ttgagtgcag tggctagtgc tcttactcgt acagtgtgca atactgcgta tcatagtctt      1680
tgatgtatat cgtattcatt catgttagtt gcgtacgagc cggaagcata agtgtaaag       1740
cctggggtgc ctaatgagtg agctaactca cattaattgc gttgcgctca ctgcccgctt      1800
tccagtcggg aaacctgtcg tgccagctgc attaatgaat cggccaacgc gcggggagag      1860
gcggtttgcg tattgggcgc tcttccgctt cctcgctcac tgactcgctg cgctcggtcg      1920
ttcggctgcg gcgagcggta tcagctcact caaaggcggt aatacggtta tccacagaat      1980
caggggataa cgcaggaaag aacatgtgag caaaaggcca gcaaaaggcc aggaaccgta      2040
aaaaggccgc gttgctggcg ttttccata ggctccgccc ccctgacgag catcacaaaa       2100
atcgacgctc aagtcagagg tggcgaaacc cgacaggact ataaagatac caggcgtttc      2160
```

```
cccctggaag ctccctcgtg cgctctcctg ttccgaccct gccgcttacc ggatacctgt    2220
ccgcctttct cccttcggga agcgtggcgc tttctcatag ctcacgctgt aggtatctca    2280
gttcggtgta ggtcgttcgc tccaagctgg gctgtgtgca cgaaccccc gttcagcccg     2340
accgctgcgc cttatccggt aactatcgtc ttgagtccaa cccggtaaga cacgacttat    2400
cgccactggc agcagccact ggtaacagga ttagcagagc gaggtatgta ggcggtgcta    2460
cagagttctt gaagtggtgg cctaactacg gctacactag aaggacagta tttggtatct    2520
gcgctctgct gaagccagtt accttcggaa aaagagttgg tagctcttga tccggcaaac    2580
aaaccaccgc tggtagcggt ggttttttg tttgcaagca gcagattacg cgcagaaaaa     2640
aaggatctca agaagatcct ttgatctttt ctacgggtc tgacgctcag tggaacgaaa     2700
actcacgtta agggatttg gtcatgagat tatcaaaaag gatcttcacc tagatccttt     2760
taaattaaaa atgaagtttt aaatcaatct aaagtatata tgagtaaact tggtctgaca    2820
gttaccaatg cttaatcagt gaggcaccta tctcagcgat ctgtctattt cgttcatcca    2880
tagttgcctg actccccgtc gtgtagataa ctacgatacg ggagggctta ccatctggcc    2940
ccagtgctgc aatgataccg cgagacccac gctcaccggc tccagattta tcagcaataa    3000
accagccagc cggaagggcc gagcgcagaa gtggtcctgc aactttatcc gcctccatcc    3060
agtctattaa ttgttgccgg gaagctgag taagtagttc gccagttaat agtttgcgca     3120
acgttgttgc cattgctaca ggcatcgtgg tgtcacgctc gtcgtttggt atggcttcat    3180
tcagctccgg ttcccaacga tcaaggcgag ttacatgatc ccccatgttg tgcaaaaaag    3240
cggttagctc cttcggtcct ccgatcgttg tcagaagtaa gttggccgca gtgttatcac    3300
tcatggttat ggcagcactg cataattctc ttactgtcat gccatccgta agatgctttt    3360
ctgtgactgg tgagtactca accaagtcat tctgagaata gtgtatgcgg cgaccgagtt    3420
gctcttgccc ggcgtcaata cgggataata ccgcgccaca tagcagaact ttaaaagtgc    3480
tcatcattgg aaaacgttct cggggcgaaa actctcaag gatcttaccg ctgttgagat     3540
ccagttcgat gtaacccact cgtgcaccca actgatcttc agcatctttt actttcacca    3600
gcgtttctgg gtgagcaaaa acaggaaggc aaaatgccgc aaaaaaggga ataagggcga    3660
cacggaaatg ttgaatactc atactcttcc tttttcaata ttattgaagc atttatcagg    3720
gttattgtct catgagcgga tacatatttg aatgtattta gaaaaataaa caaatagggg    3780
ttccgcgcac atttccccga aaagtgccac ctgacgcgcc ctgtagcggc gcattaagcg    3840
cggcgggtgt ggtggttacg cgcagcgtga ccgctacact tgccagcgcc ctagcgcccg    3900
ctcctttcgc tttcttccct tcctttctcg ccacgttcgc cggctttccc cgtcaagctc    3960
taaatcgggg gctccctta gggttccgat ttagtgcttt acggcacctc gaccccaaaa    4020
aacttgatta gggtgatggt tcacgtagtg ggccatcgcc ctgatagacg gttttcgcc    4080
ctttgacgtt ggagtccacg ttctttaata gtggactctt gttccaaact ggaacaacac    4140
tcaaccctat ctcggtctat tcttttgatt tataagggat tttgccgatt tcggcctatt    4200
ggttaaaaaa tgagctgatt taacaaaaat ttaacgcgaa ttttaacaaa atattaacgc    4260
ttacaatttc cattcgccat tcaggctgcg caactgttgg aagggcgat cggtgcgggc     4320
ctcttcgcta ttacgccagc tggcgaaagg gggatgtgct gcaaggcgat taagttgggt    4380
aacgccaggg ttttcccagt cacgacgttg taaaacgacg gccagtgaat tgtaatacga    4440
ctcactatag ggcgaattgg gtaccggggcc cccctcgag gtcgatggtg tcgataagct    4500
tgatatcgaa ttcatgtcac acaaaccgat cttcgcctca aggaaaccta attctacatc    4560
```

```
cgagagactg ccgagatcca gtctacactg attaattttc gggccaataa tttaaaaaaa   4620
tcgtgttata taatattata tgtattatat atatacatca tgatgatact gacagtcatg   4680
tcccattgct aaatagacag actccatctg ccgcctccaa ctgatgttct caatatttaa   4740
ggggtcatct cgcattgttt aataataaac agactccatc taccgcctcc aaatgatgtt   4800
ctcaaaatat attgtatgaa cttatttttt ttacttagta ttattagaca acttacttgc   4860
tttatgaaaa acacttccta tttaggaaac aatttataat ggcagttcgt tcatttaaca   4920
atttatgtag aataaatgtt ataaatgcgt atgggaaatc ttaaatatgg atagcataaa   4980
tgatatctgc attgcctaat tcgaaatcaa cagcaacgaa aaaaatccct tgtacaacat   5040
aaatagtcat cgagaaatat caactatcaa agaacagcta ttcacacgtt actattgaga   5100
ttattattgg acgagaatca cacactcaac tgtctttctc tcttctagaa atacaggtac   5160
aagtatgtac tattctcatt gttcatactt ctagtcattt catcccacat attccttgga   5220
tttctctcca atgaatgaca ttctatcttg caaattcaac aattataata agatatacca   5280
aagtagcggt atagtggcaa tcaaaaagct tctctggtgt gcttctcgta tttatttta    5340 ttctaatgat ccattaaagg tatatattta ttcttgtta tataatcctt ttgtttatta    5400
catgggctgg atacataaag gtattttgat ttaatttttt gcttaaattc aatcccccct   5460
cgttcagtgt caactgtaat ggtaggaaat taccatactt ttgaagaagc aaaaaaaatg   5520
aaagaaaaaa aaaatcgtat ttccaggtta gacgttccgc agaatctaga atgcggtatg   5580
cggtacattg ttcttcgaac gtaaaagttg cgctccctga gatattgtac atttttgctt   5640
ttacaagtac aagtacatcg tacaactatg tactactgtt gatgcatcca caacagtttg   5700
ttttgttttt ttttgttttt tttttttcta atgattcatt accgctatgt atacctactt   5760
gtacttgtag taagccgggt tattggcgtt caattaatca tagacttatg aatctgcacg   5820
gtgtgcgctg cgagttactt ttagcttatg catgctactt gggtgtaata ttgggatctg   5880
ttcggaaatc aacggatgct caatcgattt cgacagtaat taattaagtc atacacaagt   5940 cagcttctt cgagcctcat ataagtataa gtagttcaac gtattagcac tgtacccagc    6000
atctccgtat cgagaaacac aacaacatgc cccattggac agatcatgcg gatacacagg   6060
ttgtgcagta tcatacatac tcgatcagac aggtcgtctg accatcatac aagctgaaca   6120
agcgctccat acttgcacgc tctctatata cacagttaaa ttacatatcc atagtctaac   6180
ctctaacagt taatcttctg gtaagcctcc cagccagcct tctggtatcg cttggcctcc   6240
tcaataggat ctcggttctg gccgtacaga cctcggccga caattatgat atccgttccg   6300
gtagacatga catcctcaac agttcggtac tgctgtccga gagcgtctcc cttgtcgtca   6360
agacccaccc cggggtcag aataagccag tcctcagagt cgcccttagg tcggttctgg    6420
gcaatgaagc caaccacaaa ctcggggtcg gatcgggcaa gctcaatggt ctgcttggag   6480
tactcgccag tggccagaga gcccttgcaa gacagctcgg ccagcatgag cagacctctg   6540
gccagcttct cgttgggaga ggggactagg aactccttgt actgggagtt ctcgtagtca   6600
gagacgtcct ccttcttctg ttcagagaca gtttcctcgg caccagctcg caggccagca   6660
atgattccgg ttccgggtac accgtgggcg ttggtgatat cggaccactc ggcgattcgg   6720
tgacaccggt actggtgctt gacagtgttg ccaatatctg cgaactttct gtcctcgaac   6780
aggaagaaac cgtgcttaag agcaagttcc ttgagggga gcacagtgcc ggcgtaggtg    6840
aagtcgtcaa tgatgtcgat atgggttttg atcatgcaca cataaggtcc gaccttatcg   6900
gcaagctcaa tgagctcctt ggtggtggta acatccagag aagcacacag gttggttttc   6960
```

```
ttggctgcca cgagcttgag cactcgagcg gcaaaggcgg acttgtggac gttagctcga    7020
gcttcgtagg agggcatttt ggtggtgaag aggagactga aataaattta gtctgcagaa    7080
cttttatcg gaaccttatc tggggcagtg aagtatatgt tatggtaata gttacgagtt    7140
agttgaactt atagatagac tggactatac ggctatcggt ccaaattaga agaacgtca     7200
atggctctct gggcgtcgcc tttgccgaca aaatgtgat catgatgaaa gccagcaatg     7260
acgttgcagc tgatattgtt gtcggccaac cgcgccgaaa acgcagctgt cagacccaca    7320
gcctccaacg aagaatgtat cgtcaaagtg atccaagcac actcatagtt ggagtcgtac    7380
tccaaaggcg gcaatgacga gtcagacaga tactcgtcga ctcaggcgac gacgaattc     7440
ctgcagccca tctgcagaat tcaggagaga ccgggttggc ggcgtatttg tgtcccaaaa    7500
aacagcccca attgccccgg agaagacggc caggccgcct agatgacaaa ttcaacaact    7560
cacagctgac tttctgccat tgccactagg gggggccctt tttatatggc caagccaagc    7620
tctccacgtc ggttgggctg cacccaacaa taaatgggta gggttgcacc aacaaaggga    7680
tgggatgggg ggtagaagat acgaggataa cggggctcaa tggcacaaat aagaacgaat    7740
actgccatta agactcgtga tccagcgact gacaccattg catcatctaa gggcctcaaa    7800
actacctcgg aactgctgcg ctgatctgga caccacagag gttccgagca ctttaggttg    7860
caccaaatgt cccaccaggt gcaggcagaa aacgctggaa cagcgtgtac agtttgtctt    7920
aacaaaaagt gagggcgctg aggtcgagca gggtggtgtg acttgttata gcctttagag    7980
ctgcgaaagc gcgtatggat ttggctcatc aggccagatt gagggtctgt ggacacatgt    8040
catgttagtg tacttcaatc gcccctgga tatagccccg acaataggcc gtggcctcat     8100
tttttgcct tccgcacatt tccattgctc ggtacccaca ccttgcttct cctgcacttg     8160
ccaaccttaa tactggttta cattgaccaa catcttacaa gcgggggct tgtctagggt     8220
atatataaac agtggctctc ccaatcggtt gccagtctct ttttctttt ctttccccac    8280
agattcgaaa tctaaactac acatcacaca atgcctgtta ctgacgtcct taagcgaaag    8340
tccggtgtca tcgtcggcga cgatgtccga gccgtgagta tccacgacaa gatcagtgtc    8400
gagacgacgc gttttgtgta atgacacaat ccgaaagtcg ctagcaacac acactctcta    8460
cacaaactaa cccagctctc                                                8480
```

```
<210> SEQ ID NO 141
<211> LENGTH: 36
<212> TYPE: DNA
<213> ORGANISM: Artificial Sequence
<220> FEATURE:
<223> OTHER INFORMATION: Primer R5-10A.HaGG

<400> SEQUENCE: 141
caaagacttc gatcacgccg gaggcgaatc catcat                               36

<210> SEQ ID NO 142
<211> LENGTH: 36
<212> TYPE: DNA
<213> ORGANISM: Artificial Sequence
<220> FEATURE:
<223> OTHER INFORMATION: Primer R5-10B.HaGG

<400> SEQUENCE: 142
atgatggatt cgcctccggc gtgatcgaag tctttg                               36

<210> SEQ ID NO 143
<211> LENGTH: 36
<212> TYPE: DNA
```

```
<213> ORGANISM: Artificial Sequence
<220> FEATURE:
<223> OTHER INFORMATION: Primer R5-11A.HrGG

<400> SEQUENCE: 143
caaagacttc gatcaccgag gaggcgaatc catcat                                  36

<210> SEQ ID NO 144
<211> LENGTH: 36
<212> TYPE: DNA
<213> ORGANISM: Artificial Sequence
<220> FEATURE:
<223> OTHER INFORMATION: Primer R5-11B.HrGG

<400> SEQUENCE: 144
atgatggatt cgcctcctcg gtgatcgaag tctttg                                  36

<210> SEQ ID NO 145
<211> LENGTH: 36
<212> TYPE: DNA
<213> ORGANISM: Artificial Sequence
<220> FEATURE:
<223> OTHER INFORMATION: Primer R5-12A.HnGG

<400> SEQUENCE: 145
caaagacttc gatcacaacg gaggcgaatc catcat                                  36

<210> SEQ ID NO 146
<211> LENGTH: 36
<212> TYPE: DNA
<213> ORGANISM: Artificial Sequence
<220> FEATURE:
<223> OTHER INFORMATION: Primer R5-12B.HnGG

<400> SEQUENCE: 146
atgatggatt cgcctccgtt gtgatcgaag tctttg                                  36

<210> SEQ ID NO 147
<211> LENGTH: 36
<212> TYPE: DNA
<213> ORGANISM: Artificial Sequence
<220> FEATURE:
<223> OTHER INFORMATION: Primer R5-33A.HdGG

<400> SEQUENCE: 147
caaagacttc gatcacgacg gaggcgaatc catcat                                  36

<210> SEQ ID NO 148
<211> LENGTH: 36
<212> TYPE: DNA
<213> ORGANISM: Artificial Sequence
<220> FEATURE:
<223> OTHER INFORMATION: Primer R5-33B.HdGG

<400> SEQUENCE: 148
atgatggatt cgcctccgtc gtgatcgaag tctttg                                  36

<210> SEQ ID NO 149
<211> LENGTH: 36
<212> TYPE: DNA
<213> ORGANISM: Artificial Sequence
<220> FEATURE:
<223> OTHER INFORMATION: Primer R5-34A.HcGG

<400> SEQUENCE: 149
caaagacttc gatcactgcg gaggcgaatc catcat                                  36
```

```
<210> SEQ ID NO 150
<211> LENGTH: 36
<212> TYPE: DNA
<213> ORGANISM: Artificial Sequence
<220> FEATURE:
<223> OTHER INFORMATION: Primer R5-34B.HcGG

<400> SEQUENCE: 150
atgatggatt cgcctccgca gtgatcgaag tctttg                                 36

<210> SEQ ID NO 151
<211> LENGTH: 36
<212> TYPE: DNA
<213> ORGANISM: Artificial Sequence
<220> FEATURE:
<223> OTHER INFORMATION: Primer R5-35A.HqGG

<400> SEQUENCE: 151
caaagacttc gatcaccagg gaggcgaatc catcat                                 36

<210> SEQ ID NO 152
<211> LENGTH: 36
<212> TYPE: DNA
<213> ORGANISM: Artificial Sequence
<220> FEATURE:
<223> OTHER INFORMATION: Primer R5-35B.HqGG

<400> SEQUENCE: 152
atgatggatt cgcctccctg gtgatcgaag tctttg                                 36

<210> SEQ ID NO 153
<211> LENGTH: 36
<212> TYPE: DNA
<213> ORGANISM: Artificial Sequence
<220> FEATURE:
<223> OTHER INFORMATION: Primer R5-36A.HeGG

<400> SEQUENCE: 153
caaagacttc gatcacgagg gaggcgaatc catcat                                 36

<210> SEQ ID NO 154
<211> LENGTH: 36
<212> TYPE: DNA
<213> ORGANISM: Artificial Sequence
<220> FEATURE:
<223> OTHER INFORMATION: Primer R5-36B.HeGG

<400> SEQUENCE: 154
atgatggatt cgcctccctc gtgatcgaag tctttg                                 36

<210> SEQ ID NO 155
<211> LENGTH: 36
<212> TYPE: DNA
<213> ORGANISM: Artificial Sequence
<220> FEATURE:
<223> OTHER INFORMATION: Primer R5-13A.HgGG

<400> SEQUENCE: 155
caaagacttc gatcacggcg gaggcgaatc catcat                                 36

<210> SEQ ID NO 156
<211> LENGTH: 36
<212> TYPE: DNA
<213> ORGANISM: Artificial Sequence
<220> FEATURE:
<223> OTHER INFORMATION: Primer R5-13B.HgGG
```

```
<400> SEQUENCE: 156
atgatggatt cgcctccgcc gtgatcgaag tctttg                              36

<210> SEQ ID NO 157
<211> LENGTH: 36
<212> TYPE: DNA
<213> ORGANISM: Artificial Sequence
<220> FEATURE:
<223> OTHER INFORMATION: Primer R5-14A.HhGG

<400> SEQUENCE: 157
caaagacttc gatcaccacg gaggcgaatc catcat                              36

<210> SEQ ID NO 158
<211> LENGTH: 36
<212> TYPE: DNA
<213> ORGANISM: Artificial Sequence
<220> FEATURE:
<223> OTHER INFORMATION: Primer R5-14B.HhGG

<400> SEQUENCE: 158
atgatggatt cgcctccgtg gtgatcgaag tctttg                              36

<210> SEQ ID NO 159
<211> LENGTH: 36
<212> TYPE: DNA
<213> ORGANISM: Artificial Sequence
<220> FEATURE:
<223> OTHER INFORMATION: Primer R5-15A.HiGG

<400> SEQUENCE: 159
caaagacttc gatcacatcg gaggcgaatc catcat                              36

<210> SEQ ID NO 160
<211> LENGTH: 36
<212> TYPE: DNA
<213> ORGANISM: Artificial Sequence
<220> FEATURE:
<223> OTHER INFORMATION: Primer R5-15B.HiGG

<400> SEQUENCE: 160
atgatggatt cgcctccgat gtgatcgaag tctttg                              36

<210> SEQ ID NO 161
<211> LENGTH: 36
<212> TYPE: DNA
<213> ORGANISM: Artificial Sequence
<220> FEATURE:
<223> OTHER INFORMATION: Primer R5-16A.HlGG

<400> SEQUENCE: 161
caaagacttc gatcacctcg gaggcgaatc catcat                              36

<210> SEQ ID NO 162
<211> LENGTH: 36
<212> TYPE: DNA
<213> ORGANISM: Artificial Sequence
<220> FEATURE:
<223> OTHER INFORMATION: Primer R5-16B.HlGG

<400> SEQUENCE: 162
atgatggatt cgcctccgag gtgatcgaag tctttg                              36

<210> SEQ ID NO 163
<211> LENGTH: 36
<212> TYPE: DNA
```

<213> ORGANISM: Artificial Sequence
<220> FEATURE:
<223> OTHER INFORMATION: Primer R5-17A.HkGG

<400> SEQUENCE: 163
caaagacttc gatcacaagg gaggcgaatc catcat            36

<210> SEQ ID NO 164
<211> LENGTH: 36
<212> TYPE: DNA
<213> ORGANISM: Artificial Sequence
<220> FEATURE:
<223> OTHER INFORMATION: Primer R5-17B.HkGG

<400> SEQUENCE: 164
atgatggatt cgcctccctt gtgatcgaag tctttg            36

<210> SEQ ID NO 165
<211> LENGTH: 36
<212> TYPE: DNA
<213> ORGANISM: Artificial Sequence
<220> FEATURE:
<223> OTHER INFORMATION: Primer R5-18A.HmGG

<400> SEQUENCE: 165
caaagacttc gatcacatgg gaggcgaatc catcat            36

<210> SEQ ID NO 166
<211> LENGTH: 36
<212> TYPE: DNA
<213> ORGANISM: Artificial Sequence
<220> FEATURE:
<223> OTHER INFORMATION: Primer R5-18B.HmGG

<400> SEQUENCE: 166
atgatggatt cgcctcccat gtgatcgaag tctttg            36

<210> SEQ ID NO 167
<211> LENGTH: 36
<212> TYPE: DNA
<213> ORGANISM: Artificial Sequence
<220> FEATURE:
<223> OTHER INFORMATION: Primer R5-19A.HfGG

<400> SEQUENCE: 167
caaagacttc gatcacttcg gaggcgaatc catcat            36

<210> SEQ ID NO 168
<211> LENGTH: 36
<212> TYPE: DNA
<213> ORGANISM: Artificial Sequence
<220> FEATURE:
<223> OTHER INFORMATION: Primer R5-19B.HfGG

<400> SEQUENCE: 168
atgatggatt cgcctccgaa gtgatcgaag tctttg            36

<210> SEQ ID NO 169
<211> LENGTH: 36
<212> TYPE: DNA
<213> ORGANISM: Artificial Sequence
<220> FEATURE:
<223> OTHER INFORMATION: Primer R5-20A.HsGG

<400> SEQUENCE: 169
caaagacttc gatcactccg gaggcgaatc catcat            36

<210> SEQ ID NO 170
<211> LENGTH: 36
<212> TYPE: DNA
<213> ORGANISM: Artificial Sequence
<220> FEATURE:
<223> OTHER INFORMATION: Primer R5-20B.HsGG

<400> SEQUENCE: 170
atgatggatt cgcctccgga gtgatcgaag tctttg                     36

<210> SEQ ID NO 171
<211> LENGTH: 36
<212> TYPE: DNA
<213> ORGANISM: Artificial Sequence
<220> FEATURE:
<223> OTHER INFORMATION: Primer R5-37A.HtGG

<400> SEQUENCE: 171
caaagacttc gatcacaccg gaggcgaatc catcat                     36

<210> SEQ ID NO 172
<211> LENGTH: 36
<212> TYPE: DNA
<213> ORGANISM: Artificial Sequence
<220> FEATURE:
<223> OTHER INFORMATION: Primer R5-37B.HtGG

<400> SEQUENCE: 172
atgatggatt cgcctccggt gtgatcgaag tctttg                     36

<210> SEQ ID NO 173
<211> LENGTH: 36
<212> TYPE: DNA
<213> ORGANISM: Artificial Sequence
<220> FEATURE:
<223> OTHER INFORMATION: Primer R5-38A.HwGG

<400> SEQUENCE: 173
caaagacttc gatcactggg gaggcgaatc catcat                     36

<210> SEQ ID NO 174
<211> LENGTH: 36
<212> TYPE: DNA
<213> ORGANISM: Artificial Sequence
<220> FEATURE:
<223> OTHER INFORMATION: Primer R5-38B.HwGG

<400> SEQUENCE: 174
atgatggatt cgcctcccca gtgatcgaag tctttg                     36

<210> SEQ ID NO 175
<211> LENGTH: 36
<212> TYPE: DNA
<213> ORGANISM: Artificial Sequence
<220> FEATURE:
<223> OTHER INFORMATION: Primer R5-21A.HyGG

<400> SEQUENCE: 175
caaagacttc gatcactacg gaggcgaatc catcat                     36

<210> SEQ ID NO 176
<211> LENGTH: 36
<212> TYPE: DNA
<213> ORGANISM: Artificial Sequence
<220> FEATURE:
<223> OTHER INFORMATION: Primer R5-21B.HyGG -continued

```
<400> SEQUENCE: 176
atgatggatt cgcctccgta gtgatcgaag tctttg                                  36

<210> SEQ ID NO 177
<211> LENGTH: 36
<212> TYPE: DNA
<213> ORGANISM: Artificial Sequence
<220> FEATURE:
<223> OTHER INFORMATION: Primer R5-22A.HvGG

<400> SEQUENCE: 177
caaagacttc gatcacgtcg gaggcgaatc catcat                                  36

<210> SEQ ID NO 178
<211> LENGTH: 36
<212> TYPE: DNA
<213> ORGANISM: Artificial Sequence
<220> FEATURE:
<223> OTHER INFORMATION: Primer R5-22B.HvGG

<400> SEQUENCE: 178
atgatggatt cgcctccgac gtgatcgaag tctttg                                  36

<210> SEQ ID NO 179
<211> LENGTH: 463
<212> TYPE: PRT
<213> ORGANISM: Peridinium sp. CCMP626
<220> FEATURE:
<221> NAME/KEY: MISC_FEATURE
<222> LOCATION: (55)..(55)
<223> OTHER INFORMATION: Xaa = Cys (C) or Trp (W)

<400> SEQUENCE: 179
```

Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Xaa Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
    130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala

-continued

```
                210                 215                 220
Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Val Phe Asn Pro Gln Ile Leu
            260                 265                 270

Asp Leu Gln His Arg Gly Ala Gln Ala Val Gly Met Lys Met Glu Asn
                275                 280                 285

Asp Tyr Ile Ala Lys Ser Arg Lys Tyr Ala Ile Phe Leu Arg Leu Leu
290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
                340                 345                 350

Arg Asp Pro Thr Tyr Glu Ala Arg Lys Gly Gly Glu Pro Val Cys Trp
            355                 360                 365

Phe Lys Ser Gln Val Glu Thr Ser Ser Thr Tyr Gly Phe Ile Ser
370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
            405                 410                 415

Glu Val Cys Lys Lys His Gly Val Lys Tyr Ala Tyr Tyr Pro Trp Val
        420                 425                 430

Trp Gln Asn Leu Ile Ser Thr Val Lys Tyr Leu His Gln Ser Gly Thr
            435                 440                 445

Gly Ser Asn Trp Lys Asn Gly Ala Asn Pro Tyr Ser Gly Lys Leu
    450                 455                 460

<210> SEQ ID NO 180
<211> LENGTH: 4
<212> TYPE: PRT
<213> ORGANISM: Artificial Sequence
<220> FEATURE:
<223> OTHER INFORMATION: HPGG motif

<400> SEQUENCE: 180

His Pro Gly Gly
1

<210> SEQ ID NO 181
<211> LENGTH: 4
<212> TYPE: PRT
<213> ORGANISM: Artificial Sequence
<220> FEATURE:
<223> OTHER INFORMATION: HXGG motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 181

His Xaa Gly Gly
1

<210> SEQ ID NO 182
<211> LENGTH: 4
```

```
<212> TYPE: PRT
<213> ORGANISM: Artificial Sequence
<220> FEATURE:
<223> OTHER INFORMATION: HPGX motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 182

His Pro Gly Xaa
1

<210> SEQ ID NO 183
<211> LENGTH: 4
<212> TYPE: PRT
<213> ORGANISM: Artificial Sequence
<220> FEATURE:
<223> OTHER INFORMATION: HGGG motif

<400> SEQUENCE: 183

His Gly Gly Gly
1

<210> SEQ ID NO 184
<211> LENGTH: 4
<212> TYPE: PRT
<213> ORGANISM: Artificial Sequence
<220> FEATURE:
<223> OTHER INFORMATION: HHGG motif

<400> SEQUENCE: 184

His His Gly Gly
1

<210> SEQ ID NO 185
<211> LENGTH: 4
<212> TYPE: PRT
<213> ORGANISM: Artificial Sequence
<220> FEATURE:
<223> OTHER INFORMATION: HPGS motif

<400> SEQUENCE: 185

His Pro Gly Ser
1

<210> SEQ ID NO 186
<211> LENGTH: 4
<212> TYPE: PRT
<213> ORGANISM: Artificial Sequence
<220> FEATURE:
<223> OTHER INFORMATION: HCGG motif

<400> SEQUENCE: 186

His Cys Gly Gly
1

<210> SEQ ID NO 187
<211> LENGTH: 4
<212> TYPE: PRT
<213> ORGANISM: Artificial Sequence
<220> FEATURE:
<223> OTHER INFORMATION: HWGG motif

<400> SEQUENCE: 187

His Trp Gly Gly
1
```

```
<210> SEQ ID NO 188
<211> LENGTH: 4
<212> TYPE: PRT
<213> ORGANISM: Artificial Sequence
<220> FEATURE:
<223> OTHER INFORMATION: HAGG motif

<400> SEQUENCE: 188

His Ala Gly Gly
1

<210> SEQ ID NO 189
<211> LENGTH: 4
<212> TYPE: PRT
<213> ORGANISM: Artificial Sequence
<220> FEATURE:
<223> OTHER INFORMATION: HPGA motif

<400> SEQUENCE: 189

His Pro Gly Ala
1

<210> SEQ ID NO 190
<211> LENGTH: 1350
<212> TYPE: DNA
<213> ORGANISM: Euglena gracilis

<400> SEQUENCE: 190
atggctctct cccttactac cgagcagctg ctcgagcgac ccgacctggt tgccatcgac       60
ggcattctct acgatctgga aggtcttgcc aaggtccatg gtggaggcga cttgatcctc      120
gcttctggtg cctccgatgc ttctcctctg ttctactcca tgcacccttacgtcaagccc      180 gagaactcga agctgcttca acagttcgtg cgaggcaagc acgaccgaac ctccaaggac      240
attgtctaca cctacgactc tcccttttgca caggacgtca agcgaactat gcgagaggtc      300
atgaaaggtc ggaactggta tgccacacct ggattctggc tgcgaaccgt tggcatcatt      360
gctgtcaccg ccttttgcga gtggcactgg gctactaccg gaatggtgct gtggggtctc      420
ttgactggat tcatgcacat gcagatcggc ctgtccattc agcacgatgc ctctcatggt      480
gccatcagca aaaagccctg ggtcaacgct ctctttgcct acggcatcga cgtcattgga      540
tcgtccagat ggatctggct gcagtctcac atcatgcgac atcacaccta ccaatcag      600 catggtctcg acctggatgc cgagtccgca gaaccattcc ttgtgttcca caactaccct      660
gctgccaaca ctgctcgaaa gtggtttcac cgattccagg cctggtacat gtacctcgtg      720
cttggagcct acggcgtttc gctggtgtac aaccctctct acatcttccg aatgcagcac      780
aacgacacca ttcccgagtc tgtcacagcc atgcgagaga acggctttct gcgacggtac      840
cgaacccttg cattcgttat gcgagctttc ttcatctttc gaaccgcctt cttgccctgg      900
tatctcactg gaacctcccct gctcatcacc attcctctgg tgcccactgc taccggtgcc      960
ttcctcacct tctttttcat cttgtctcac aacttcgatg gctcggagcg aatccccgac     1020
aagaactgca aggtcaagag ctccgagaag gacgttgaag ccgatcagat cgactggtac     1080
agagctcagg tggagacctc ttccacctac ggtggaccca ttgccatgtt ctttactggc     1140
ggtctcaact tccagatcga gcatcacctc tttcctcgaa tgtcgtcttg cactatccc      1200 ttcgtgcagc aagctgtccg agagtgttgc gaacgacacg gagttcggta cgtcttctac     1260
cctaccattg tgggcaacat catttccacc ctcaagtaca tgcacaaagt cggtgtggtt     1320
cactgtgtca aggacgctca ggattcctaa                                     1350
```

<210> SEQ ID NO 191
<211> LENGTH: 1350
<212> TYPE: DNA
<213> ORGANISM: Euglena gracilis

<400> SEQUENCE: 191

| | | | | | |
|---|---|---|---|---|---|
| atggctctct | cccttactac | cgagcagctg | ctcgagcgac | ccgacctggt | tgccatcgac | 60 |
| ggcattctct | acgatctgga | aggtcttgcc | aaggtccatc | acggaggcga | cttgatcctc | 120 |
| gcttctggtg | cctccgatgc | ttctcctctg | ttctactcca | tgcacccttta | cgtcaagccc | 180 |
| gagaactcga | agctgcttca | acagttcgtg | cgaggcaagc | acgaccgaac | ctccaaggac | 240 |
| attgtctaca | cctacgactc | tcccttgca | caggacgtca | agcgaactat | gcgagaggtc | 300 |
| atgaaaggtc | ggaactggta | tgccacacct | ggattctggc | tgcgaaccgt | tggcatcatt | 360 |
| gctgtcaccg | cctttgcga | gtggcactgg | gctactaccg | gaatggtgct | gtggggtctc | 420 |
| ttgactggat | tcatgcacat | gcagatcggc | ctgtccattc | agcacgatgc | ctctcatggt | 480 |
| gccatcagca | aaaagccctg | ggtcaacgct | ctctttgcct | acggcatcga | cgtcattgga | 540 |
| tcgtccagat | ggatctggct | gcagtctcac | atcatgcgac | atcacaccta | caccaatcag | 600 |
| catggtctcg | acctggatgc | cgagtccgca | gaaccattcc | ttgtgttcca | caactaccct | 660 |
| gctgccaaca | ctgctcgaaa | gtggtttcac | cgattccagg | cctggtacat | gtacctcgtg | 720 |
| cttggagcct | acggcgtttc | gctggtgtac | aaccctctct | acatcttccg | aatgcagcac | 780 |
| aacgacacca | ttcccgagtc | tgtcacagcc | atgcgagaga | cggctttct | gcgacggtac | 840 |
| cgaacccttg | cattcgttat | gcgagctttc | ttcatctttc | gaaccgcctt | cttgccctgg | 900 |
| tatctcactg | gaacctccct | gctcatcacc | attcctctgg | tgcccactgc | taccggtgcc | 960 |
| ttcctcacct | tcttttttcat | cttgtctcac | aacttcgatg | gctcggagcg | aatccccgac | 1020 |
| aagaactgca | aggtcaagag | ctccgagaag | gacgttgaag | ccgatcagat | cgactggtac | 1080 |
| agagctcagg | tggagacctc | ttccacctac | ggtggaccca | ttgccatgtt | ctttactggc | 1140 |
| ggtctcaact | tccagatcga | gcatcacctc | tttcctcgaa | tgtcgtcttg | gcactatccc | 1200 |
| ttcgtgcagc | aagctgtccg | agagtgttgc | gaacgacacg | gagttcggta | cgtcttctac | 1260 |
| cctaccattg | tgggcaacat | catttccacc | ctcaagtaca | tgcacaaagt | cggtgtggtt | 1320 |
| cactgtgtca | aggacgctca | ggattcctaa | | | | 1350 |

<210> SEQ ID NO 192
<211> LENGTH: 1350
<212> TYPE: DNA
<213> ORGANISM: Euglena gracilis

<400> SEQUENCE: 192

| | | | | | |
|---|---|---|---|---|---|
| atggctctct | cccttactac | cgagcagctg | ctcgagcgac | ccgacctggt | tgccatcgac | 60 |
| ggcattctct | acgatctgga | aggtcttgcc | aaggtccatc | ccggatccga | cttgatcctc | 120 |
| gcttctggtg | cctccgatgc | ttctcctctg | ttctactcca | tgcacccttta | cgtcaagccc | 180 |
| gagaactcga | agctgcttca | acagttcgtg | cgaggcaagc | acgaccgaac | ctccaaggac | 240 |
| attgtctaca | cctacgactc | tcccttgca | caggacgtca | agcgaactat | gcgagaggtc | 300 |
| atgaaaggtc | ggaactggta | tgccacacct | ggattctggc | tgcgaaccgt | tggcatcatt | 360 |
| gctgtcaccg | cctttgcga | gtggcactgg | gctactaccg | gaatggtgct | gtggggtctc | 420 |
| ttgactggat | tcatgcacat | gcagatcggc | ctgtccattc | agcacgatgc | ctctcatggt | 480 |
| gccatcagca | aaaagccctg | ggtcaacgct | ctctttgcct | acggcatcga | cgtcattgga | 540 |
| tcgtccagat | ggatctggct | gcagtctcac | atcatgcgac | atcacaccta | caccaatcag | 600 |

| | |
|---|---|
| catggtctcg acctggatgc cgagtccgca gaaccattcc ttgtgttcca caactaccct | 660 |
| gctgccaaca ctgctcgaaa gtggtttcac cgattccagg cctggtacat gtacctcgtg | 720 |
| cttggagcct acggcgtttc gctggtgtac aaccctctct acatcttccg aatgcagcac | 780 |
| aacgacacca ttcccgagtc tgtcacagcc atgcgagaga acggctttct gcgacggtac | 840 |
| cgaacccttg cattcgttat gcgagctttc ttcatctttc gaaccgcctt cttgccctgg | 900 |
| tatctcactg gaacctccct gctcatcacc attcctctgg tgcccactgc taccggtgcc | 960 |
| ttcctcacct tcttttttcat cttgtctcac aacttcgatg gctcggagcg aatccccgac | 1020 |
| aagaactgca aggtcaagag ctccgagaag gacgttgaag ccgatcagat cgactggtac | 1080 |
| agagctcagg tggagacctc ttccacctac ggtggaccca ttgccatgtt ctttactggc | 1140 |
| ggtctcaact tccagatcga gcatcacctc tttcctcgaa tgtcgtcttg gcactatccc | 1200 |
| ttcgtgcagc aagctgtccg agagtgttgc gaacgacacg gagttcggta cgtcttctac | 1260 |
| cctaccattg tgggcaacat catttccacc ctcaagtaca tgcacaaagt cggtgtggtt | 1320 |
| cactgtgtca aggacgctca ggattcctaa | 1350 |

<210> SEQ ID NO 193
<211> LENGTH: 1365
<212> TYPE: DNA
<213> ORGANISM: Euglena anabaena

<400> SEQUENCE: 193

| | |
|---|---|
| atggccacca tctccctgac taccgagcag ctcctggaac accccgagct cgttgccatc | 60 |
| gacggagtcc tgtacgatct cttcggtctg gccaaggtgc attgcggagg caacctcatc | 120 |
| gaagctgccg gtgcatccga cggaaccgct ctgttctact ccatgcatcc tggagtcaag | 180 |
| ccagagaact cgaagcttct gcagcaattt gcccgaggca agcacgaacg aagctccaag | 240 |
| gatcccgtgt acaccttcga ctctcccttt gctcaggacg tcaagcagtc cgttcgagag | 300 |
| gtcatgaagg gtcgaaactg gtacgccact cctggcttct ggctgagaac cgcactcatc | 360 |
| atcgcttgta ctgccattgg cgagtggtac tggatcacaa ccggagcagt gatgtggggt | 420 |
| atctttactg gatacttcca ctcgcagatt ggcttggcca ttcaacacga tgcttctcac | 480 |
| ggagccatca gcaaaaagcc ctgggtcaac gccttttttcg cttatggcat cgacgccatt | 540 |
| ggttcctctc gttggatctg gctgcagtcc cacattatgc gacatcacac ttacaccaac | 600 |
| cagcatggcc tcgacctgga tgctgcctcg gcagagccgt tcatcttgtt ccactcctat | 660 |
| cctgctacca acgcctctcg aaagtggtac caccgatttc aggcgtggta catgtacatc | 720 |
| gttctgggaa tgtatggtgt ctcgatggtg tacaatccca tgtacctctt cacaatgcag | 780 |
| cacaacgaca ccattcccga ggccacttct ctcagaccag gcagcttttt caatcggcag | 840 |
| cgagcttttcg ccgtttccct cgactgctc ttcatcttcc gaaacgcctt tcttccctgg | 900 |
| tacattgctg gtgcctctcc tctgctcacc attcttctgg tgcccacggt cacaggcatc | 960 |
| ttcctcacct ttgtgttcgt tctgtcccat aacttcgagg gagccgaacg accccagag | 1020 |
| aagaactgca aggccaaacg agctaaggaa ggcaaggagg tcagagacgt ggaagaggat | 1080 |
| cgagtcgact ggtaccgagc acaggccgag actgctgcca cctacggtgg cagcgtggga | 1140 |
| atgatgctta caggcggtct caacctgcag atcgagcatc acttgtttcc ccgaatgtcc | 1200 |
| tcttggcact atcccttcat tcaagacacc gttcgggagt gttgcaagcg acatggcgtc | 1260 |
| cgttacacat actatcctac cattctcgag aacatcatgt ccactcttcg atacatgcag | 1320 |
| aaggtggggtg ttgctcacac cattcaggat gcccaggagt tctaa | 1365 |

<210> SEQ ID NO 194
<211> LENGTH: 1392
<212> TYPE: DNA
<213> ORGANISM: Peridinium sp. CCMP626

<400> SEQUENCE: 194

| | |
|---|---|
| atggctcccg acgccgacaa gctgcgacag cgaaaggctc agtccatcca ggacactgcc | 60 |
| gattctcagg ctaccgagct caagattggc accctgaagg gtctccaagg caccgagatc | 120 |
| gtcattgatg gcgacatcta cgacatcaaa gacttcgatc actgcggagg cgaatccatc | 180 |
| atgacctttg gtggcaacga cgttactgcc acctacaaga tgattcatcc ctaccactcg | 240 |
| aagcatcacc tggagaagat gaaaaaggtc ggtcgagtgc ccgactacac ctccgagtac | 300 |
| aagttcgata ctcccttcga acgagagatc aaacaggagg tcttcaagat tgtgcgaaga | 360 |
| ggtcgagagt ttggaacacc tggctacttc tttcgagcct tctgctacat cggtctcttc | 420 |
| ttttacctgc agtatctctg ggttaccact cctaccactt tcgcccttgc tatcttctac | 480 |
| ggtgtgtctc aggccttcat tggcctgaac gtccagcacg acgccaacca cggagctgcc | 540 |
| tccaaaaagc cctggatcaa caatttgctc ggcctgggtg ccgactttat cggaggctcc | 600 |
| aagtggctct ggatgaacca gcactggacc catcacactt acaccaacca tcacgagaag | 660 |
| gatcccgacg ccctgggtgc agagcctatg ctgctcttca acgactatcc cttgggtcac | 720 |
| cccaagcgaa ccctcattca tcacttccaa gccttctact atctgtttgt ccttgctggc | 780 |
| tactgggtgt cttcggtgtt caaccctcag atcctggacc tccagcaccg aggtgcccag | 840 |
| gctgtcggca tgaagatgga gaacgactac attgccaagt ctcgaaagta cgctatcttc | 900 |
| ctgcgactcc tgtacatcta caccaacatt gtggctccca tccagaacca aggcttttcg | 960 |
| ctcaccgtcg ttgctcacat tcttactatg ggtgtcgcct ccagcctgac cctcgctact | 1020 |
| ctgttcgccc tctcccacaa cttcgagaac gcagatcggg atcccaccta cgaggctcga | 1080 |
| aagggaggcg agcctgtctg ttggttcaag tcgcaggtgg aaacctcctc tacttacggt | 1140 |
| ggcttcattt ccggttgcct tacaggcgga ctcaactttc aggtcgagca tcacctgttt | 1200 |
| cctcgaatgt cctctgcctg gtaccctac atcgctccta ccgttcgaga ggtctgcaaa | 1260 |
| aagcacggcg tcaagtacgc ctactatccc tgggtgtggc agaacctcat ctcgaccgtc | 1320 |
| aagtacctgc atcagtccgg aactggctcg aactggaaga acggtgccaa tccctactct | 1380 |
| ggcaagctgt aa | 1392 |

<210> SEQ ID NO 195
<211> LENGTH: 1392
<212> TYPE: DNA
<213> ORGANISM: Peridinium sp. CCMP626

<400> SEQUENCE: 195

| | |
|---|---|
| atggctcccg acgccgacaa gctgcgacag cgaaaggctc agtccatcca ggacactgcc | 60 |
| gattctcagg ctaccgagct caagattggc accctgaagg gtctccaagg caccgagatc | 120 |
| gtcattgatg gcgacatcta cgacatcaaa gacttcgatc actggggagg cgaatccatc | 180 |
| atgacctttg gtggcaacga cgttactgcc acctacaaga tgattcatcc ctaccactcg | 240 |
| aagcatcacc tggagaagat gaaaaaggtc ggtcgagtgc ccgactacac ctccgagtac | 300 |
| aagttcgata ctcccttcga acgagagatc aaacaggagg tcttcaagat tgtgcgaaga | 360 |
| ggtcgagagt ttggaacacc tggctacttc tttcgagcct tctgctacat cggtctcttc | 420 |
| ttttacctgc agtatctctg ggttaccact cctaccactt tcgcccttgc tatcttctac | 480 |

```
ggtgtgtctc aggccttcat tggcctgaac gtccagcacg acgccaacca cggagctgcc    540
tccaaaaagc cctggatcaa caatttgctc ggcctgggtg ccgactttat cggaggctcc    600
aagtggctct ggatgaacca gcactggacc catcacactt acaccaacca tcacgagaag    660
gatcccgacg ccctgggtgc agagcctatg ctgctcttca acgactatcc cttgggtcac    720
cccaagcgaa ccctcattca tcacttccaa gccttctact atctgtttgt ccttgctggc    780
tactgggtgt cttcggtgtt caaccctcag atcctggacc tccagcaccg aggtgcccag    840
gctgtcggca tgaagatgga gaacgactac attgccaagt ctcgaaagta cgctatcttc    900
ctgcgactcc tgtacatcta caccaacatt gtggctccca tccagaacca aggcttttcg    960
ctcaccgtcg ttgctcacat tcttactatg ggtgtcgcct ccagcctgac cctcgctact   1020
ctgttcgccc tctcccacaa cttcgagaac gcagatcggg atcccaccta cgaggctcga   1080 aaggaggcg agcctgtctg ttggttcaag tcgcaggtgg aaacctcctc tacttacggt   1140
ggcttcattt ccggttgcct tacaggcgga ctcaactttc aggtcgagca tcacctgttt   1200
cctcgaatgt cctctgcctg gtaccctac atcgctccta ccgttcgaga ggtctgcaaa   1260
aagcacggcg tcaagtacgc ctactatccc tgggtgtggc agaacctcat ctcgaccgtc   1320
aagtacctgc atcagtccgg aactggctcg aactggaaga acggtgccaa tccctactct   1380
ggcaagctgt aa                                                       1392
```

MUTANT Δ5 DESATURASES MUTATED IN THE HEME-BINDING MOTIF (HPGG) AND THEIR USE IN MAKING POLYUNSATURATED FATTY ACIDS

This application claims the benefit of U.S. Provisional Application No. 61/098,333, filed Sep. 19, 2008, the disclosure of which is hereby incorporated by reference in its entirety.

FIELD OF THE INVENTION

This invention is in the field of biotechnology. More specifically, this invention pertains to the creation of nucleic acid fragments encoding mutant Δ5 fatty acid desaturase enzymes (wherein at least one mutation occurs within the HPGG motif of the cytochrome $b_5$-like domain) and the use of these desaturases in making long-chain polyunsaturated fatty acids ["PUFAs"].

BACKGROUND OF THE INVENTION

A variety of different hosts including plants, algae, fungi, stramenopiles and yeast are being investigated as means for commercial polyunsaturated fatty acid ["PUFA"] production. Genetic engineering has demonstrated that the natural abilities of some hosts (even those natively limited to linoleic acid [LA; 18:2 ω-6] and α-linolenic acid [ALA; 18:3 ω-3] fatty acid production) can be substantially altered to result in high-level production of various long-chain ω-3/ω-6 PUFAs. Whether this is the result of natural abilities or recombinant technology, production of arachidonic acid [ARA; 20:4 ω-6], eicosapentaenoic acid [EPA; 20:5 ω-3] and docosahexaenoic acid [DHA; 22:6 ω-3] may all require expression of a Δ5 desaturase.

Most Δ5 desaturase enzymes identified thus far have the primary ability to convert dihomo-γ-linolenic acid [DGLA; 20:3 ω-6] to ARA, with secondary activity in converting eicosatetraenoic acid [ETA; 20:4 ω-3] to EPA. Numerous Δ5 desaturases have been disclosed in both the open literature and the patent literature. General characteristics of Δ5 desaturases, based on desaturase evolution, are well-described by P. Sperling et al. (*Prostaglandins Leukot. Essent. Fatty Acids*, 68:73-95 (2003). Along with Δ6, Δ8 and Δ4 desaturases, Δ5 desaturases are known as long-chain PUFA "front-end" desaturases (wherein desaturation occurs between a pre-existing double bond and the carboxyl terminus of the fatty acid's acyl group, as opposed to methyl-directed desaturation). These desaturases are characterized by three histidine boxes [H(X)$_{3-4}$H (SEQ ID NOs:1 and 2), H(X)$_{2-3}$HH (SEQ ID NOs:3 and 4) and H/Q(X)$_{2-3}$HH (SEQ ID NOs:5 and 6)] and are members of the cytochrome $b_5$ fusion superfamily, since they possess a fused cytochrome $b_5$ domain at their N-terminus which serves as an electron donor. The cytochrome $b_5$ domain also contains a conserved heme-binding motif (i.e., a histidine-proline-glycine-glycine sequence or "HPGG" [SEQ ID NO:180] sequence), despite divergence of the remaining cytochrome $b_5$ domain sequences. These motif sequences are the subject of U.S. Pat. No. 5,972,664.

A number of studies have suggested that the HPGG motif is implicated in enzyme activity. Sayanova, O. et al. (*Plant Physiol.*, 121:641 (1999)) performed site-directed mutagenesis to replace the histidine residue of the HPGG motif with an alanine residue in the Δ6 desaturase of borage. The mutant enzyme was expressed in *Arabidopsis*; however, no enzymatic activity could be measured, suggesting that the cytochrome $b_5$ domain of the desaturase was important for function. A similar study was performed in a rat Δ6 desaturase, where an alanine for histidine substitution was engineered within the HPGG motif. The mutated protein also had no activity (Guillou, H., et al., *J. Lipid Res.*, 45:32-40 (2004)). Most recently, Hongsthong, A. et al. (*Appl. Microbiol. Biotechnol.*, 72:1192-1201 (2006)) reported substitution of the histidine residue of the HPGG motif with an alanine residue in the Δ6 desaturase of *Spirulina*. As with previous reports, the mutation rendered the mutant enzyme unable to produce GLA in *E. coli*, suggesting that the cytochrome $b_5$ domain was important for activity and that alterations in this motif will result in diminished enzyme activity. Although Δ5 desaturase enzymes are relatively common and well characterized, there remains a need for enzymes that are efficiently expressed at high levels in production host cells capable of making PUFAs.

The problem to be solved therefore is to discover new Δ5 desaturase enzymes having high activity that are well suited for integration into PUFA biosynthetic pathways in commercially useful host cells. Applicants have solved the stated problem through the unexpected discovery that alterations in the HPGG motif of the cytochrome $b_5$ domain of various Δ5 desaturases resulted in up to 38% improvement in enzymatic activity, based on the conversion of DGLA to ARA.

SUMMARY OF THE INVENTION

The present invention relates to new genetic constructs encoding polypeptides having Δ5 desaturase activity, and their use in bacteria, yeast, algae, euglenoids, stramenopiles, oomycetes and fungi for the production of PUFAs.

Accordingly provided herein is a mutant polypeptide having Δ5 desaturase activity comprising an amino acid motif selected from the group consisting of: SEQ ID NO:183 (His-Gly-Gly-Gly or HGGG), SEQ ID NO:184 (His-His-Gly-Gly or HHGG), SEQ ID NO:186 (His-Cys-Gly-Gly or HCGG), SEQ ID NO:187 (His-Trp-Gly-Gly or HWGG) and SEQ ID NO:185 (His-Pro-Gly-Ser or HPGS). Preferred mutant Δ5 desaturase polypeptides are those that demonstrate a dihomo-γ-linolenic acid to arachidonic acid conversion efficiency that is greater than the dihomo-γ-linolenic acid to arachidonic acid conversion efficiency of the parent polypeptide from which the mutant was derived.

In a second embodiment provided herein is an isolated nucleic acid molecule substantially encoding the polypeptide of the invention.

In a third embodiment provided herein is a microbial host cell expressing the polypeptide of the invention.

In a fourth embodiment provided herein is a method for the production of arachidonic acid comprising growing a microbial host cell expressing the polypeptide of claim 1 in the presence of dihomo-γ-linolenic acid, wherein the dihomo-γ-linolenic acid is converted to arachidonic acid.

In a fifth embodiment provided herein is a method of the production of eicosapentaenoic acid comprising growing a microbial host cell expressing the polypeptide of claim 1 in the presence of eicosatetraenoic acid, wherein the eicosatetraenoic acid is converted to eicosapentaenoic acid.

BRIEF DESCRIPTION OF THE DRAWINGS AND SEQUENCE LISTINGS

Figure 1B:
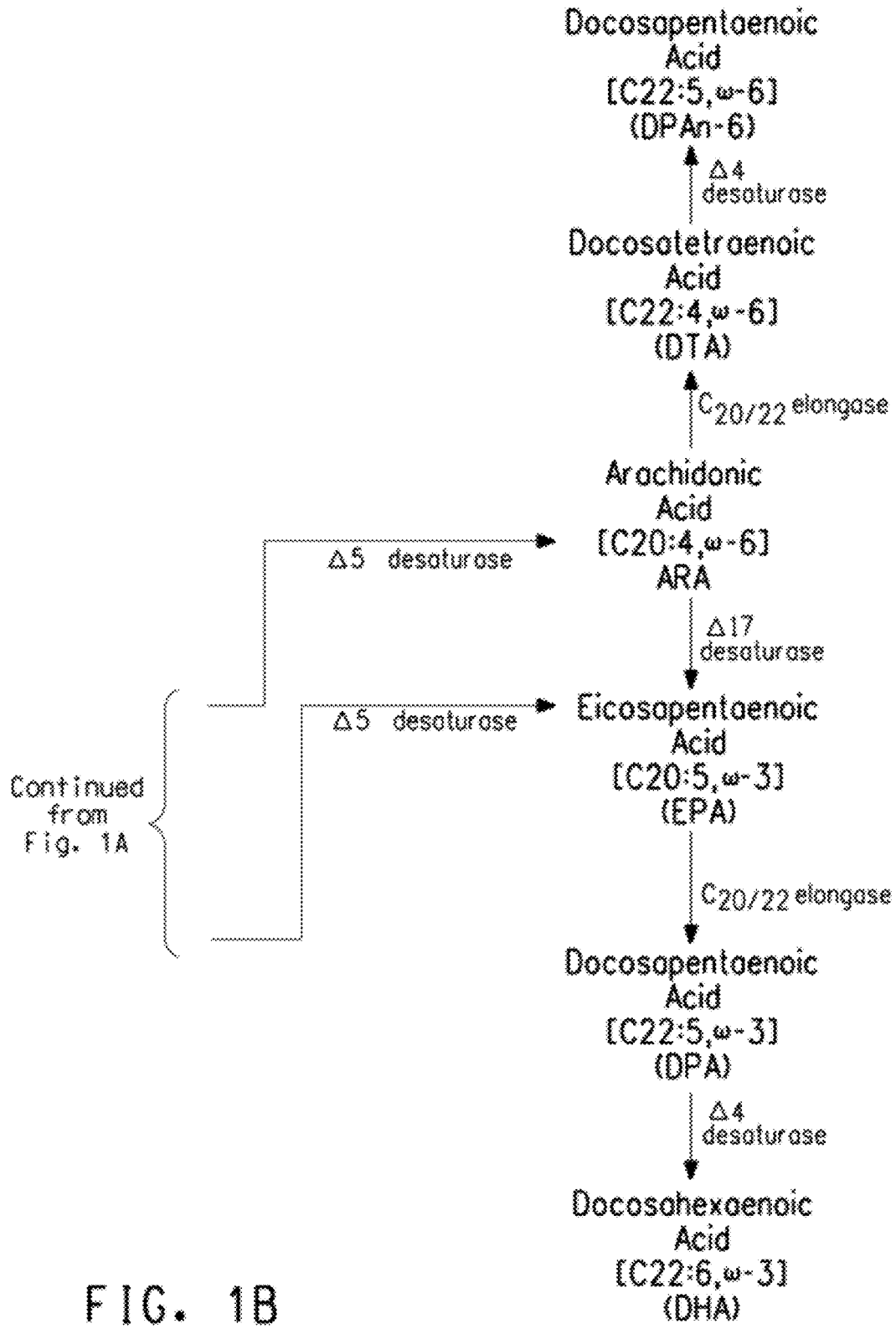

FIG. 1A and FIG. 1B illustrate the ω-3/ω-6 fatty acid biosynthetic pathway, and should be viewed together when considering the description of this pathway below.

FIG. 2 provides plasmid maps for the following: (A) pDMW369; and, (B) pZUF17.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:7-19, 58, 97-100, 139, 140 and 179-195 are ORFs encoding genes or proteins (or portions thereof), or plasmids, as identified in Table 1.

SEQ ID NOs:59-96 correspond to oligonucleotide primers utilized to individually mutate the second glycine residue of the HPGG motif of EgD5S by site-directed mutagenesis.

SEQ ID NOs:101-138 correspond to oligonucleotide primers utilized to individually mutate the proline residue of the HPGG motif of EaD5S by site-directed mutagenesis.

SEQ ID NOs:141-178 correspond to oligonucleotide primers utilized to individually mutate the proline residue of the HPGG motif of RD5S by site-directed mutagenesis.

DETAILED DESCRIPTION OF THE INVENTION

New mutant Δ5 desaturase enzymes and genes encoding the same that may be used for the manipulation of biochemical pathways for the production of healthful PUFAs are disclosed herein. These mutant Δ5 desaturases possess at least one mutation within the HPGG motif (SEQ ID NO:180) of the cytochrome $b_5$ domain.

TABLE 1

Summary Of Nucleic Acid And Protein SEQ ID Numbers

| Description | Nucleic acid SEQ ID NO. | Protein SEQ ID NO. |
|---|---|---|
| His-rich motif: H(X)₃H | — | 1 |
| His-rich motif: H(X)₄H | — | 2 |
| His-rich motif: H(X)₂HH | — | 3 |
| His-rich motif: H(X)₃HH | — | 4 |
| His-rich motif: (H/Q)(X)₂HH | — | 5 |
| His-rich motif: (H/Q)(X)₃HH | — | 6 |
| *Euglena gracilis* Δ5 desaturase ("EgD5") | 7 (1350 bp) | 8 (449 AA) |
| Synthetic Δ5 desaturase, derived from *Euglena gracilis*, codon-optimized for expression in *Yarrowia lipolytica* ("EgD5S") | 9 (1350 bp) | 10 (449 AA) |
| *Euglena anabaena* Δ5 desaturase ("EaD5") | 11 (1362 bp) | 12 (454 AA) |
| Synthetic Δ5 desaturase, derived from *Euglena anabaena*, codon-optimized for expression in *Yarrowia lipolytica* ("EaD5S") | 13 (1362 bp) | 14 (454 AA) |
| *Peridinium* sp. CCMP626 Δ5 desaturase ("RD5") | 15 (1392 bp) | 16 (463 AA) |
| Synthetic Δ5 desaturase, derived from *Peridinium* sp. CCMP626, codon-optimized for expression in *Yarrowia lipolytica* ("RD5S") | 17 (1392 bp) | 18 (463 AA) |
| Plasmid pDMW369 | 19 (8438 bp) | — |
| mutant Δ5 desaturase EgD5S-HXGG (i.e., comprising either a HGGG or a HHGG motif) | — | 58 (449 AA) |
| mutant Δ5 desaturase EgD5S-HPGS (i.e., comprising a HPGS motif) | — | 97 (449 AA) |
| Plasmid pZUFmEaD5S | 98 (8357 bp) | — |
| Plasmid pZUF17 | 99 (8165 bp) | — |
| Plasmid pEaD5S | 100 (3983 bp) | — |
| mutant Δ5 desaturase EaD5S-HCGG (i.e., comprising a HCGG motif) | — | 139 (454 AA) |
| Plasmid pZURD5S | 140 (8480 bp) | — |
| mutant Δ5 desaturase RD5S-HXGG (i.e., comprising either a HCGG or a HWGG motif) | — | 179 (463 AA) |
| HPGG motif | — | 180 |
| HXGG motif | — | 181 |
| HPGX motif | — | 182 |
| HGGG motif | — | 183 |
| HHGG motif | — | 184 |
| HPGS motif | — | 185 |
| HCGG motif | — | 186 |
| HWGG motif | — | 187 |
| HAGG motif | — | 188 |
| HPGA motif | — | 189 |
| mutant Δ5 desaturase EgD5S-HGGG | 190 (1350 bp) | — |
| mutant Δ5 desaturase EgD5S-HHGG | 191 (1350 bp) | — |
| mutant Δ5 desaturase EgD5S-HPGS | 192 (1350 bp) | — |
| mutant Δ5 desaturase EaD5S-HCGG | 193 (1365 bp) | — |
| mutant Δ5 desaturase RD5S-HCGG | 194 (1392 bp) | — |
| mutant Δ5 desaturase RD5S-HWGG | 194 (1392 bp) | — |

SEQ ID NOs:20-57 correspond to oligonucleotide primers utilized to individually mutate the proline residue of the HPGG motif of EgD5S by site-directed mutagenesis.

PUFAs, or derivatives thereof, are used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use, either human or veterinary.

All patent and non-patent literature cited herein is hereby incorporated by reference.

In this disclosure, a number of terms and abbreviations are used. The following definitions are provided.

"Open reading frame" is abbreviated "ORF".

"Polymerase chain reaction" is abbreviated "PCR".

"American Type Culture Collection" is abbreviated "ATCC".

"Polyunsaturated fatty acid(s)" is abbreviated "PUFA(s)".

"Triacylglycerols" are abbreviated "TAGs".

"Total fatty acids" are abbreviated as "TFAs".

The term "invention" or "present invention" as used herein is not meant to be limiting to any one specific embodiment of the invention but applies generally to any and all embodiments of the invention as described in the claims and specification.

The term "fatty acids" refers to long chain aliphatic acids (alkanoic acids) of varying chain lengths, from about $C_{12}$ to $C_{22}$, although both longer and shorter chain-length acids are known. The predominant chain lengths are between $C_{16}$ and $C_{22}$. The structure of a fatty acid is represented by a simple notation system of "X:Y", where X is the total number of carbon ["C"] atoms in the particular fatty acid and Y is the number of double bonds. Additional details concerning the differentiation between "saturated fatty acids" versus "unsaturated fatty acids", "monounsaturated fatty acids" versus "polyunsaturated fatty acids" ["PUFAs"], and "omega-6 fatty acids" ["ω-6" or "n-6"] versus "omega-3 fatty acids" ["ω-3" or ["n-3"] are provided in U.S. Pat. No. 7,238,482, which is hereby incorporated herein by reference.

Nomenclature used to describe PUFAs herein is shown below in Table 2. In the column titled "Shorthand Notation", the omega-reference system is used to indicate the number of carbons, the number of double bonds and the position of the double bond closest to the omega carbon, counting from the omega carbon (which is numbered 1 for this purpose). The remainder of the Table summarizes the common names of ω-3 and ω-6 fatty acids and their precursors, the abbreviations that will be used throughout the specification and the chemical name of each compound.

TABLE 2

Nomenclature Of Polyunsaturated Fatty Acids And Precursors

| Common Name | Abbreviation | Chemical Name | Shorthand Notation |
|---|---|---|---|
| Myristic | — | tetradecanoic | 14:0 |
| Palmitic | Palmitate | hexadecanoic | 16:0 |
| Palmitoleic | — | 9-hexadecenoic | 16:1 |
| Stearic | — | octadecanoic | 18:0 |
| Oleic | — | cis-9-octadecenoic | 18:1 |
| Linoleic | LA | cis-9,12-octadecadienoic | 18:2 ω-6 |

TABLE 2-continued

Nomenclature Of Polyunsaturated Fatty Acids And Precursors

| Common Name | Abbreviation | Chemical Name | Shorthand Notation |
|---|---|---|---|
| γ-Linolenic | GLA | cis-6,9,12-octadecatrienoic | 18:3 ω-6 |
| Eicosadienoic | EDA | cis-11,14-eicosadienoic | 20:2 ω-6 |
| Dihomo-γ-Linolenic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |
| Eicosatrienoic | ETrA | cis-11,14,17-eicosatrienoic | 20:3 ω-3 |
| Sciadonic | SCI | cis-5,11,14-eicosatrienoic | 20:3b ω-6 |
| Juniperonic | JUP | cis-5,11,14,17-eicosatetraenoic | 20:4b ω-3 |
| Eicosatetraenoic | ETA | cis-8,11,14,17-eicosatetraenoic | 20:4 ω-3 |
| Eicosapentaenoic | EPA | cis-5,8,11,14,17-eicosapentaenoic | 20:5 ω-3 |
| Docosatetraenoic | DTA | cis-7,10,13,16-docosatetraenoic | 22:4 ω-6 |
| Docosapentaenoic | DPAn-6 | cis-4,7,10,13,16-docosapentaenoic | 22:5 ω-6 |
| Docosapentaenoic | DPA | cis-7,10,13,16,19-docosapentaenoic | 22:5 ω-3 |
| Docosahexaenoic | DHA | cis-4,7,10,13,16,19-docosahexaenoic | 22:6 ω-3 |

Although the ω-3/ω-6 PUFAs listed in Table 2 are the most likely to be accumulated in the oil fractions of microbial hosts using the methods described herein, this list should not be construed as limiting or as complete.

The term "oil" refers to a lipid substance that is liquid at 25° C. and usually polyunsaturated. In oleaginous organisms, oil constitutes a major part of the total lipid. "Oil" is composed primarily of triacylglycerols ["TAGs"] but may also contain other neutral lipids, phospholipids and free fatty acids. The fatty acid composition in the oil and the fatty acid composition of the total lipid are generally similar; thus, an increase or decrease in the concentration of PUFAs in the total lipid will correspond with an increase or decrease in the concentration of PUFAs in the oil, and vice versa.

"Neutral lipids" refer to those lipids commonly found in cells in lipid bodies as storage fats and are so called because at cellular pH, the lipids bear no charged groups. Generally, they are completely non-polar with no affinity for water. Neutral lipids generally refer to mono-, di-, and/or triesters of glycerol with fatty acids, also called monoacylglycerol, diacylglycerol or triacylglycerol, respectively, or collectively, acylglycerols. A hydrolysis reaction must occur to release free fatty acids from acylglycerols.

The term "triacylglycerols" ["TAGs"] refers to neutral lipids composed of three fatty acyl residues esterified to a glycerol molecule. TAGs can contain long chain PUFAs and saturated fatty acids, as well as shorter chain saturated and unsaturated fatty acids.

The term "total fatty acids" ["TFAs"] herein refer to the sum of all cellular fatty acids that can be derivatized to fatty acid methyl esters ["FAMEs"] by the base transesterification method (as known in the art) in a given sample, which may be the biomass or oil, for example. Thus, total fatty acids include fatty acids from neutral lipid fractions (including diacylglycerols, monoacylglycerols and TAGs) and from polar lipid fractions (including the phosphatidylcholine and phosphatidylethanolamine fractions) but not free fatty acids.

The term "total lipid content" of cells is a measure of TFAs as a percent of the dry cell weight ["DCW"], although total lipid content can be approximated as a measure of FAMEs as a percent of the DCW ["FAMEs % DCW"]. Thus, total lipid content ["TFAs % DCW"] is equivalent to, e.g., milligrams of total fatty acids per 100 milligrams of DCW.

The concentration of a fatty acid in the total lipid is expressed herein as a weight percent of TFAs ["% TFAs"], e.g., milligrams of the given fatty acid per 100 milligrams of TFAs. Unless otherwise specifically stated in the disclosure herein, reference to the percent of a given fatty acid with respect to total lipids is equivalent to concentration of the fatty acid as % TFAs, e.g., % EPA of total lipids is equivalent to EPA % TFAs.

The terms "lipid profile" and "lipid composition" are interchangeable and refer to the amount of individual fatty acids contained in a particular lipid fraction, such as in the total lipid or the oil, wherein the amount is expressed as a weight percent of TFAs. The sum of each individual fatty acid present in the mixture should be 100.

The term "PUFA biosynthetic pathway" refers to a metabolic process that converts oleic acid to ω-6 fatty acids such as LA, EDA, GLA, DGLA, ARA, DTA and DPAn-6 and ω-3 fatty acids such as ALA, STA, ETrA, ETA, EPA, DPA and DHA. This process is well described in the literature. See e.g., U.S. Pat. Appl. Pub. No. 2006-0115881-A1. Briefly, this process involves elongation of the carbon chain through the addition of carbon atoms and desaturation of the molecule through the addition of double bonds, via a series of special elongation and desaturation enzymes termed "PUFA biosynthetic pathway enzymes" that are present in the endoplasmic reticulum membrane. More specifically, "PUFA biosynthetic pathway enzymes" refer to any of the following enzymes (and genes which encode said enzymes) associated with the biosynthesis of a PUFA, including: Δ4 desaturase, Δ5 desaturase, Δ6 desaturase, Δ12 desaturase, Δ15 desaturase, Δ17 desaturase, Δ9 desaturase, Δ8 desaturase, Δ9 elongase, $C_{14/16}$ elongase, $C_{16/18}$ elongase, $C_{18/20}$ elongase and/or $C_{20/22}$ elongase.

The term "desaturase" refers to a polypeptide that can desaturate, i.e., introduce a double bond, in one or more fatty acids to produce a fatty acid or precursor of interest. Despite use of the omega-reference system throughout the specification to refer to specific fatty acids, it is more convenient to indicate the activity of a desaturase by counting from the carboxyl end of the substrate using the delta-system. Of particular interest herein are Δ5 desaturases that desaturate a fatty acid between the fifth and sixth carbon atom numbered from the carboxyl-terminal end of the molecule and that can, for example, catalyze the conversion of DGLA to ARA and/or ETA to EPA. Other fatty acid desaturases include, for example: Δ8 desaturases, Δ6 desaturases, Δ4 desaturases, Δ12 desaturases, Δ15 desaturases, Δ17 desaturases and Δ9 desaturases. In the art, Δ15 and Δ17 desaturases are also occasionally referred to as "omega-3 desaturases", "w-3 desaturases" and/or "ω-3 desaturases", based on their ability to convert ω-6 fatty acids into their ω-3 counterparts (e.g., conversion of LA into ALA and ARA into EPA, respectively). It may be desirable to empirically determine the specificity of a particular fatty acid desaturase by transforming a suitable host with the gene for the fatty acid desaturase and determining its effect on the fatty acid profile of the host.

The term "EgD5" refers to a Δ5 desaturase enzyme (SEQ ID NO:8) isolated from *Euglena gracilis*, encoded by SEQ ID NO:7 herein. Similarly, the term "EgD5S" refers to a synthetic Δ5 desaturase derived from *E. gracilis* that is codon-optimized for expression in *Yarrowia lipolytica* (i.e., SEQ ID NOs:9 and 10). Further details concerning EgD5 and EgD5S are described in Intl. App. Pub. No. WO 2007/136671.

The term "EaD5" refers to a Δ5 desaturase enzyme (SEQ ID NO:12) isolated from *Euglena anabaena*, encoded by SEQ ID NO:11 herein. Similarly, the term "EaD5S" refers to a synthetic Δ5 desaturase derived from *E. anabaena* that is codon-optimized for expression in *Yarrowia lipolytica* (i.e., SEQ ID NOs:13 and 14). Further details concerning EaD5 and EaD5S are described in U.S. Pat. Appl. Pub. No. 2008-0274521-A1.

The term "RD5" refers to a Δ5 desaturase enzyme (SEQ ID NO:16) isolated from *Peridinium* sp. CCMP626, encoded by SEQ ID NO:15 herein. Similarly, the term "RD5S" refers to a synthetic Δ5 desaturase derived from *Peridinium* sp. CCMP626 that is codon-optimized for expression in *Yarrowia lipolytica* (i.e., SEQ ID NOs:17 and 18). Further details concerning RD5 and RD5S are described in Intl. App. Pub. No. WO 2007/136646.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Motifs that are universally found in Δ5 desaturase enzymes of animal, plants and fungi include three histidine boxes (i.e., $H(X)_{3-4}H$ [SEQ ID NOs:1 and 2], $H(X)_{2-3}HH$ [SEQ ID NOs:3 and 4] and $H/Q(X)_{2-3}HH$ [SEQ ID NOs:5 and 6]) and a heme-binding motif (i.e., His-Pro-Gly-Gly or HPGG [SEQ ID NO:180]) within the fused cytochrome $b_5$ domain at the N-terminus.

The term "mutant Δ5 desaturase" refers to a Δ5 desaturase as described herein that has at least one mutation within the HPGG motif (SEQ ID NO:180) of the cytochrome $b_5$ domain, wherein said mutation results in an amino acid substitution, either conservative or non-conservative. Although the mutation(s) may include any amino acid substitution, the mutant Δ5 desaturase preferably comprises a mutant motif selected from the group consisting of His-Xaa-Gly-Gly or "HXGG" (SEQ ID NO:181) and His-Pro-Gly-Xaa or "HPGX" (SEQ ID NO:182) and the Δ5 desaturase activity of the mutant Δ5 desaturase is at least about functionally equivalent to the Δ5 desaturase activity of the wildtype Δ5 desaturase. More preferred, the mutant motif is selected from the group consisting of: SEQ ID NO:183 (His-Gly-Gly-Gly or "HGGG"), SEQ ID NO:184 (His-His-Gly-Gly or "HHGG"), SEQ ID NO:186 (His-Cys-Gly-Gly or "HCGG"), SEQ ID NO:187 (His-Trp-Gly-Gly or "HWGG") and SEQ ID NO:185 (His-Pro-Gly-Ser or "HPGS"). See, e.g., the Δ5 desaturases set forth as SEQ ID NO:58, SEQ ID NO:97, SEQ ID NO:139 and SEQ ID NO:179.

Each "mutant Δ5 desaturase" has a "corresponding wildtype Δ5 desaturase". Specifically, the mutant Δ5 desaturase and corresponding wildtype Δ5 desaturase share identical amino acid sequences, with the exception that the wildtype will comprise a HPGG motif (SEQ ID NO:180) within the cytochrome $b_5$ domain, while the mutant will comprise at least one mutation within this motif (as described above).

A mutant Δ5 desaturase is "at least about functionally equivalent" to the corresponding wildtype Δ5 desaturase when enzymatic activity and specific selectivity of the mutant Δ5 sequence are comparable to that of the corresponding wildtype Δ5 desaturase. Thus, a functionally equivalent mutant Δ5 desaturase will possess Δ5 desaturase activity that is not substantially reduced with respect to that of the corresponding wildtype Δ5 desaturase when the "conversion efficiency" of each enzyme is compared (i.e., a mutant Δ5 desaturase will have at least about 50-75%, preferably at least about 75-85%, more preferably at least about 85-95%, and most preferably at least about 95% of the enzymatic activity of the wildtype Δ5 desaturase). The Δ5 desaturase activity of the two polypeptides may be substantially identical. Preferably, the mutant Δ5 desaturase will have increased enzymatic activity and specific selectivity when compared to that of the corresponding wildtype Δ5 desaturase, i.e., having at least about 101-105%, more preferably at least about 106-115% and most preferably at least about 116-125% of the enzymatic activity of the wildtype Δ5 desaturase.

The terms "conversion efficiency" and "percent substrate conversion" refer to the efficiency by which a particular enzyme (e.g., a desaturase) can convert substrate to product. The conversion efficiency is measured according to the following formula: ([product]/[substrate+product])*100. Thus, "DGLA to ARA conversion efficiency" refers to the conversion efficiency by which the substrate, DGLA, is converted to the product, ARA.

The term "elongase" refers to a polypeptide that can elongate a fatty acid carbon chain to produce an acid 2 carbons longer than the fatty acid substrate that the elongase acts upon. This process of elongation occurs in a multi-step mechanism in association with fatty acid synthase, as described in U.S. Pat. App. Pub. No. 2005/0132442. Examples of reactions catalyzed by elongase systems are the conversion of GLA to DGLA, STA to ETA and EPA to DPA.

In general, the substrate selectivity of elongases is somewhat broad but segregated by both chain length and the degree and type of unsaturation. For example, a $C_{14/16}$ elongase will utilize a $C_{14}$ substrate (e.g., myristic acid), a $C_{16/18}$ elongase will utilize a $C_{16}$ substrate (e.g., palmitate), a $C_{18/20}$ elongase will utilize a $C_{18}$ substrate (e.g., GLA, STA, LA, ALA) and a $C_{20/22}$ elongase [also referred to as a Δ5 elongase] will utilize a $C_{20}$ substrate (e.g., ARA, EPA). For the purposes herein, two distinct types of $C_{18/20}$ elongases can be defined: a Δ6 elongase will catalyze conversion of GLA and STA to DGLA and ETA, respectively, while a Δ9 elongase is able to catalyze the conversion of LA and ALA to EDA and ETrA, respectively.

It is important to note that some elongases have broad specificity and thus a single enzyme may be capable of catalyzing several elongase reactions e.g., thereby acting as both a $C_{16/18}$ elongase and a $C_{18/20}$ elongase. It may be desirable to empirically determine the specificity of a fatty acid elongase by transforming a suitable host with the gene for the fatty acid elongase and determining its effect on the fatty acid profile of the host.

The term "oleaginous" refers to those organisms that tend to store their energy source in the form of oil (Weete, In: Fungal Lipid Biochemistry, $2^{nd}$ Ed., Plenum, 1980). Generally, the cellular oil content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.*, 57:419-25 (1991)). It is common for oleaginous microorganisms to accumulate in excess of about 25% of their dry cell weight as oil.

The term "oleaginous yeast" refers to those microorganisms classified as yeasts that can make oil. Examples of oleaginous yeast include, but are no means limited to, the following genera: *Yarrowia, Candida, Rhodotorula, Rhodosporidium, Cryptococcus, Trichosporon* and *Lipomyces*. Alternatively, organisms classified as yeasts that are engineered to make more than 25% of their dry cell weight as oil are also "oleaginous".

The term "amino acid" will refer to the basic chemical structural unit of a protein or polypeptide. The amino acids are identified by either the one-letter code or the three-letter codes for amino acids, in conformity with the IUPAC-IYUB standards described in *Nucleic Acids Research*, 13:3021-3030 (1985) and in the *Biochemical Journal*, 219 (2):345-373 (1984).

The term "conservative amino acid substitution" refers to a substitution of an amino acid residue in a given protein with another amino acid, without altering the chemical or functional nature of that protein. For example, it is well known in the art that alterations in a gene that result in the production of a chemically equivalent amino acid at a given site (but do not affect the structural and functional properties of the encoded, folded protein) are common. For the purposes herein, "conservative amino acid substitutions" are defined as exchanges within one of the following five groups:

1. Small aliphatic, nonpolar or slightly polar residues: Ala [A], Ser [S], Thr [T] (Pro [P], Gly [G]);
2. Polar, negatively charged residues and their amides: Asp [D], Asn [N], Glu [E], Gln [Q];
3. Polar, positively charged residues: His [H], Arg [R], Lys [K];
4. Large aliphatic, nonpolar residues: Met [M], Leu [L], Ile [I], Val [V] (Cys [C]); and
5. Large aromatic residues: Phe [F], Tyr [Y], Trp [W].

Thus, Ala, a slightly hydrophobic amino acid, may be substituted by another less hydrophobic residue (e.g., Gly). Similarly, changes which result in substitution of one negatively charged residue for another (e.g., Asp for Glu) or one positively charged residue for another (e.g., Lys for Arg) can also be expected to produce a functionally equivalent product. As such, conservative amino acid substitutions generally maintain: the structure of the polypeptide backbone in the area of the substitution; the charge or hydrophobicity of the molecule at the target site; or, the bulk of the side chain. Additionally, in many cases, alterations of the N-terminal and C-terminal portions of the protein molecule would also not be expected to alter the activity of the protein.

The term "non-conservative amino acid substitution" refers to an amino acid substitution that is generally expected to produce the greatest change in protein properties. Thus, for example, a non-conservative amino acid substitution would be one whereby: 1) a hydrophilic residue is substituted for/by a hydrophobic residue (e.g., Ser or Thr for/by Leu, Ile, Val); 2) a Cys or Pro is substituted for/by any other residue; 3) a residue having an electropositive side chain is substituted for/by an electronegative residue (e.g., Lys, Arg or H is for/by Asp or Glu); or, 4) a residue having a bulky side chain is substituted for/by one not having a side chain (e.g., Phe for/by Gly). Sometimes, non-conservative amino acid substitutions between two of the five groups will not affect the activity of the encoded protein.

The terms "polynucleotide", "polynucleotide sequence", "nucleic acid sequence", "nucleic acid fragment" and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T., *Molecular Cloning: A Laboratory Manual, 2$^{nd}$* ed., Cold Spring Harbor Laboratory: Cold Spring Harbor, N.Y. (1989), which is hereby incorporated herein by reference, particularly Chapter 11 and Table 11.1. The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of thermal melting point ["$T_m$"] for hybrids of nucleic acids having those sequences. The relative stability, corresponding to higher $T_m$, of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as Basic Local Alignment Search Tool ["BLAST"] (Altschul, S. F., et al., *J. Mol. Biol.*, 215: 403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The disclosure herein teaches the complete amino acid and nucleotide sequence encoding particular microbial proteins. The skilled artisan, having the benefit of the sequences as reported herein, may now use all or a substantial portion of the disclosed sequences for purposes known to those skilled in this art. Accordingly, the complete sequences as reported in the accompanying Sequence Listing, as well as substantial portions of those sequences as defined above, are encompassed in the present disclosure.

The term "complementary" is used to describe the relationship between nucleotide bases that are capable of hybridizing to one another. For example, with respect to DNA, adenosine is complementary to thymine and cytosine is complementary to guanine. Accordingly, isolated nucleic acid fragments that are complementary to the complete sequences as reported in the accompanying Sequence Listing, as well as those substantially similar nucleic acid sequences, are encompassed in the present disclosure.

The terms "homology" and "homologous" are used interchangeably. They refer to nucleic acid fragments wherein changes in one or more nucleotide bases do not affect the ability of the nucleic acid fragment to mediate gene expression or produce a certain phenotype. These terms also refer to modifications of the nucleic acid fragments such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

Moreover, the skilled artisan recognizes that homologous nucleic acid sequences are also defined by their ability to hybridize, under moderately stringent conditions, e.g., 0.5× SSC, 0.1% SDS, 60° C., with the sequences exemplified herein, or to any portion of the nucleotide sequences disclosed herein and which are functionally equivalent thereto. Stringency conditions can be adjusted to screen for moderately similar fragments, such as homologous sequences from distantly related organisms, to highly similar fragments, such as genes that duplicate functional enzymes from closely related organisms.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% sodium dodecyl sulphate ["SDS"] at 37° C., and a wash in lx to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Specificity is typically the function of post-hybridization washes, the important factors being the ionic strength and temperature of the final wash solution. For DNA-DNA hybrids, the $T_m$ can be approximated from the equation of Meinkoth et al., Anal. Biochem., 138:267-284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; and, low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel et al., Eds., Greene Publishing and Wiley-Interscience, New York (1995). Hybridization and/or wash conditions can be applied for at least 10, 30, 60, 90, 120 or 240 minutes.

"Sequence identity" or "identity" in the context of nucleic acid or polypeptide sequences refers to the nucleic acid bases or amino acid residues in two sequences that are the same when aligned for maximum correspondence over a specified comparison window.

Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

Methods to determine "percent identity" and "percent similarity" are codified in publicly available computer programs. Percent identity and percent similarity can be readily calculated by known methods, including but not limited to those described in: 1) Computational Molecular Biology (Lesk, A. M., Ed.) Oxford University: NY (1988); 2) Biocomputing: Informatics and Genome Projects (Smith, D. W., Ed.) Academic: NY (1993); 3) Computer Analysis of Sequence Data, Part I (Griffin, A. M., and Griffin, H. G., Eds.) Humania: NJ (1994); 4) Sequence Analysis in Molecular Biology (von Heinje, G., Ed.) Academic (1987); and, 5) Sequence Analysis Primer (Gribskov, M. and Devereux, J., Eds.) Stockton: NY (1991).

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" and the "Clustal W method of alignment" (described by Higgins and Sharp, CABIOS, 5:151-153 (1989); Higgins, D. G. et al., Comput. Appl. Biosci., 8:189-191 (1992)) and found in the MegAlign™ (version 8.0.2) program (supra). After alignment of the sequences using either Clustal program, it is possible to obtain a "percent identity" by viewing the "sequence distances" table in the program.

For multiple alignments using the Clustal V method of alignment, the default values correspond to GAP PENALTY=10 and GAP LENGTH PENALTY=10. Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

Default parameters for multiple alignment using the Clustal W method of alignment correspond to GAP PENALTY=10, GAP LENGTH PENALTY=0.2, Delay Divergent Seqs(%)=30, DNA Transition Weight=0.5, Protein Weight Matrix=Gonnet Series, DNA Weight Matrix=IUB.

The "BLASTN method of alignment" is an algorithm provided by the National Center for Biotechnology Information ["NCBI"] to compare nucleotide sequences using default parameters, while the "BLASTP method of alignment" is an algorithm provided by the NCBI to compare protein sequences using default parameters.

It is well understood by one skilled in the art that many levels of sequence identity are useful in identifying polypeptides, from other species, wherein such polypeptides have the same or similar function or activity. Suitable nucleic acid fragments, i.e., isolated polynucleotides according to the disclosure herein, encode polypeptides that are at least about 70-85% identical, while more preferred nucleic acid fragments encode amino acid sequences that are at least about 85-95% identical to the amino acid sequences reported herein. Although preferred ranges are described above, useful examples of percent identities include any integer percentage from 50% to 100%, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Also, of interest is any full-length or partial complement of this isolated nucleotide fragment.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. Accordingly, described herein is any nucleic acid fragment that encodes all or a substantial portion of the amino acid sequence encoding the instant polypeptides as set forth in SEQ ID NO:58, SEQ ID NO:97, SEQ ID NO:139 and SEQ ID NO:179. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These oligonucleotide building blocks are annealed and then ligated to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available. For example, the codon usage profile for Yarrowia lipolytica is provided in U.S. Pat. No. 7,125,672.

"Gene" refers to a nucleic acid fragment that expresses a specific protein, and that may refer to the coding region alone or may include regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene that is introduced into the host organism by gene transfer. Foreign genes can comprise native genes inserted into a non-native organism, native genes introduced into a new location within the native host, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, enhancers, silencers, 5' untranslated leader sequence (e.g., between the transcription start site and translation initiation codon), introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed at almost all stages of development are commonly referred to as "constitutive promoters". It is further recognized that since in most cases the exact boundaries of regulatory sequences (especially at their 5' end) have not been completely defined, DNA fragments of some variation may have identical promoter activity.

The terms "3' non-coding sequences", "transcription terminator" and "termination sequences" refer to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript. A RNA transcript is referred to as the mature RNA when it is a RNA sequence derived from post-transcriptional processing of the primary transcript. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065).

The term "operably linked" refers to the association of nucleic acid sequences on a single nucleic acid fragment so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in a sense or antisense orientation.

The term "recombinant" refers to an artificial combination of two otherwise separated segments of sequence, e.g., by chemical synthesis or by the manipulation of isolated segments of nucleic acids by genetic engineering techniques.

The term "expression", as used herein, refers to the transcription and stable accumulation of sense (mRNA) or antisense RNA. Expression may also refer to translation of mRNA into a protein (either precursor or mature).

"Transformation" refers to the transfer of a nucleic acid molecule into a host organism, resulting in genetically stable inheritance. The nucleic acid molecule may be a plasmid that replicates autonomously, for example, or, it may integrate into the genome of the host organism. Host organisms containing the transformed nucleic acid fragments are referred to as "transgenic", "recombinant", "transformed" or "transformant" organisms.

The terms "plasmid" and "vector" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing an expression cassette(s) into a cell.

The term "expression cassette" refers to a fragment of DNA containing a foreign gene and having elements in addition to the foreign gene that allow for enhanced expression of that gene in a foreign host. Generally, an expression cassette will comprise the coding sequence of a selected gene and regulatory sequences preceding (5' non-coding sequences) and following (3' non-coding sequences) the coding sequence that are required for expression of the selected gene product. Thus, an expression cassette is typically composed of: 1) a promoter sequence; 2) a coding sequence ["ORF"]; and, 3) a 3' untranslated region (i.e., a terminator) that, in eukaryotes, usually contains a polyadenylation site. The expression cassette(s) is usually included within a vector, to facilitate cloning and transformation. Different expression cassettes can be transformed into different organisms including bacteria, yeast, plants and mammalian cells, as long as the correct regulatory sequences are used for each host.

The terms "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a recombinant DNA construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used.

The skilled artisan is well aware of the genetic elements that must be present on the vector in order to successfully transform, select and propagate host cells comprising any of the isolated nucleic acid fragments described herein. The skilled artisan will also recognize that different independent transformation events will result in different levels and patterns of expression (Jones et al., *EMBO J.,* 4:2411-2418 (1985); De Almeida et al., *Mol. Gen. Genetics,* 218:78-86 (1989)), and thus that multiple events must be screened in order to obtain strains displaying the desired expression level and pattern. Such screening may be accomplished by Southern analysis of DNA, Northern analysis of mRNA expression, Western analysis of protein expression, or phenotypic analysis, among others.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1) the GCG suite of programs (Wisconsin Package Version 9.0, Genetics Computer Group (GCG), Madison, Wis.); 2) BLASTP, BLASTN, BLASTX (Altschul et al., *J. Mol. Biol.,* 215:403-410 (1990)); 3) DNAS-TAR (DNASTAR, Inc. Madison, Wis.); 4) Sequencher (Gene Codes Corporation, Ann Arbor, Mich.); and, 5) the FASTA program incorporating the Smith-Waterman algorithm (W. R. Pearson, *Comput. Methods Genome Res.,* [Proc. Int. Symp.] (1994), Meeting Date 1992, 111-20. Editor(s): Suhai, Sandor. Plenum: New York, N.Y.). Within this description, whenever sequence analysis software is used for analysis, the analytical results are based on the "default values" of the program referenced, unless otherwise specified. As used herein "default values" will mean any set of values or parameters that originally load with the software when first initialized.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory: Cold Spring Harbor, N.Y. (1989); by Silhavy, T. J., Bennan, M. L. and Enquist, L. W., *Experiments with Gene Fusions,* Cold Spring Harbor Laboratory: Cold Spring Harbor, N.Y. (1984); and by Ausubel, F. M. et al., *Current Protocols in Molecular Biology,* published by Greene Publishing Assoc. and Wiley-Interscience, Hoboken, N.J. (1987).

In general, lipid accumulation in oleaginous microorganisms is triggered in response to the overall carbon to nitrogen ratio present in the growth medium. This process, leading to the de novo synthesis of free palmitate (16:0) in oleaginous microorganisms, is described in detail in U.S. Pat. No. 7,238, 482. Palmitate is the precursor of longer-chain saturated and unsaturated fatty acid derivates.

The metabolic process wherein oleic acid is converted to ω-3/ω-6 fatty acids involves elongation of the carbon chain through the addition of carbon atoms and desaturation of the molecule through the addition of double bonds. This requires a series of special elongation and desaturation enzymes present in the endoplasmic reticulum membrane. However, as seen in FIG. 1 and as described below, multiple alternate pathways exist for production of a specific ω-3/ω-6 fatty acid.

Specifically, FIG. 1 depicts the pathways described below. All pathways require the initial conversion of oleic acid to linoleic acid ["LA"], the first of the ω-6 fatty acids, by a Δ12 desaturase. Then, using the "Δ9 elongase/Δ8 desaturase pathway" and LA as substrate, long-chain ω-6 fatty acids are formed as follows: 1) LA is converted to eicosadienoic acid ["EDA"] by a Δ9 elongase; 2) EDA is converted to dihomo-γ-linolenic acid ["DGLA"] by a Δ8 desaturase; 3) DGLA is converted to arachidonic acid ["ARA"] by a Δ5 desaturase; 4) ARA is converted to docosatetraenoic acid ["DTA"] by a $C_{20/22}$ elongase; and, 5) DTA is converted to docosapentaenoic acid ["DPAn-6"] by a Δ4 desaturase.

The "Δ9 elongase/Δ8 desaturase pathway" can also use α-linolenic acid ["ALA"] as substrate to produce long-chain ω-3 fatty acids as follows: 1) LA is converted to ALA, the first of the ω-3 fatty acids, by a Δ15 desaturase; 2) ALA is converted to eicosatrienoic acid ["ETrA"] by a Δ9 elongase; 3) ETrA is converted to eicosatetraenoic acid ["ETA"] by a Δ8 desaturase; 4) ETA is converted to eicosapentaenoic acid ["EPA"] by a Δ5 desaturase; 5) EPA is converted to docosapentaenoic acid ["DPA"] by a $C_{20/22}$ elongase; and, 6) DPA is converted to docosahexaenoic acid ["DHA"] by a Δ4 desaturase. Optionally, ω-6 fatty acids may be converted to ω-3 fatty acids. For example, ETA and EPA are produced from DGLA and ARA, respectively, by Δ17 desaturase activity.

Alternate pathways for the biosynthesis of ω-3/ω-6 fatty acids utilize a Δ6 desaturase and $C_{18/20}$ elongase, that is, the "Δ6 desaturase/Δ6 elongase pathway". More specifically, LA and ALA may be converted to GLA and stearidonic acid ["STA"], respectively, by a Δ6 desaturase; then, a $C_{18/20}$ elongase converts GLA to DGLA and/or STA to ETA. Downstream PUFAs are subsequently formed as described above.

It is contemplated that the particular functionalities required to be introduced into a specific host organism for production of ω-3/ω-6 fatty acids will depend on the host cell (and its native PUFA profile and/or desaturase/elongase profile), the availability of substrate, and the desired end product(s). For example, expression of the Δ9 elongase/Δ8 desaturase pathway may be preferred in some embodiments, as opposed to expression of the Δ6 desaturase/Δ6 elongase pathway, since PUFAs produced via the former pathway are devoid of GLA and/or STA.

One skilled in the art will be able to identify various candidate genes encoding each of the enzymes desired for ω-3/ω-6 fatty acid biosynthesis. Useful desaturase and elongase sequences may be derived from any source, e.g., isolated from a natural source (from bacteria, algae, fungi, plants, animals, etc.), produced via a semi-synthetic route or synthesized de novo. Although the particular source of the desaturase and elongase genes introduced into the host is not critical, considerations for choosing a specific polypeptide having desaturase or elongase activity include: 1) the substrate specificity of the polypeptide; 2) whether the polypeptide or a component thereof is a rate-limiting enzyme; 3) whether the desaturase or elongase is essential for synthesis of a desired PUFA; 4) co-factors required by the polypeptide; and/or, 5) whether the polypeptide was modified after its production (e.g., by a kinase or a prenyltransferase). The expressed polypeptide preferably has parameters compatible with the biochemical environment of its location in the host cell (see U.S. Pat. No. 7,238,482 for additional details).

It will also be useful to consider the conversion efficiency of each particular desaturase and/or elongase. More specifically, since each enzyme rarely functions with 100% efficiency to convert substrate to product, the final lipid profile of unpurified oils produced in a host cell will typically be a mixture of various PUFAs consisting of the desired ω-3/ω-6 fatty acid, as well as various upstream intermediary PUFAs. Thus, each enzyme's conversion efficiency is also a variable to consider, when optimizing biosynthesis of a desired fatty acid.

With each of the considerations above in mind, candidate genes having the appropriate desaturase and elongase activities (e.g., Δ6 desaturases, $C_{18/20}$ elongases, Δ5 desaturases, Δ17 desaturases, Δ15 desaturases, Δ9 desaturases, Δ12 desaturases, $C_{14/16}$ elongases, $C_{16/18}$ elongases, Δ9 elongases, Δ8 desaturases, Δ4 desaturases and $C_{20/22}$ elongases) can be identified according to publicly available literature (e.g., GenBank), the patent literature, and experimental analysis of organisms having the ability to produce PUFAs. These genes will be suitable for introduction into a specific host organism, to enable or enhance the organism's synthesis of PUFAs.

Once fatty acids are synthesized within an organism (including saturated and unsaturated fatty acids and short-chain and long-chain fatty acids), they may be incorporated into triacylglycerides ["TAGs"]. TAGs, the primary storage unit for fatty acids, are formed by a series of reactions that involve: 1) the esterification of one molecule of acyl-CoA to glycerol-3-phosphate via an acyltransferase to produce lysophosphatidic acid; 2) the esterification of a second molecule of acyl-CoA via an acyltransferase to yield 1,2-diacylglycerol phosphate (commonly identified as phosphatidic acid); 3) removal of a phosphate by phosphatidic acid phosphatase to yield 1,2-diacylglycerol; and, 4) the addition of a third fatty acid by the action of an acyltransferase to form TAG.

Although Δ5 desaturases contain several conserved sequences (i.e., the three histidine boxes [H(X)$_{3-4}$H (SEQ ID NOs:1 and 2), H(X)$_{2-3}$HH (SEQ ID NOs:3 and 4) and H/Q (X)$_{2-3}$HH (SEQ ID NOs:5 and 6)] and the cytochrome $b_5$ domain), only the heme-binding motif (i.e., His-Pro-Gly-Gly or HPGG [SEQ ID NO:180]) lacks variation within the sequence. It was this motif that was first selected as a target for mutagenesis. The literature suggests that the histidine residue within the HPGG motif is important for function (Sayanova, O. et al., *Plant Physiol.*, 121:641 (1999); Guillou, H., et al., *J. Lipid Res.*, 45:32-40 (2004); Hongsthong, A. et al., *Appl. Microbiol. Biotechnol.*, 72:1192-1201 (2006)). Consequently, substitutions for the histidine residue were avoided in favor of substitutions for the proline and glycine residues.

Site-directed mutagenesis was independently performed on the proline and the second glycine within the HPGG motif of several Δ5 desaturases, followed by expression of the resulting mutant polypeptides and determination of their activities with respect to that of the wildtype enzyme. Surprisingly, various mutant Δ5 desaturases were created comprising amino acid mutant motifs including HXGG (SEQ ID NO:181) and HPGX (SEQ ID NO:182), where the Δ5 desaturase activity of the mutant Δ5 desaturase was functionally equivalent to the Δ5 desaturase activity of the corresponding wildtype Δ5 desaturase.

Oligonucleotide-mediated site-directed mutagenesis was utilized to create specific point mutations within the HPGG motif of various target Δ5 desaturases. Numerous site-directed mutagenesis protocols exist (e.g., Ishii, T. M., et al., *Methods Enzymol.*, 293:53-71 (1998); Ling M. M. and B. H. Robinson, *Anal. Biochem.*, 254:157-178 (1997); Braman J. (ed.) *In Vitro Mutagenesis Protocols.* $2^{nd}$ Ed., Humania: Totowa, N.J. (2002); Kunkel T. A., et al., *Methods Enzymol.*, 154:367-382 (1987); Sawano A. and Miyawaki, A. *Nucleic Acids Res.*, 28:e78 (2000)); however, the QuikChange® site-directed mutagenesis kit (Stratagene, La Jolla, Calif.) was selected for use based on its facile implementation and high efficiency. The basic procedure utilizes a supercoiled double-stranded DNA vector with an insert of interest and two synthetic oligonucleotide primers containing the desired mutation. The oligonucleotide primers, each complementary to opposite strands of the vector, are extended during temperature cycling by a DNA polymerase. Incorporation of the oligonucleotide primers generates a mutated plasmid containing staggered nicks. Following temperature cycling, the product is treated with Dpn I endonuclease (specific for methylated and hemi-methylated DNA) as a means to digest the parental DNA template and to select for newly synthesized mutant DNA. The nicked vector DNA containing the desired mutations is then transformed and propagated in an *Escherichia coli* host.

Using the techniques described above, all possible amino acid substitutions were introduced by site-directed mutagenesis into a synthetic Δ5 desaturase, codon-optimized for expression in *Yarrowia lipolytica* and derived from *Euglena gracilis* (i.e., EgD5S; SEQ ID NO:10; U.S. Pat. Appl. Pub. No. 2007-0277266-A1), within a plasmid construct comprising a chimeric FBAIN::EgD5S::Pex20 gene. The mutants were transformed into *E. coli*, sequenced and then transformed into an appropriate strain of *Y. lipolytica* previously engineered to produce ~18% DGLA. This enabled screening for Δ5 desaturase activity based on GC analyses and the production of ARA.

Many mutations were identified that resulted in a completely non-functional mutant Δ5 desaturase (i.e., having no detectable Δ5 desaturase activity) or a mutant Δ5 desaturase having substantially decreased Δ5 desaturase activity with respect to the non-mutant wildtype enzyme. Surprisingly, however, the preliminary screening identified three amino acid residues that could be substituted for the proline within the HPGG motif and that resulted in approximately equivalent or increased Δ5 desaturase activity in the mutant, when compared to the Δ5 desaturase activity in the corresponding wildtype enzyme (i.e., EgD5S). Thus, this preliminary experimentation suggested that the proline residue within the HPGG motif could be substituted with several amino acids without significantly affecting the Δ5 desaturase activity of EgD5S.

Similar experimentation was performed using EgD5S as the template in site-directed mutagenesis reactions, where the second glycine residue of the HPGG motif was mutated. As described above, analyses of the mutant enzymes determined that 2 amino acid residues were sufficient to replace the wildtype amino acid (i.e., glycine) and resulted in a mutant EgD5S enzyme having equivalent or improved Δ5 desaturase activity.

Once the preliminary analyses of amino acid substitutions in the HPGG motif of EgD5S were completed as described above, a quantitative analysis of those mutants that performed at or above the wildtype EgD5S conversion rate was carried out by re-transformation of each mutant EgD5S-containing plasmid into the host strain of *Yarrowia lipolytica*. GC analysis of the fatty acid methyl esters ["FAMEs"] produced confirmed that Δ5 desaturase activity of three of the initial five mutants performed with increased activity when compared to the corresponding wildtype EgD5S control.

The above experimental protocol was repeated using a synthetic Δ5 desaturase, codon-optimized for expression in *Yarrowia lipolytica* and derived from *Euglena anabaena* (i.e., EaD5S; SEQ ID NO:14; U.S. Pat. Appl. Pub. No. 2008-0274521-A1) and a synthetic Δ5 desaturase, codon-optimized for expression in *Y. lipolytica* and derived from *Peridinium* sp. CCMP626 (i.e., RD5S; SEQ ID NO:18; U.S. Pat. Appl. Pub. No. 2007-0271632-A1). Results of all site-directed mutagenesis that resulted in an equivalent or increased Δ5 desaturase activity within the mutant as compared to the corresponding wildtype enzyme (i.e., EgD5S, EaD5S or RD5S) are summarized below in Table 3 (see Examples for additional details). Mutants are designated using the following nomenclature, detailing: 1) Wildtype Enzyme; 2) hyphen (-); 3) mutant HPGG motif. Thus, for example, the mutant enzyme created from the synthetic, codon-optimized EgD5S (i.e., SEQ ID NO:10), having a histidine for proline substitution at amino acid 2 (i.e., a P2 to H substitution) of the HPGG motif is identified as EgD5S-HHGG.

TABLE 3

HPGG Motif Mutants Resulting In
Increased Δ5 Desaturase Activity

| Mutant Δ5 Desaturase | SEQ ID NO of Mutant Δ5 Desaturase | Δ5 Desaturase Activity |
| --- | --- | --- |
| EgD5S-HGGG | SEQ ID NO: 58 | 104.6% |
| EgD5S-HHGG | SEQ ID NO: 58 | 103.6% |
| EgD5S-HPGS | SEQ ID NO: 97 | 106.9% |
| EaD5S-HCGG | SEQ ID NO: 139 | 107.9% |
| RD5S-HCGG | SEQ ID NO: 179 | 138.6%* |
| RD5S-HWGG | SEQ ID NO: 179 | 113.5%* |

*% Increase in the Δ5 desaturase activity of the mutant enzyme with respect to the corresponding wildtype non-mutant enzyme is reported based on initial assay results and not quantitative analysis.

The above data does not suggest a consensus with respect to which particular amino acid substitution is sufficient to produce a mutant polypeptide having increased Δ5 desaturase activity. However, contrary to the above mentioned reports in the art, the data is surprising in demonstrating that substitutions for either the proline or glycine residues may result in an enzyme having higher Δ5 desaturase activity than its wildtype parent. Accordingly, it is within the scope of the present invention to provide a polypeptide having Δ5 desaturase activity comprising an amino acid motif selected from the group consisting of: SEQ ID NO:183 (HGGG), SEQ ID NO:184 (HHGG), SEQ ID NO:186 (HCGG), SEQ ID NO:187 (HWGG) and SEQ ID NO:185 (HPGS). Preferably, the polypeptide has the amino acid sequence selected from the group consisting of: SEQ ID NO:58 (EgD5S-HGGG and EgD5S-HHGG), SEQ ID NO:97 (EgD5S-HPGS), SEQ ID NO:139 (EaD5S-HCGG) and SEQ ID NO:179 (RD5S-HCGG and RD5S-HWGG). More preferably, the mutant Δ5 desaturase: 1) comprises a mutant amino acid motif selected from the group consisting of: SEQ ID NO:183 (HGGG), SEQ ID NO:184 (HHGG), SEQ ID NO:186 (HCGG), SEQ ID NO:187 (HWGG) and SEQ ID NO:185 (HPGS); and, 2) the mutant Δ5 desaturase activity is increased relative to the corresponding wildtype Δ5 desaturase having a HPGG (SEQ ID NO:180) amino acid motif.

It will be appreciated by one of skill in the art that useful mutant Δ5 desaturases are not limited to the mutations described above. Instead, the results suggest that similar experimentation could be performed using any Δ5 wildtype desaturase enzyme having a HPGG (SEQ ID NO:180) motif within the cytochrome b₅ domain, to thereby engineer a mutant Δ5 desaturase having increased Δ5 desaturase activity wherein the mutation would result in a mutant HXGG motif (SEQ ID NO:181) or a HPGX (SEQ ID NO:182) motif. A mutant enzyme having increased Δ5 desaturase activity can be useful to enable increased production of ω-3/ω-6 fatty acids.

For example, in vitro mutagenesis and selection or error prone PCR (Leung et al., *Techniques*, 1:11-15 (1989); Zhou et al., *Nucleic Acids Res.*, 19:6052-6052 (1991); Spee et al., *Nucleic Acids Res.*, 21:777-778 (1993); Melnikov et al., *Nucleic Acids Res.*, 27(4):1056-1062 (Feb. 15, 1999)) could also be employed as a means to obtain mutations of naturally occurring Δ5 desaturase genes, such as EgD5S, EaD5S or RD5S, wherein the mutations may include deletions, insertions and point mutations, or combinations thereof. The principal advantage of error-prone PCR is that all mutations introduced by this method will be within the desired desaturase gene, and any change may be easily controlled by changing the PCR conditions. Alternatively, in vivo mutagenesis may be employed using commercially available materials such as the *E. coli* XL1-Red strain and *Epicurian coli* XL1-Red mutator strain from Stratagene (La Jolla, Calif.; Greener and Callahan, *Strategies*, 7:32-34 (1994)). This strain is deficient in three of the primary DNA repair pathways (mutS, mutD and mutT), resulting in a mutation rate 5000-fold higher than that of wildtype. In vivo mutagenesis does not depend on ligation efficiency (as with error-prone PCR); however, a mutation may occur at any region of the vector and the mutation rates are generally much lower.

It is also contemplated that a mutant Δ5 desaturase enzyme with altered or enhanced Δ5 desaturase activity may be constructed using the method of "gene shuffling" (U.S. Pat. No. 5,605,793; U.S. Pat. No. 5,811,238; U.S. Pat. No. 5,830,721; U.S. Pat. No. 5,837,458). The method of gene shuffling is particularly attractive due to its facile implementation and high rate of mutagenesis. The process of gene shuffling involves the restriction of a gene of interest into fragments of specific size in the presence of additional populations of DNA regions of both similarity to (or difference to) the gene of interest. This pool of fragments will denature and then reanneal to create a mutated gene. The mutated gene is then screened for altered activity. Any of these methods may be used to create Δ5 desaturase mutant enzymes having the substituted motifs HXGG (SEQ ID NO:181) and HPGX (SEQ ID NO:182), which may then be screened for improved activity using the methods described herein.

It is expected that introduction of chimeric genes encoding the mutant Δ5 desaturases described herein (i.e., wherein said mutant Δ5 desaturase comprises at least at one mutation in a region encoding an HPGG amino acid motif and wherein said mutant Δ5 desaturase has increased Δ5 desaturase activity with respect to that of the corresponding wildtype Δ5 desaturase), under the control of the appropriate promoters will result in increased production of ARA and/or EPA in the transformed host organism, respectively. As such, disclosed herein are methods for the direct production of PUFAs comprising exposing a fatty acid substrate (i.e., DGLA and/or ETA) to a mutant desaturase enzyme described herein (e.g., SEQ ID NO:58 [EgD5S-HGGG and EgD5S-HHGG], SEQ ID NO:97 [EgD5S-HPGS], SEQ ID NO:139 [EaD5S-HCGG], SEQ ID NO:179 [RD5S-HCGG and RD5S-HWGG]), such that the substrate is converted to the desired fatty acid product (i.e., ARA and/or EPA, respectively).

More specifically, described herein is a method for the production of ARA in a microbial host cell (e.g., bacteria, yeast, algae, euglenoids, stramenopiles, oomycetes and fungi), wherein the microbial host cell comprises:
a) a polypeptide having Δ5 desaturase activity comprising an amino acid motif selected from the group consisting of: SEQ ID NO:183 (HGGG), SEQ ID NO:184 (HHGG), SEQ ID NO:186 (HCGG), SEQ ID NO:187 (HWGG) and SEQ ID NO:185 (HPGS); and,
b) a source of DGLA;

wherein the host cell is grown under conditions such that the mutant Δ5 desaturase is expressed and the DGLA is converted to ARA, and wherein the ARA is optionally recovered.

In another method described herein, the mutant Δ5 desaturase may be used for the conversion of ETA to EPA. Accordingly set forth is a method for the production of EPA, wherein the host cell comprises:
a) a polypeptide having Δ5 desaturase activity comprising an amino acid motif selected from the group consisting of: SEQ ID NO:183 (HGGG), SEQ ID NO:184 (HHGG), SEQ ID NO:186 (HCGG), SEQ ID NO:187 (HWGG) and SEQ ID NO:185 (HPGS); and,
b) a source of ETA;

wherein the host cell is grown under conditions such that the mutant Δ5 desaturase is expressed and the ETA is converted to EPA, and wherein the EPA is optionally recovered.

Alternatively, each mutant Δ5 desaturase gene and its corresponding enzyme product described herein can be used indirectly for the production of various ω-6 and ω-3 PUFAs (see FIG. 1; U.S. Pat. No. 7,238,482; Intl. App. Pub. No. WO 2007/136671 and Intl. App. Pub. No. WO 2007/136646). Indirect production of ω-3/ω-6 PUFAs occurs wherein the fatty acid substrate is converted indirectly into the desired fatty acid product, via means of an intermediate step(s) or pathway intermediate(s). Thus, it is contemplated that the mutant Δ5 desaturases described herein may be expressed in conjunction with additional genes encoding enzymes of the PUFA biosynthetic pathway (e.g., Δ6 desaturases, $C_{18/20}$ elongases, Δ17 desaturases, Δ8 desaturases, Δ15 desaturases, Δ9 desaturases, Δ12 desaturases, $C_{14/16}$ elongases, $C_{16/18}$ elongases, Δ9 elongases, Δ5 desaturases, Δ4 desaturases, $C_{20/22}$ elongases) to result in higher levels of production of longer-chain ω-3/ω-6 fatty acids, such as e.g., ARA, EPA, DTA, DPAn-6, DPA and/or DHA.

Preferably, the Δ5 desaturases described herein will minimally be expressed in conjunction with a Δ9 elongase and a Δ8 desaturase. The Δ5 desaturases could also be minimally expressed in conjunction with a Δ6 desaturase and a Δ6 elongase. However, the particular genes included within a particular expression cassette will depend on the host cell (and its PUFA profile and/or desaturase/elongase profile), the availability of substrate and the desired end product(s).

It is necessary to create and introduce a recombinant construct comprising an ORF encoding a mutant Δ5 desaturase (i.e., wherein said mutant comprises an amino acid motif selected from the group consisting of: SEQ ID NO:183 (HGGG), SEQ ID NO:184 (HHGG), SEQ ID NO:186 (HCGG), SEQ ID NO:187 (HWGG) and SEQ ID NO:185 (HPGS)) into a suitable host cell. One of skill in the art is aware of standard resource materials that describe: 1) specific conditions and procedures for construction, manipulation and isolation of macromolecules, such as DNA molecules, plasmids, etc.; 2) generation of recombinant DNA fragments and recombinant expression constructs; and, 3) screening and isolating of clones. See, Sambrook, J., Fritsch, E. F. and Maniatis, T., Molecular Cloning: A Laboratory Manual, 2$^{nd}$ ed., Cold Spring Harbor Laboratory: Cold Spring Harbor, N.Y. (1989) (hereinafter "Maniatis"); by Silhavy, T. J., Bennan, M. L. and Enquist, L. W., Experiments with Gene Fusions, Cold Spring Harbor Laboratory: Cold Spring Harbor, N.Y. (1984); and by Ausubel, F. M. et al., Current Protocols in Molecular Biology, published by Greene Publishing Assoc. and Wiley-Interscience, Hoboken, N.J. (1987).

In general, the choice of sequences included in the construct depends on the desired expression products, the nature of the host cell and the proposed means of separating transformed cells versus non-transformed cells. The skilled artisan is aware of the genetic elements that must be present on the plasmid vector to successfully transform, select and propagate host cells containing the chimeric gene. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation, i.e., a promoter, the gene coding sequence, and a region 3' of the DNA fragment that controls transcriptional termination, i.e., a terminator. It is most preferred when both control regions are derived from genes from the transformed host cell, although they need not be derived from the genes native to the production host.

Transcriptional initiation control regions (also initiation control regions or promoters) useful for driving expression of the instant Δ5 desaturase ORFs in the desired microbial host cell are well known. These control regions may comprise a promoter, enhancer, silencer, intron sequences, 3' UTR and/or 5' UTR regions, and protein and/or RNA stabilizing elements. Such elements may vary in their strength and specificity. Virtually any promoter, i.e., native, synthetic, or chimeric, capable of directing expression of these genes in the selected host cell is suitable, although transcriptional and translational regions from the host species are particularly useful. Expression in a host cell can be accomplished in an induced or constitutive fashion. Induced expression occurs by inducing the activity of a regulatable promoter operably linked to the gene of interest, while constitutive expression occurs by the use of a constitutive promoter.

When the host cell is yeast, transcriptional and translational regions functional in yeast cells are provided, particularly from the host species. See, e.g., U.S. Pat. Appl. Pub. No. 2006-0115881-A1, corresponding to Intl. App. Pub. No. WO 2006/052870 for preferred transcriptional initiation regulatory regions for use in *Yarrowia lipolytica*. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the desired polypeptide is poorly expressed in yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

3' non-coding sequences encoding transcription termination regions may be provided in a recombinant construct and may be from the 3' region of the gene from which the initiation region was obtained or from a different gene. A large number of termination regions are known and function satisfactorily in a variety of hosts, when utilized both in the same and different genera and species from which they were derived. Termination regions may also be derived from various genes native to the preferred hosts. The termination region usually is selected more as a matter of convenience rather than because of any particular property. The 3'-region can also be synthetic, as one of skill in the art can utilize available information to design and synthesize a 3'-region sequence that functions as a transcription terminator. A termination site may be unnecessary, but is highly preferred.

Merely inserting a gene into a cloning vector does not ensure its expression at the desired rate, concentration, amount, etc. In response to the need for a high expression rate, many specialized expression vectors have been created by adjusting certain properties that govern transcription, RNA stability, translation, protein stability and location, oxygen limitation and secretion from the microbial host cell. These properties include: the nature of the relevant transcriptional promoter and terminator sequences; the number of copies of the cloned gene (wherein additional copies may be cloned within a single expression construct and/or additional copies may be introduced into the host cell by increasing the plasmid copy number or by multiple integration of the cloned gene into the genome); whether the gene is plasmid-borne or integrated into the host cell genome; the final cellular location of the synthesized foreign protein; the efficiency of translation and correct folding of the protein in the host organism; the intrinsic stability of the mRNA and protein of the cloned gene within the host cell; and, the codon usage within the cloned gene, such that its frequency approaches the frequency of preferred codon usage of the host cell. Each of these may be used in the methods and host cells described herein, to further optimize expression of the mutant Δ5 desaturases.

After a recombinant construct is created comprising at least one chimeric gene comprising a promoter, a Δ5 desaturase ORF and a terminator, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene(s) of interest may be introduced into a microbial host cell by any standard technique. These techniques include transformation, e.g., lithium acetate transformation (*Methods in Enzymology*, 194:186-187 (1991)), bolistic impact, electroporation, microinjection, or any other method that introduces the gene(s) of interest into the host cell.

For convenience, a host cell that has been manipulated by any method to take up a DNA sequence, for example, in an expression cassette, is referred to herein as "transformed", "transformant" or "recombinant". The transformed host will have at least one copy of the expression construct and may have two or more, depending upon whether the expression cassette is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells.

Typically, transformed hosts are selected for their ability to grow on selective media, which may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. Additional selection techniques are described in U.S. Pat. No. 7,238,482, U.S. Pat. No. 7,259,255 and Intl. App. Pub. No. WO 2006/052870.

Following transformation, substrates suitable for the instant mutant Δ5 desaturases (and, optionally other PUFA enzymes that are co-expressed within the host cell) may be produced by the host either naturally or transgenically, or they may be provided exogenously.

A variety of eukaryotic organisms are suitable as host, to thereby yield a transformant comprising mutant Δ5 desaturases as described herein, including bacteria, yeast, algae, stramenopiles, oomycetes, euglenoids and/or fungi. This is contemplated because transcription, translation and the protein biosynthetic apparatus is highly conserved. Thus, suitable hosts may include those that grow on a variety of feedstocks, including simple or complex carbohydrates, fatty acids, organic acids, oils, glycerols and alcohols, and/or hydrocarbons over a wide range of temperature and pH values.

Preferred microbial hosts are oleaginous organisms. These oleaginous organisms are naturally capable of oil synthesis and accumulation, wherein the total oil content can comprise greater than about 25% of the dry cell weight, more preferably greater than about 30% of the dry cell weight, and most preferably greater than about 40% of the dry cell weight. Various bacteria, algae, euglenoids, moss, fungi, yeast and stramenopiles are naturally classified as oleaginous. In alternate embodiments, a non-oleaginous organism can be genetically modified to become oleaginous, e.g., yeast such as *Saccharomyces cerevisiae*.

In more preferred embodiments, the microbial host cells are oleaginous yeast. Genera typically identified as oleaginous yeast include, but are not limited to: *Yarrowia, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis*, and *Yarrowia lipolytica* (formerly classified as *Candida lipolytica*). Alternately, oil biosynthesis may be genetically engineered such that the microbial host cell (e.g., a yeast) can produce more than 25% oil of the cellular dry weight, and thereby be considered oleaginous.

Most preferred is the oleaginous yeast *Yarrowia lipolytica*. In a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.*, 82(1):43-9 (2002)).

Specific teachings applicable for transformation of oleaginous yeasts (i.e., *Yarrowia lipolytica*) include U.S. Pat. No. 4,880,741 and U.S. Pat. No. 5,071,764 and Chen, D. C. et al. (*Appl. Microbiol. Biotechnol.*, 48(2):232-235 (1997)). Specific teachings applicable for engineering ARA, EPA and DHA production in *Y. lipolytica* are provided in U.S. patent application Ser. No. 11/264,784 (Intl. App. Pub. No. WO 2006/055322), U.S. patent application Ser. No. 11/265,761 (Intl. App. Pub. No. WO 2006/052870) and U.S. patent application Ser. No. 11/264,737 (Intl. App. Pub. No. WO 2006/052871), respectively.

The preferred method of expressing genes in this yeast is by integration of linear DNA into the genome of the host. Integration into multiple locations within the genome can be particularly useful when high level expression of genes is desired, such as into the Ura3 locus (GenBank Accession No. AJ306421), the Leu2 gene locus (GenBank Accession No. AF260230), the Lys5 gene locus (GenBank Accession No. M34929), the Aco2 gene locus (GenBank Accession No. AJ001300), the Pox3 gene locus (Pox3: GenBank Accession No. XP_503244; or, Aco3: GenBank Accession No. AJ001301), the Δ12 desaturase gene locus (U.S. Pat. No. 7,214,491), the Lip1 gene locus (GenBank Accession No. Z50020), the Lip2 gene locus (GenBank Accession No. AJ012632), the SCP2 gene locus (GenBank Accession No. AJ431362), Pex3 gene locus (GenBank Accession No. CAG78565), Pex16 gene locus (Gen Bank Accession No. CAG79622), and/or the Pex10 gene locus (GenBank Accession No. CAG81606).

Preferred selection methods for use in *Yarrowia lipolytica* are resistance to kanamycin, hygromycin and the amino glycoside G418, as well as ability to grow on media lacking uracil, leucine, lysine, tryptophan or histidine. 5-fluoroorotic acid (5-fluorouracil-6-carboxylic acid monohydrate; "5-FOA") may also be especially useful for the selection of yeast Ura⁻ mutants (U.S. Pat. Appl. Pub. No. 2009-0093543-A1), or a native acetohydroxyacid synthase (or acetolactate synthase; E.C. 4.1.3.18) that confers sulfonyl urea herbicide resistance (Intl. App. Pub. No. WO 2006/052870) is utilized for selection of transformants. A unique method of "recycling" a pair of preferred selection markers for their use in multiple sequential transformations, by use of site-specific recombinase systems, is also taught in U.S. Pat. Appl. Pub. No. 2009-0093543-A1.

Based on the above, disclosed herein is a method of producing either ARA or EPA, respectively, comprising:
(a) providing an oleaginous yeast (e.g., *Yarrowia lipolytica*) comprising:
  (i) a first recombinant nucleotide molecule encoding a mutant Δ5 desaturase polypeptide, operably linked to at least one regulatory sequence; and,
  (ii) a source of desaturase substrate consisting of DGLA and/or ETA, respectively; and,
(b) growing the yeast of step (a) in the presence of a suitable fermentable carbon source wherein the gene encoding the mutant Δ5 desaturase polypeptide is expressed and DGLA is converted to ARA and/or ETA is converted to EPA, respectively; and,
(c) optionally recovering the ARA and/or EPA, respectively, of step (b).

Substrate feeding may be required. In preferred embodiments, the mutant Δ5 desaturase polypeptide is selected from the group consisting of SEQ ID NO:58, SEQ ID NO:97, SEQ ID NO:139 and SEQ ID NO:179. Thus, for example, the nucleotide sequence of the gene encoding the mutant Δ5 desaturase polypeptide may be, for example, selected from the group consisting of SEQ ID NO:191, SEQ ID NO:192, SEQ ID NO:193, SEQ ID NO:194 and SEQ ID NO:195.

Since naturally produced PUFAs in oleaginous yeast are limited to 18:2 fatty acids (i.e., LA), and less commonly, 18:3 fatty acids (i.e., ALA), the oleaginous yeast may be genetically engineered to express multiple enzymes necessary for long-chain PUFA biosynthesis (thereby enabling production of e.g., DPAn-6, DPA and DHA), in addition to the mutant Δ5 desaturases described herein.

Specifically, an oleaginous yeast is contemplated herein, wherein said yeast comprises:

a) a first recombinant DNA construct comprising an isolated polynucleotide encoding a mutant Δ5 desaturase polypeptide, operably linked to at least one regulatory sequence; and, b) at least one additional recombinant DNA construct comprising an isolated polynucleotide, operably linked to at least one regulatory sequence, encoding a polypeptide selected from the group consisting of: Δ4 desaturase, Δ6 desaturase, Δ9 desaturase, Δ12 desaturase, Δ15 desaturase, Δ17 desaturase, Δ8 desaturase, Δ9 elongase, $C_{14/16}$ elongase, $C_{16/18}$ elongase, $C_{18/20}$ elongase and $C_{20/22}$ elongase.

Other suitable microbial hosts include oleaginous bacteria, algae, euglenoids, stramenopiles, oomycetes and fungi. Within this broad group of microbial hosts, of particular interest are microorganisms that synthesize ω-3/ω-6 fatty acids, or those that can be genetically engineered for this purpose (e.g., other yeast such as *Saccharomyces cerevisiae*). Thus, for example, transformation of *Mortierella alpina* (which is commercially used for production of ARA) with any of the present Δ5 desaturase genes under the control of inducible or regulated promoters could yield a transformant organism capable of synthesizing increased quantities of ARA. The method of transformation of *M. alpina* is described by Mackenzie et al. (*Appl. Environ. Microbiol.*, 66:4655 (2000)). Similarly, methods for transformation of Thraustochytriales microorganisms (e.g., *Thraustochytrium*, *Schizochytrium*) are disclosed in U.S. Pat. No. 7,001,772.

Irrespective of the host selected for expression of the mutant Δ5 desaturases described herein, multiple transformants must be screened in order to obtain a strain displaying the desired expression level and pattern. For example, Juretzek et al. (*Yeast*, 18:97-113 (2001)) note that the stability of an integrated DNA fragment in *Yarrowia lipolytica* is dependent on the individual transformants, the recipient strain and the targeting platform used. Such screening may be accomplished by Southern analysis of DNA blots (Southern, *J. Mol. Biol.*, 98:503 (1975)), Northern analysis of mRNA expression (Kroczek, *J. Chromatogr. Biomed. Appl.*, 618(1-2):133-145 (1993)), Western and/or Elisa analyses of protein expression, phenotypic analysis or GC analysis of the PUFA products.

Knowledge of the sequences of the present mutant Δ5 desaturases will be useful for manipulating ω-3 and/or ω-6 fatty acid biosynthesis in various host cells. Methods for manipulating biochemical pathways are well known to those skilled in the art; and, it is expected that numerous manipulations will be possible to maximize ω-3 and/or ω-6 fatty acid biosynthesis in oleaginous yeasts, and particularly, in *Yarrowia lipolytica*. This manipulation may require metabolic engineering directly within the PUFA biosynthetic pathway or additional manipulation of pathways that contribute carbon to the PUFA biosynthetic pathway. Methods useful for up-regulating desirable biochemical pathways and down-regulating undesirable biochemical pathways are well known to those skilled in the art.

For example, biochemical pathways competing with the ω-3 and/or ω-6 fatty acid biosynthetic pathways for energy or carbon, or native PUFA biosynthetic pathway enzymes that interfere with production of a particular PUFA end-product, may be eliminated by gene disruption or down-regulated by other means, e.g., antisense mRNA.

Detailed discussion of manipulations within the PUFA biosynthetic pathway as a means to increase ARA, EPA or DHA and associated techniques thereof are presented in Intl. App. Pub. No. WO 2006/055322 [U.S. Pat. Appl. Pub. No. 2006-0094092-A1], Intl. App. Pub. No. WO 2006/052870 [U.S. Pat. Appl. Pub. No. 2006-0115881-A1] and Intl. App. Pub. No. WO 2006/052871 [U.S. Pat. Appl. Pub. No. 2006-0110806-A1], respectively, as are desirable manipulations in the TAG biosynthetic pathway and the TAG degradation pathway (and associated techniques thereof).

It may be useful to modulate the expression of the fatty acid biosynthetic pathway by any one of the strategies described above. For example, provided herein are methods whereby genes encoding key enzymes in the Δ9 elongase/Δ8 desaturase biosynthetic pathway and Δ6 desaturase/Δ6 elongase biosynthetic pathway are introduced into oleaginous yeasts for the production of ω-3 and/or ω-6 fatty acids. It will be particularly useful to express the present mutant Δ5 desaturase genes in oleaginous yeasts that do not naturally possess ω-3 and/or ω-6 fatty acid biosynthetic pathways and coordinate the expression of these genes, to maximize production of preferred PUFA products using various means for metabolic engineering of the host organism.

The transformed microbial host cell is grown under conditions that optimize expression of chimeric genes (e.g., desaturase, elongase) and produce the greatest and most economical yield of desired PUFAs. In general, media conditions that may be optimized include the type and amount of carbon source, the type and amount of nitrogen source, the carbon-to-nitrogen ratio, the amount of different mineral ions, the oxygen level, growth temperature, pH, length of the biomass production phase, length of the oil accumulation phase and the time and method of cell harvest. Microorganisms of interest, such as oleaginous yeast (e.g., *Yarrowia lipolytica*) are generally grown in a complex medium such as yeast extract-peptone-dextrose broth ["YPD"] or a defined minimal media that lacks a component necessary for growth and thereby forces selection of the desired expression cassettes (e.g., Yeast Nitrogen Base (DIFCO Laboratories, Detroit, Mich.)).

Fermentation media for the methods and host cells described herein must contain a suitable carbon source such as are taught in U.S. Pat. No. 7,238,482. Although it is contemplated that the source of carbon utilized in the methods herein may encompass a wide variety of carbon-containing sources, preferred carbon sources are sugars (e.g., glucose), glycerols, and/or fatty acids.

Nitrogen may be supplied from an inorganic (e.g., $(NH_4)_2SO_4$) or organic (e.g., urea or glutamate) source. In addition to appropriate carbon and nitrogen sources, the fermentation media must also contain suitable minerals, salts, cofactors, buffers, vitamins and other components known to those skilled in the art suitable for the growth of the oleaginous host and promotion of the enzymatic pathways necessary for PUFA production. Particular attention is given to several metal ions, such as $Fe^{+2}$, $Cu^{+2}$, $Mn^{+2}$, $Co^{+2}$, $Zn^{+2}$ and $Mg^{+2}$, that promote synthesis of lipids and PUFAs (Nakahara, T. et al., *Ind. Appl. Single Cell Oils*, D. J. Kyle and R. Colin, eds. pp 61-97 (1992)).

Preferred growth media for the methods and host cells described herein are common commercially prepared media, such as Yeast Nitrogen Base (DIFCO Laboratories, Detroit, Mich.). Other defined or synthetic growth media may also be used and the appropriate medium for growth of the transformant host cells will be known by one skilled in the art of microbiology or fermentation science. A suitable pH range for the fermentation is typically between about pH 4.0 to pH 8.0, wherein pH 5.5 to pH 7.5 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast (e.g., *Yarrowia lipolytica*). This approach is described in U.S. Pat. No. 7,238,482, as are various suitable fermentation process designs (i.e., batch, fed-batch and continuous) and considerations during growth.

PUFAs may be found in the host microorganisms as free fatty acids or in esterified forms such as acylglycerols, phospholipids, sulfolipids or glycolipids, and may be extracted from the host cells through a variety of means well-known in the art. One review of extraction techniques, quality analysis and acceptability standards for yeast lipids is that of Z. Jacobs (*Critical Reviews in Biotechnology*, 12(516):463-491 (1992)). A brief review of downstream processing is also available by A. Singh and O. Ward (*Adv. Appl. Microbiol.*, 45:271-312 (1997)).

In general, means for the purification of PUFAs may include extraction (e.g., U.S. Pat. No. 6,797,303 and U.S. Pat. No. 5,648,564) with organic solvents, sonication, supercritical fluid extraction (e.g., using carbon dioxide), saponification and physical means such as presses, or combinations thereof. See U.S. Pat. No. 7,238,482 for additional details.

There are a plethora of food and feed products incorporating ω-3 and/or ω-6 fatty acids, particularly e.g., ALA, GLA, ARA, EPA, DPA and DHA. It is contemplated that the microbial biomass comprising long-chain PUFAs, partially purified microbial biomass comprising PUFAs, purified microbial oil comprising PUFAs, and/or purified PUFAs will function in food and feed products to impart the health benefits of current formulations. More specifically, oils containing ω-3 and/or ω-6 fatty acids will be suitable for use in a variety of food and feed products including, but not limited to: food analogs, meat products, cereal products, baked foods, snack foods and dairy products (see U.S. Pat. Appl. Pub. No. 2006-0094092 for details).

The present compositions may be used in formulations to impart health benefit in medical foods including medical nutritionals, dietary supplements, infant formula and pharmaceuticals. One of skill in the art of food processing and food formulation will understand how the amount and composition of the present oils may be added to the food or feed product. Such an amount will be referred to herein as an "effective" amount and will depend on the food or feed product, the diet that the product is intended to supplement or the medical condition that the medical food or medical nutritional is intended to correct or treat.

EXAMPLES

The present invention is further described in the following Examples, which illustrate reductions to practice of the invention but do not completely define all of its possible variations.

General Methods

Standard recombinant DNA and molecular cloning techniques used in the Examples are well known in the art and are described by: 1) Sambrook, J., Fritsch, E. F. and Maniatis, T., *Molecular Cloning: A Laboratory Manual*; Cold Spring Harbor Laboratory: Cold Spring Harbor, N.Y. (1989) (Maniatis); 2) T. J. Silhavy, M. L. Bennan, and L. W. Enquist, Experiments with Gene Fusions; Cold Spring Harbor Laboratory: Cold Spring Harbor, N.Y. (1984); and, 3) Ausubel, F. M. et al., Current Protocols in Molecular Biology, published by Greene Publishing Assoc. and Wiley-Interscience, Hoboken, N.J. (1987).

Materials and methods suitable for the maintenance and growth of microbial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in Biotechnology: A Textbook of Industrial Microbiology, $2^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified. *E. coli* strains were typically grown at 37° C. on Luria Bertani ["LB"] plates.

General molecular cloning was performed according to standard methods (Sambrook et al., supra). DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNASTAR Inc., Madison, Wis.).

The meaning of abbreviations is as follows: "sec" means second(s), "min" means minute(s), "h" or "hr" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Nomenclature For Expression Cassettes:

The structure of an expression cassette will be represented by a simple notation system of "X::Y::Z", wherein X describes the promoter fragment, Y describes the gene fragment, and Z describes the terminator fragment, which are all operably linked to one another.

Transformation and Cultivation of *Yarrowia lipolytica*:

*Yarrowia lipolytica* strains with ATCC Accession Nos. #20362, #76982 and #90812 were purchased from the American Type Culture Collection (Rockville, Md.). *Y. lipolytica* strains were typically grown at 28-30° C. in several media, according to the recipes shown below. Agar plates were prepared as required by addition of 20 g/L agar to each liquid media, according to standard methodology.

YPD agar medium (per liter): 10 g of yeast extract [Difco], 20 g of Bacto peptone [Difco]; and 20 g of glucose.

Basic Minimal Media (MM) (per liter): 20 g glucose; 1.7 g yeast nitrogen base without amino acids; 1.0 g proline; and pH 6.1 (not adjusted).

Minimal Media+Leucine (MM+leucine or MMLeu) (per liter): Prepare MM media as above and add 0.1 g leucine.

High Glucose Media (HGM) (per liter): 80 g glucose, 2.58 g $KH_2PO_4$ and 5.36 g $K_2HPO_4$, pH 7.5 (do not need to adjust).

Transformation of *Y. lipolytica* was performed as described in U.S. Pat. Appl. Pub. No. 2009-0093543-A1, hereby incorporated herein by reference.

Fatty Acid Analysis of *Yarrowia lipolytica*:

For fatty acid analysis, cells were collected by centrifugation and lipids were extracted as described in Bligh, E. G. & Dyer, W. J. (*Can. J. Biochem. Physiol.*, 37:911-917 (1959)). Fatty acid methyl esters ["FAMES"] were prepared by trans-esterification of the lipid extract with sodium methoxide (Roughan, G. and Nishida I., *Arch Biochem Biophys.*, 276(1): 38-46 (1990)) and subsequently analyzed with a Hewlett-Packard 6890 GC fitted with a 30 m×0.25 mm (i.d.) HP-INNOWAX (Hewlett-Packard) column. The oven temperature was from 170° C. (25 min hold) to 185° C. at 3.5° C./min.

For direct base transesterification, *Yarrowia* culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Construction Of *Yarrowia lipolytica* Strain Y4036U

*Y. lipolytica* strain Y4036U (Leu-, Ura-), described in Intl. App. Pub. No. WO 2008/073367, was used as the host in Examples 2-4, 6-7 and 9, infra.

The development of strain Y4036U required the construction of strain Y2224 (a FOA resistant mutant from an autonomous mutation of the Ura3 gene of wildtype *Yarrowia* strain ATCC #20362), strain Y4001 (producing 17% EDA with a Leu-phenotype), strain Y4001U1 (producing 17% EDA with a Leu- and Ura-phenotype) and strain Y4036 (producing 18% DGLA with a Leu-phenotype).

The final genotype of strain Y4036U with respect to wildtype *Yarrowia lipolytica* ATCC #20362 was as follows: GPD::FmD12::Pex20, YAT1::FmD12::Oct, YAT1::ME3S::Pex16, GPAT::EgD9e::Lip2, EXP1::EgD9eS::Lip, FBAINm::EgD9eS::Lip2, FBAINm::EgD8M::Pex20 (wherein FmD12 is a *Fusarium moniliforme* Δ12 desaturase gene [Intl. App. Pub. No. WO 2005/047485]; MESS is a codon-optimized $C_{16/18}$ elongase gene, derived from *Mortierella alpina* [Intl. App. Pub. No. WO 2007/046817]; EgD9e is a *Euglena gracilis* Δ9 elongase gene [Intl. App. Pub. No. WO 2007/061742]; EgD9eS is a codon-optimized Δ9 elongase gene, derived from *Euglena gracilis* [Intl. App. Pub. No. WO 2007/061742]; and, EgD8M is a synthetic mutant Δ8 desaturase [Intl. App. Pub. No. WO 2008/073271], derived from *Euglena gracilis* [U.S. Pat. No. 7,256,033]).

Example 1

Construct pDMW369, Comprising EgD5S

The present Example describes plasmid pDMW369, comprising a chimeric FBAIN::EgD5S::Pex20 gene (plasmid construction is described in Intl. App. Pub. No. WO 2007/136671). Plasmid pDMW369 (FIG. 2A; SEQ ID NO:19) contained the following components:

TABLE 7

Components Of Plasmid pDMW369 (SEQ ID NO: 19)

| RE Sites And Nucleotides Within SEQ ID NO: 19 | Description Of Fragment And Chimeric Gene Components |
|---|---|
| EcoR I/BsiW I (6063-318) | FBAIN::EgD5S::Pex20, comprising: FBAIN: *Yarrowia lipolytica* FBAIN promoter (U.S. Pat. No. 7,202,356) EgD5S: codon-optimized Δ5 desaturase (SEQ ID NO: 9), derived from *Euglena gracilis* Pex20: Pex20 terminator sequence of *Yarrowia* Pex20 gene (GenBank Accession No. AF054613) |
| 1354-474 | ColE1 plasmid origin of replication |
| 2284-1424 | ampicillin-resistance gene ($Amp^R$) for selection in *E. coli* |
| 3183-4476 | *Yarrowia* autonomous replication sequence (ARS18; GenBank Accession No. A17608) |
| 6020-4533 | *Yarrowia* Ura 3 gene (GenBank Accession No. AJ306421) |

Example 2

Identification Of HXGG Mutations that Result in Improved Δ5 Desaturase Activity in EgD5S Single amino acid mutations were carried out using pDMW369 (Example 1) as the template and 19 pairs of oligonucleotides (SEQ ID NOs:20-57; Table 8) as primers to individually mutate the proline residue of the HPGG motif of EgD5S (SEQ ID NO:10) by site-directed mutagenesis (QuickChange Kit, Stratagene, Calif.), thereby generating all amino acid substitutions possible (i.e., His-Xaa-Gly-Gly [HXGG] mutants, wherein Xaa can be any amino acid). Plasmids comprising each mutation were transformed into *E. coli* XL2Blue cells (Stratagene). Four colonies from each of the 19 transformations were picked and grown individually in liquid media at 37° C. overnight. Plasmids (i.e., 76 total) were isolated from these cultures and sequenced individually to confirm the mutations.

The wild type pDMW369 plasmid and the isolated mutant plasmids were transformed into strain Y4036U individually, as described in the General Methods. The transformants were selected on MMLeu plates. After 2 days growth at 30° C., two transformants from each transformation reaction were streaked out onto new MMLeu plates and incubated for an additional 2 days at 30° C. The colonies were then used to inoculate 3 mL of MMLeu in a 24 well Qiagen block. The blocks were incubated in a 30° C. incubator shaking at 200 rpm. After the cultures were incubated for 2 days, the blocks were centrifuged, the supernatant was removed and 3 mL of HGM was added. The blocks were placed back in a 30° C. incubator shaking at 200 rpm for an additional 5 days. The cells were collected by centrifugation, lipids were extracted, and FAMEs were prepared by trans-esterification, and subsequently analyzed with a Hewlett-Packard 6890 GC.

The Δ5 desaturase activity attributed to each mutation within the HPGG motif is summarized below in Table 8. EgD5S mutants are designated according to the sequence of the mutant HXGG motif (i.e., the HPGG motif in mutant EgD5S-HAGG had a P2 to A substitution, thereby yielding a His-Ala-Gly-Gly [HAGG] motif, while mutant EgD5S-HRGG possessed a P2 to R substitution, etc.). The conversion efficiency was measured according to the following formula: ([product]/[substrate+product])*100. Results are compared to that of the wildtype EgD5S (SEQ ID NO:10) within plasmid pDMW369, wherein GC analysis determined 8.8%

DGLA and 4.5% ARA of total lipids were produced by the transformants (i.e., average conversion efficiency was 33.8%).

TABLE 8

Δ5 Desaturase Activity In EgD5S And HXGG Motif Mutants

| Y4036U Transformant* | Primers Used For Mutant Motif Construction | Average Conversion Efficiency of DGLA to ARA (%) | Percent Activity With Respect to EgD5S |
|---|---|---|---|
| EgD5S | — | 33.8 | 100 |
| EgD5S-HAGG | SEQ ID NOs: 20 and 21 | 31.4 | 92.9 |
| EgD5S-HRGG | SEQ ID NOs: 22 and 23 | 29.7 | 87.9 |
| EgD5S-HNGG | SEQ ID NOs: 24 and 25 | 30.6 | 88.8 |
| EgD5S-HDGG | SEQ ID NOs: 26 and 27 | ND** | — |
| EgD5S-HCGG | SEQ ID NOs: 28 and 29 | ND** | — |
| EgD5S-HQGG | SEQ ID NOs: 30 and 31 | 31.2 | 92.3 |
| EgD5S-HEGG | SEQ ID NOs: 32 and 33 | ND** | — |
| EgD5S-HGGG | SEQ ID NOs: 34 and 35 | 33.6 | 99.4 |
| EgD5S-HHGG | SEQ ID NOs: 36 and 37 | 32.8 | 97.0 |
| EgD5S-HIGG | SEQ ID NOs: 38 and 39 | 28.0 | 82.8 |
| EgD5S-HLGG | SEQ ID NOs: 40 and 41 | 27.4 | 81.1 |
| EgD5S-HKGG | SEQ ID NOs: 42 and 43 | 32.4 | 95.9 |
| EgD5S-HMGG | SEQ ID NOs: 44 and 45 | 30.1 | 89.1 |
| EgD5S-HFGG | SEQ ID NOs: 46 and 47 | ND** | — |
| EgD5S-HSGG | SEQ ID NOs: 48 and 49 | 28.4 | 84.0 |
| EgD5S-HTGG | SEQ ID NOs: 50 and 51 | 29.7 | 87.9 |
| EgD5S-HWGG | SEQ ID NOs: 52 and 53 | ND** | — |
| EgD5S-HYGG | SEQ ID NOs: 54 and 55 | 34.6 | 102 |
| EgD5S-HVGG | SEQ ID NOs: 56 and 57 | 31.2 | 92.3 |

*Each EgD5S gene (mutant or wildtype) was expressed within pDMW369.
**ND: Did not get mutant in this experiment.

Based on the above, it is clear that the proline residue within the HPGG motif can be substituted with several amino acids without substantially affecting the Δ5 desaturase activity of EgD5S. Preferred proline substitutions, wherein Δ5 desaturase activity was equaled or improved with respect to EgD5S, were present in EgD5S-HGGG (33.6% conversion) and EgD5S-HYGG (34.6% conversion). EgD5S-HHGG (32.8% conversion) functioned with 97% of the Δ5 desaturase activity of EgD5S.

Example 3

Identification of HPGX Mutations that Result in Improved Δ5 Desaturase Activity in EgD5S Single amino acid mutations were carried out using pDMW369 (Example 1) as the template and 19 pairs of oligonucleotides (SEQ ID NOs:59 to 96; Table 9) as primers to individually mutate the second glycine residue of the HPGG motif of EgD5S (SEQ ID NO:10) by site-directed mutagenesis (QuickChange Kit, Stratagene, Calif.), thereby generating all amino acid substitutions possible (i.e., His-Pro-Gly-Xaa [HPGX] mutants). Following mutagenesis, plasmids were transformed into Y4036U, transformants were selected and grown in MMLeu and HGM, and FAMEs were prepared and analyzed by GC, as described in Example 2.

The Δ5 desaturase activity attributed to each mutation within the HPGG motif is summarized below in Table 9. EgD5S mutants are designated according to the sequence of the mutant HPGX motif (i.e., the HPGG motif in mutant EgD5S-HPGA had a G4 to A substitution, thereby yielding a His-Pro-Gly-Ala [HPGA] motif, while mutant EgD5S-HPGR possessed a G4 to R substitution, etc.). Conversion efficiency was measured according to the formula described in Example 2. Results are compared to that of the wildtype EgD5S (SEQ ID NO:10) within plasmid pDMW369, wherein GC analysis determined 8.8% DGLA and 4.5% ARA of total lipids were produced by the transformants (i.e., average conversion efficiency was 33.8%).

TABLE 9

Δ5 Desaturase Activity In EgD5S And HPGX Motif Mutants

| Y4036U Transformant* | Primers Used For Mutant Motif Construction | Average Conversion Efficiency of DGLA to ARA (%) | Percent Activity With Respect to EgD5S |
|---|---|---|---|
| EgD5S | — | 33.8 | 100 |
| EgD5S-HPGA | SEQ ID NOs: 59 and 60 | 31.3 | 92.6 |
| EgD5S-HPGR | SEQ ID NOs: 61 and 62 | 26.9 | 79.6 |
| EgD5S-HPGN | SEQ ID NOs: 63 and 64 | 31.5 | 93.2 |
| EgD5S-HPGD | SEQ ID NOs: 65 and 66 | ND** | — |
| EgD5S-HPGC | SEQ ID NOs: 67 and 68 | ND** | — |
| EgD5S-HPGQ | SEQ ID NOs: 69 and 70 | ND** | — |
| EgD5S-HPGE | SEQ ID NOs: 71 and 72 | ND** | — |
| EgD5S-HPGH | SEQ ID NOs: 73 and 74 | ND** | — |
| EgD5S-HPGI | SEQ ID NOs: 75 and 76 | ND** | — |
| EgD5S-HPGL | SEQ ID NOs: 77 and 78 | ND** | — |
| EgD5S-HPGK | SEQ ID NOs: 79 and 80 | 32.0 | 94.7 |
| EgD5S-HPGM | SEQ ID NOs: 81 and 82 | ND** | — |
| EgD5S-HPGF | SEQ ID NOs: 83 and 84 | ND** | — |
| EgD5S-HPGP | SEQ ID NOs: 85 and 86 | ND** | — |
| EgD5S-HPGS | SEQ ID NOs: 87 and 88 | 37.3 | 110.4 |
| EgD5S-HPGT | SEQ ID NOs: 89 and 90 | 35.5 | 105.0 |
| EgD5S-HPGW | SEQ ID NOs: 91 and 92 | ND** | — |
| EgD5S-HPGY | SEQ ID NOs: 93 and 94 | ND** | — |
| EgD5S-HPGV | SEQ ID NOs: 95 and 96 | ND** | — |

*Each EgD5S gene (mutant or wildtype) was expressed within pDMW369.
**ND: Did not get mutant in this experiment.

The results demonstrated that the second glycine residue within the HPGG motif can be substituted with several amino acids without substantially affecting the Δ5 desaturase activity of EgD5S. Preferred glycine substitutions, wherein Δ5 desaturase activity was equaled or improved with respect to EgD5S, were present in EgD5S-HPGS (37.3% conversion) and EgD5S-HPGT (35.5% conversion).

Example 4

Quantitative Analysis of EgD5 Mutants that Performed at or Above Wildtype EgD5S Level Once the preliminary analyses of the amino acid substitutions were complete (Examples 2 and 3), a quantitative analysis of those mutations that performed approximately equivalently or above the wildtype EgD5S conversion rate was carried out (i.e., EgD5S-HGGG, EgD5S-HHGG, EgD5S-HYGG, EgD5S-HPGS and EgD5S-HPGT). The plasmids containing the above mutations were designated as pDMW369-HGGG, pDMW369-HHGG, pDMW369-HYGG, pDMW369-HPGS and pDMW369-HPGT, respectively. These plasmids, along with pDMW369, were re-transformed into Y4036U (General Methods) and plated on MMLeu. The plates were incubated at 30° C. for about 4 days. Twelve transformants from each plate were restreaked onto fresh MMLeu plates and incubated again at 30° C. The transformants were inoculated into 3 mL of MMLeu in a 24 well block format. The blocks were incubated at 30° C. at 200 rpm for 2 days. After 2 days' growth the blocks were centrifuged, the supernatant decanted and the pellets resuspended in HGM. The blocks were incubated at 30° C. for an additional 5 days. The cells were collected by centrifugation, lipids were extracted, and FAMEs were prepared by trans-esterification, and subsequently analyzed with a Hewlett-Packard 6890 GC.

The average DGLA to ARA conversion rate of 12 samples are summarized below in Table 10:

TABLE 10

Δ5 Desaturase Activity In EgD5S HXGX Motif Mutants

| Y4036U Transformant* | Average Conversion Efficiency of DGLA to ARA (%) | Percent Activity With Respect to EgD5S |
|---|---|---|
| EgD5S | 30.4 | 100 |
| EgD5S- HGGG | 31.8 | 104.6 |
| EgD5S- HHGG | 31.5 | 103.6 |
| EgD5S- HYGG | 26.0 | 85.5 |
| EgD5S- HPGS | 32.5 | 106.9 |
| EgD5S- HPGT | 30.1 | 99.0 |

*Each EgD5S gene (mutant or wildtype) was expressed within pDMW369.

This experiment confirmed that the Δ5 desaturase activities of EgD5S-HGGG and EgD5S-HHGG (SEQ ID NO:58) and EgD5S-HPGS (SEQ ID NO:97) mutants were increased relative to the wildtype EgD5S control. A suitable nucleotide sequence encoding EgD5S-HGGG is set forth as SEQ ID NO:190, a suitable sequence encoding EgD5S-HHGG is set forth as SEQ ID NO:191 and a suitable nucleotide sequence encoding EgD5S-HPGS is set forth as SEQ ID NO:192.

Example 5

Generation of Construct pZUFmEaD5S, Comprising EaD5S

The present Example describes the construction of plasmid pZUFmEaD5S comprising a chimeric FBAINm::EaD5S::Pex20 gene. Plasmid pZUFmEaD5S (SEQ ID NO:98) was constructed by replacing the Nco I/Not I fragment of pZUF17 (FIG. 2B; SEQ ID NO:99) with the Nco I/Not I EaD5S fragment from pEaD5S (SEQ ID NO:100) [wherein plasmid pEaD5S (SEQ ID NO:100) was created when the EaD5S gene (SEQ ID NO:13) was cloned into pUC57 (GenBank Accession No. Y14837)]. The product of this ligation was pZUFmEaD5S, which thereby contained the following components:

TABLE 11

Components Of Plasmid pZuFmEaD5S (SEQ ID NO: 98)

| RE Sites And Nucleotides Within SEQ ID NO: 98 | Description Of Fragment And Chimeric Gene Components |
|---|---|
| Swa I/BsiW I (7435-1686) | FBAIN::EaD5S::Pex20, comprising: FBAIN: *Yarrowia lipolytica* FBAIN promoter (U.S. Pat. No. 7,202,356) EaD5S: codon-optimized Δ5 desaturase (SEQ ID NO: 13), derived from *Euglena anabaena* Pex20: Pex20 terminator sequence of *Yarrowia* Pex20 gene (GenBank Accession No. AF054613) |
| 2722-1842 | ColE1 plasmid origin of replication |
| 3652-2792 | ampicillin-resistance gene (Amp$^R$) for selection in *E. coli* |
| 4554-5855 | *Yarrowia* autonomous replication sequence (ARS18; GenBank Accession No. A17608) |
| 7399-5898 | *Yarrowia* Ura 3 gene (GenBank Accession No. AJ306421 ) |

Example 6

Identification of HXGG Mutations that Result in Improved Δ5 Desaturase Activity in EaD5S Single amino acid mutations were carried out using pZUFmEaD5S (Example 5) as the template and 19 pairs of oligonucleotides (SEQ ID NOs:101 to 138; Table 12) as primers to individually mutate the proline residue of the HPGG motif of EaD5S (SEQ ID NO:14) by site-directed mutagenesis (QuickChange Kit, Stratagene, Calif.), thereby generating all amino acid substitutions possible (i.e., His-Xaa-Gly-Gly [HXGG] mutants). Plasmids from each mutation were transformed into *E. coli* XL2Blue cells. Four colonies from each of the 19 transformations were picked and grown individually in liquid media at 37° C. overnight. Plasmids (i.e., 76 total) were isolated from these cultures and sequenced individually to confirm the mutations.

The wild type pZUFmEaD5S plasmid and the isolated mutant plasmids were transformed into strain Y4036U individually, as described in the General Methods. The transformants were selected on MMLeu plates and then grown in liquid MMLeu and HGM media, as described in Example 2 (except that the speed of the incubator was increased from 200 to 250 rpm). The cells were collected by centrifugation, lipids were extracted, and FAMEs were prepared by transesterification, and subsequently analyzed with a Hewlett-Packard 6890 GC.

The Δ5 desaturase activities attributed to each mutation within the HPGG motif are summarized below in Table 12. EaD5S mutants are designated according to the sequence of the mutant HXGG motif (i.e., the HPGG motif in mutant EaD5S-HAGG had a P2 to A substitution, thereby yielding a His-Ala-Gly-Gly [HAGG] motif, while mutant EaD5S-HRGG possessed a P2 to R substitution, etc.). The conversion efficiency was measured according to the following formula: ([product]/[substrate+product])*100. Results are compared to that of the wildtype EaD5S (SEQ ID NO:14) within plasmid pZUFmEaD5S, wherein GC analysis determined the average DGLA to ARA conversion efficiency of 2 transformants was 25%.

TABLE 12

Δ5 Desaturase Activity In EaD5S And HXGG Motif Mutants

| Y4036U Transformant* | Primers Used For Mutant Motif Construction | Average Conversion Efficiency of DGLA to ARA (%) | Percent Activity With Respect to EaD5S |
|---|---|---|---|
| EaD5S | — | 25.0 | 100 |
| EaD5S-HAGG | SEQ ID NOs: 101 and 102 | 26.4 | 105.6 |
| EaD5S-HRGG | SEQ ID NOs: 103 and 104 | 24.9 | 99.0 |
| EaD5S-HNGG | SEQ ID NOs: 105 and 106 | 23.2 | 92.8 |
| EaD5S-HDGG | SEQ ID NOs: 107 and 108 | 8.3 | 33.2 |
| EaD5S-HCGG | SEQ ID NOs: 109 and 110 | 26.2 | 104.8 |
| EaD5S-HQGG | SEQ ID NOs: 111 and 112 | 20.7 | 82.8 |
| EaD5S-HEGG | SEQ ID NOs: 113 and 114 | 8.8 | 35.2 |
| EaD5S-HGGG | SEQ ID NOs: 115 and 116 | 18.9 | 75.6 |
| EaD5S-HHGG | SEQ ID NOs: 117 and 118 | 20.4 | 81.6 |
| EaD5S-HIGG | SEQ ID NOs: 119 and 120 | ND** | — |
| EaD5S-HLGG | SEQ ID NOs: 121 and 122 | 21.1 | 84.4 |
| EaD5S-HKGG | SEQ ID NOs: 123 and 124 | 25.2 | 100.8 |
| EaD5S-HMGG | SEQ ID NOs: 125 and 126 | 23.6 | 94.4 |
| EaD5S-HFGG | SEQ ID NOs: 127 and 128 | 21.2 | 84.8 |
| EaD5S-HSGG | SEQ ID NOs: 129 and 130 | 23.0 | 95.6 |
| EaD5S-HTGG | SEQ ID NOs: 131 and 132 | 25.8 | 103.2 |

TABLE 12-continued

Δ5 Desaturase Activity In EaD5S And HXGG Motif Mutants

| Y4036U Transformant* | Primers Used For Mutant Motif Construction | Average Conversion Efficiency of DGLA to ARA (%) | Percent Activity With Respect to EaD5S |
|---|---|---|---|
| EaD5S-HWGG | SEQ ID NOs: 133 and 134 | 14.0 | 56.0 |
| EaD5S-HYGG | SEQ ID NOs: 135 and 136 | 19.9 | 79.6 |
| EaD5S-HVGG | SEQ ID NOs: 137 and 138 | ND** | — |

*Each EaD5S gene (mutant or wildtype) was expressed within pZuFmEaD5S.
**ND: Did not get mutant in this experiment.

Based on the above, it is clear that the proline residue within the HPGG motif can be substituted with several amino acids without substantially affecting the Δ5 desaturase activity of EaD5S. Preferred proline substitutions, wherein Δ5 desaturase activity was improved with respect to EaD5S, were present in EaD5S-HAGG (26.3% conversion), EaD5S-HCGG (26.2% conversion), EaD5S-HKGG (25.2% conversion) and EaD5S-HTGG (25.8% conversion).

Quantitative Analysis of EaD5 Mutants that Performed at or Above Wildtype EaD5S Level A more quantitative analysis of those mutations that performed with approximately equivalent or improved activity with respect to the wildtype EaD5S conversion rate was carried out (i.e., EaD5S-HAGG, EaD5S-HRGG, EaD5S-HNGG, EaD5S-HCGG, EaD5S-HHGG, EaD5S-HLGG, EaD5S-HKGG, EaD5S-HMGG, EaD5S-HFGG, EaD5S-HSGG and EaD5S-HTGG). The plasmids containing the above mutations were designated as pZuFmEaD5S-HAGG, pZuFmEaD5S-HRGG, pZuFmEaD5S-HNGG, pZuFmEaD5S-HCGG, pZuFmEaD5S-HHGG, pZuFmEaD5S-HLGG, pZuFmEaD5S-HKGG, pZuFmEaD5S-HMGG, pZuFmEaD5S-HFGG, pZuFmEaD5S-HSGG, and pZuFmEaD5S-HTGG, respectively. These plasmids, along with pZuFmEaD5S, were re-transformed into Y4036U (General Methods) and plated on MMLeu. The plates were incubated at 30° C. for about 4 days. Six transformants from each plate were re-streaked onto fresh MMLeu plates and incubated again at 30° C. The transformants were inoculated into 3 mL of MMLeu in a 24 well block format. The blocks were incubated at 30° C. at 200 rpm for 2 days. After 2 days' growth the blocks were centrifuged, the supernatants were decanted and the pellets were re-suspended in HGM. The blocks were incubated at 30° C. for an additional 5 days. The cells were collected by centrifugation, lipids were extracted, and FAMEs were prepared by trans-esterification, and subsequently analyzed with a Hewlett-Packard 6890 GC.

The average DGLA to ARA conversion rate of 6 samples are summarized below in Table 13:

TABLE 13

Δ5 Desaturase Activity In EaD5S HXGG Motif Mutants

| Y4036U Transformant* | Average Conversion Efficiency of DGLA to ARA (%) | Percent Activity With Respect to EaD5S |
|---|---|---|
| EaD5S | 24.0 | 100 |
| EaD5S-HAGG | 23.8 | 99.2 |
| EaD5S-HRGG | 23.0 | 95.8 |
| EaD5S-HNGG | 20.7 | 86.2 |
| EaD5S-HCGG | 25.9 | 107.9 |

TABLE 13-continued

Δ5 Desaturase Activity In EaD5S HXGG Motif Mutants

| Y4036U Transformant* | Average Conversion Efficiency of DGLA to ARA (%) | Percent Activity With Respect to EaD5S |
|---|---|---|
| EaD5S-HHGG | 20.4 | 85.0 |
| EaD5S-HLGG | 16.7 | 69.6 |
| EaD5S-HKGG | 20.7 | 86.3 |
| EaD5S-HMGG | 23.4 | 97.5 |
| EaD5S-HFGG | 21.2 | 88.3 |
| EaD5S-HSGG | 23.8 | 99.2 |
| EaD5S-HTGG | 21.4 | 89.2 |

*Each EaD5S gene (mutant or wildtype) was expressed within pZuFmEaD5S.

This experiment confirmed that the Δ5 desaturase activity of mutant EaD5S-HCGG (SEQ ID NO:139) was increased relative to the wildtype EaD5S control. A suitable nucleotide sequence encoding EaD5S-HCGG is set forth as SEQ ID NO:193.

Example 7

Generation of Construct pZUFmRD5S, Comprising RD5S

The present Example describes plasmid pZURD5S, comprising a chimeric FBAIN::RD5S::Pex20 gene (plasmid construction is described in Intl. App. Pub. No. WO 2007/136646). Plasmid pZURD5S (SEQ ID NO:140) is identical in construction to pDMW369 (Example 1; SEQ ID NO:19), with the exception that RD5S (SEQ ID NO:17) was substituted in place of EgD5S (SEQ ID NO:9).

Example 8

Identification of HXGG Mutations that Result in Improved Δ5 Desaturase Activity in RD5S Single amino acid mutations were carried out by using pZURD5S (Example 7) as the template and 19 pairs of oligonucleotides (SEQ ID NOs:141 to 178; Table 14) as primers to individually mutate the proline residue of the HPGG motif of RD5S (SEQ ID NO:17) by site-directed mutagenesis (QuickChange Kit, Stratagene, Calif.), thereby generating all amino acid substitutions possible (i.e., His-Xaa-Gly-Gly [HXGG] mutants). Plasmids from each mutation were transformed into E. coli XL2Blue cells. Four colonies from each of the 19 transformations were picked and grown individually in liquid media at 37° C. overnight. Plasmids (i.e., 76 total) were isolated from these cultures and sequenced individually to confirm the mutations.

The wild type pZURD5S plasmid and the isolated mutant plasmids were transformed into strain Y4036U individually, as described in the General Methods. The transformants were selected on MMLeu plates and then grown in liquid MMLeu and HGM media, as described in Example 2 (except that the speed of the incubator was increased from 200 to 250 rpm). The cells were collected by centrifugation, lipids were extracted, and FAMEs were prepared by trans-esterification, and subsequently analyzed with a Hewlett-Packard 6890 GC.

The Δ5 desaturase activities attributed to each mutation within the HPGG motif are summarized below in Table 14. RD5S mutants are designated according to the sequence of the mutant HXGG motif (i.e., the HPGG motif in mutant RD5S-HAGG had a P2 to A substitution, thereby yielding a His-Ala-Gly-Gly [HAGG] motif, while mutant RD5S-HRGG possessed a P2 to R substitution, etc.). The conversion efficiency was measured according to the following formula: ([product]/[substrate+product])*100. Results are compared to that of the wildtype RD5S (SEQ ID NO:18) within plasmid pZURD5S, wherein GC analysis determined the average DGLA to ARA conversion efficiency of 2 transformants was 25.1%.

TABLE 14

Δ5 Desaturase Activity In RD5S And HXGG Motif Mutants

| Y4036U Transformant* | Primers Used For Mutant Motif Construction | Average Conversion Efficiency of DGLA to ARA (%) | Percent Activity With Respect to RD5S |
|---|---|---|---|
| RD5S | — | 25.1 | 100 |
| RD5S-HAGG | SEQ ID NOs: 141 and 142 | 23.2 | 92.4 |
| RD5S-HRGG | SEQ ID NOs: 143 and 144 | ND** | — |
| RD5S-HNGG | SEQ ID NOs: 145 and 146 | ND** | — |
| RD5S-HDGG | SEQ ID NOs: 147 and 148 | 13.1 | 52.2 |
| RD5S-HCGG | SEQ ID NOs: 149 and 150 | 34.8 | 138.6 |
| RD5S-HQGG | SEQ ID NOs: 151 and 152 | 20.2 | 80.5 |
| RD5S-HEGG | SEQ ID NOs: 153 and 154 | 18.6 | 74.1 |
| RD5S-HGGG | SEQ ID NOs: 155 and 156 | 18.7 | 74.1 |
| RD5S-HHGG | SEQ ID NOs: 157 and 158 | ND** | — |
| RD5S-HIGG | SEQ ID NOs: 159 and 160 | ND** | — |
| RD5S-HLGG | SEQ ID NOs: 161 and 162 | ND** | — |
| RD5S-HKGG | SEQ ID NOs: 163 and 164 | 22.2 | 88.4 |
| RD5S-HMGG | SEQ ID NOs: 165 and 166 | 21.2 | 84.1 |

TABLE 14-continued

Δ5 Desaturase Activity In RD5S And HXGG Motif Mutants

| Y4036U Transformant* | Primers Used For Mutant Motif Construction | Average Conversion Efficiency of DGLA to ARA (%) | Percent Activity With Respect to RD5S |
|---|---|---|---|
| RD5S-HFGG | SEQ ID NOs: 167 and 168 | ND** | — |
| RD5S-HSGG | SEQ ID NOs: 169 and 170 | ND** | — |
| RD5S-HTGG | SEQ ID NOs: 171 and 172 | 22.6 | 90.0 |
| RD5S-HWGG | SEQ ID NOs: 173 and 174 | 28.5 | 113.5 |
| RD5S-HYGG | SEQ ID NOs: 175 and 176 | ND** | — |
| RD5S-HVGG | SEQ ID NOs: 177 and 178 | 20.6 | 82.0 |

*Each RD5S gene (mutant or wildtype) was expressed within pZURD5S.
**ND: Did not get mutant in this experiment.

Based on the above, it is clear that the proline residue within the HPGG motif can be substituted with several amino acids without substantially affecting the Δ5 desaturase activity of RD5S. Preferred proline substitutions, wherein Δ5 desaturase activity was improved with respect to RD5S, were present in RD5S-HCGG (34.8% conversion) and RD5S-HWGG (28.5% conversion).

A quantitative analysis of those mutations that performed at or above the wildtype RD5S conversion rate (i.e., RD5S-HCGG and RD5S-HWGG (SEQ ID NO:179)) will be carried out, as described previously for EgD5S and EaD5S mutants. A suitable nucleotide sequence encoding RD5S-HCGG is set forth as SEQ ID NO:194 and a suitable nucleotide sequence encoding RD5S-HWGG is set forth as SEQ ID NO:195.

What is claimed is:

1. An isolated nucleic acid molecule comprising a nucleotide sequence encoding a *Euglena gracilis* delta-5 desaturase mutant polypeptide, wherein the mutant polypeptide comprises an amino acid sequence that has at least 95% amino acid sequence identity with the amino acid sequence of SEQ ID NO:8, wherein the amino acid sequence of the mutant polypeptide has Gly or His at the position corresponding to amino acid 34 of SEQ ID NO:8, and wherein said mutant polypeptide has delta-5 desaturase enzymatic activity and has a dihomo-γ-linolenic acid to arachidonic acid conversion efficiency that is greater than the dihomo-γ-linolenic acid to arachidonic acid conversion efficiency of a wildtype *Euglena gracilis* delta-5 desaturase polypeptide having the heme-binding motif as set forth as SEQ ID NO:180 (HPGG).

2. A microbial host cell transformed with the isolated nucleic acid molecule of claim 1.

3. The microbial host cell of claim 2 selected from the group consisting of: bacteria, yeasts, algae, euglenoids, stramenopiles, oomycetes and fungi.

4. The microbial host cell of claim 3 wherein the microbial host cell is an oleaginous yeast.

5. The microbial host cell of claim 4 wherein the oleaginous yeast is selected from the group consisting of: *Yarrowia, Candida, Rhodotorula, Rhodosporidium, Cryptococcus, Trichosporon* and *Lipomyces*.

6. A method for producing arachidonic acid comprising growing the microbial host cell according to claim 2 in the presence of dihomo-γ-linolenic acid, wherein the dihomo-γ-linolenic acid is converted to arachidonic acid.

7. A method for producing eicosapentaenoic acid comprising growing the microbial host cell according to claim 2 in the presence of eicosatetraenoic acid, wherein the eicosatetraenoic acid is converted to eicosapentaenoic acid.

8. The microbial host cell of claim 2 wherein the microbial host cell is an oleaginous bacterium, yeast, algae, euglenoid, stramenopile, oomycete or fungus and produces a polyunsaturated fatty acid selected from the group consisting of omega-6 fatty acids and omega-3 fatty acids.

9. The isolated nucleic acid molecule of claim 1, wherein said mutant polypeptide comprises the amino acid sequence of SEQ ID NO:58.

10. The isolated nucleic acid molecule of claim 9, wherein said nucleotide sequence is selected from the group consisting of SEQ ID NO:190 and SEQ ID NO:191.

* * * * *